US 8,389,485 B2
Mar. 5, 2013

(12) United States Patent
Czech et al.

(54) ENCAPSULATED NANOPARTICLES FOR NUCLEIC ACID DELIVERY

(75) Inventors: Michael P. Czech, Westborough, MA (US); Gary R. Ostroff, Worcester, MA (US); Myriam Aouadi, Worcester, MA (US)

(73) Assignee: University of Massachusetts, Boston, MA (US)

( * ) Notice: Subject to any disclaimer, the term of this patent is extended or adjusted under 35 U.S.C. 154(b) by 177 days.

(21) Appl. No.: 12/260,998

(22) Filed: Oct. 29, 2008

(65) Prior Publication Data

US 2009/0226528 A1 Sep. 10, 2009

Related U.S. Application Data

(60) Provisional application No. 61/001,025, filed on Oct. 29, 2007, provisional application No. 61/068,184, filed on Mar. 4, 2008.

(51) Int. Cl.
*C12N 15/11* (2006.01)
*C07H 21/02* (2006.01)

(52) U.S. Cl. .............. 514/44 A; 536/24.5; 424/493; 424/499; 977/773; 977/774; 977/778; 977/783; 977/905; 977/906; 977/915

(58) Field of Classification Search .................. None
See application file for complete search history.

(56) References Cited

U.S. PATENT DOCUMENTS

| | | | |
|---|---|---|---|
| 3,737,337 A | 6/1973 | Schnoring et al. |
| 3,891,570 A | 6/1975 | Fukushima et al. |
| 4,160,452 A | 7/1979 | Theeuwes |
| 4,256,108 A | 3/1981 | Theeuwes |
| 4,265,874 A | 5/1981 | Bonsen et al. |
| 4,384,975 A | 5/1983 | Fong |
| 4,389,330 A | 6/1983 | Tice et al. |
| 4,595,660 A | 6/1986 | Ostroff et al. |
| 4,652,441 A | 3/1987 | Okada et al. |
| 4,663,308 A | 5/1987 | Saffran et al. |
| 4,777,049 A | 10/1988 | Magruder et al. |
| 4,810,646 A | 3/1989 | Jamas et al. |
| 4,946,778 A | 8/1990 | Ladner et al. |
| 4,956,778 A | 9/1990 | Naito |
| 4,992,540 A | 2/1991 | Jamas et al. |
| 5,028,703 A | 7/1991 | Jamas et al. |
| 5,032,401 A | 7/1991 | Jamas et al. |
| 5,082,936 A | 1/1992 | Jamas et al. |
| 5,091,513 A | 2/1992 | Huston et al. |
| 5,132,405 A | 7/1992 | Huston et al. |
| 5,322,841 A | 6/1994 | Jamas et al. |
| 5,401,727 A | 3/1995 | Rorstad et al. |
| 5,407,609 A | 4/1995 | Tice et al. |
| 5,488,040 A | 1/1996 | Jamas et al. |
| 5,504,079 A | 4/1996 | Jamas et al. |
| 5,532,223 A | 7/1996 | Jamas et al. |
| 5,545,806 A | 8/1996 | Lonberg et al. |
| 5,569,825 A | 10/1996 | Lonberg et al. |
| 5,607,677 A | 3/1997 | Jamas et al. |
| 5,622,939 A | 4/1997 | Jamas et al. |
| 5,622,940 A | 4/1997 | Ostroff |
| 5,663,324 A | 9/1997 | James et al. |
| 5,663,369 A | 9/1997 | Kreutzer et al. |
| 5,705,153 A | 1/1998 | Shorr et al. |
| 5,741,495 A | 4/1998 | Jamas et al. |
| 5,783,569 A | 7/1998 | Jamas et al. |
| 5,811,542 A | 9/1998 | Jamas et al. |
| 5,814,318 A | 9/1998 | Lonberg et al. |
| 5,817,643 A | 10/1998 | Jamas et al. |
| 5,849,720 A | 12/1998 | Jamas et al. |
| 5,879,680 A | 3/1999 | Ginns et al. |
| 5,911,983 A | 6/1999 | Barranger et al. |
| 5,968,811 A | 10/1999 | Greenshields |
| 6,022,703 A | 2/2000 | Long et al. |
| 6,074,864 A | 6/2000 | Ginns et al. |
| 6,118,045 A | 9/2000 | Reuser et al. |
| 6,133,229 A | 10/2000 | Gibson et al. |
| 6,369,216 B1 | 4/2002 | Patchen et al. |
| 6,372,499 B1 | 4/2002 | Midoux et al. |
| 6,379,965 B1 | 4/2002 | Boutin |
| 6,420,176 B1 | 7/2002 | Lisziewicz et al. |
| 6,444,448 B1 | 9/2002 | Wheatcroft et al. |
| 6,476,003 B1 | 11/2002 | Jordan et al. |
| 6,495,570 B2 | 12/2002 | Jacob et al. |
| 6,512,097 B1 | 1/2003 | Marks et al. |
| 6,696,272 B1 | 2/2004 | Mahuran et al. |
| 6,740,336 B2 * | 5/2004 | Trubetskoy et al. ......... 424/450 |
| 6,846,809 B2 | 1/2005 | Cristiano et al. |
| 6,855,808 B2 | 2/2005 | Goto et al. |
| 7,018,986 B2 | 3/2006 | Sorgente et al. |

(Continued)

FOREIGN PATENT DOCUMENTS

| | | |
|---|---|---|
| EP | 0242135 A2 | 10/1987 |
| JP | 2007-516687 | 6/2007 |

(Continued)

OTHER PUBLICATIONS

Khoury et al (Arthritis and Rheumatism 54(6): 1867-1877, Jun. 2006).*
Schiffelers et al (Arthritis & Rheumatism 52(4): 1314-1318, 2005).*
El-Gabalawy et al (Arthritis Res. 4) Suppl 3): S297-S301, 2002).*
JAVMA News, May 15, 2009, downloaded Jul. 30, 2011 from http://www.avma.org/onlnews/javma/may09/090515u_pf.asp.*
Mayo Clinic Staff (Rheumatoid Arthritis Treatments and Drugs, Nov. 3, 2009), downloaded from http://www.mayoclinic.com/health/rheumatoid-arthritis/DS00020/DSECTION=treatments-and-drugs on Jul. 30, 2011.*
Aouadi, Myriam et al., "Orally delivered siRNA targeting macrophage Map4k4 suppresses systemic inflammation," Nature, vol. 458(7242):1180-1184 (2009).

(Continued)

*Primary Examiner* — Richard Schnizer
(74) *Attorney, Agent, or Firm* — Nelson Mullins Riley & Scarborough LLP; Debra J. Milasincic, Esq.

(57) ABSTRACT

Methods and compositions for delivering agents (e.g., gene silencing agents) and molecules to cells using yeast cell wall particles are presented herein. Embodiments of the invention are particularly useful for the delivery of nucleic acids (e.g., siRNAs) to cells.

38 Claims, 45 Drawing Sheets

U.S. PATENT DOCUMENTS

| | | | |
|---|---|---|---|
| 7,022,685 | B2 | 4/2006 | Patchen et al. |
| 7,220,427 | B2 | 5/2007 | Jordan |
| 7,229,623 | B1 | 6/2007 | Cheever et al. |
| 7,740,861 | B2 | 6/2010 | Ostroff |
| 2002/0032170 | A1 | 3/2002 | Jamas et al. |
| 2002/0143174 | A1 | 10/2002 | Patchen et al. |
| 2003/0216346 | A1 | 11/2003 | Sakurai et al. |
| 2004/0014715 | A1 | 1/2004 | Ostroff |
| 2004/0116380 | A1 | 6/2004 | Jamas et al. |
| 2004/0162235 | A1 | 8/2004 | Trubetskoy et al. |
| 2005/0245480 | A1 | 11/2005 | Ostroff et al. |
| 2005/0255487 | A1 | 11/2005 | Khvorova et al. |
| 2005/0281781 | A1 | 12/2005 | Ostroff |
| 2006/0083718 | A1 | 4/2006 | Ginns et al. |
| 2006/0134663 | A1 | 6/2006 | Harkin et al. |
| 2006/0160133 | A1 | 7/2006 | Czech et al. |
| 2006/0165700 | A1 | 7/2006 | Ostroff et al. |
| 2006/0247205 | A1 | 11/2006 | Patchen et al. |
| 2007/0213284 | A1 | 9/2007 | Sohail et al. |
| 2008/0044438 | A1 | 2/2008 | Ostroff et al. |
| 2008/0220038 | A1 | 9/2008 | Franklin et al. |
| 2012/0070376 | A1 | 3/2012 | Ostroff et al. |

FOREIGN PATENT DOCUMENTS

| | | |
|---|---|---|
| JP | 2008-503472 | 2/2008 |
| WO | 89/05850 A1 | 6/1989 |
| WO | 90/15596 A1 | 12/1990 |
| WO | 91/03248 A2 | 3/1991 |
| WO | 91/03495 A1 | 3/1991 |
| WO | 92/07064 A1 | 4/1992 |
| WO | 94/04163 A1 | 3/1994 |
| WO | 00/18411 A1 | 4/2000 |
| WO | 02/12348 A2 | 2/2002 |
| WO | 2004/012657 A2 | 2/2004 |
| WO | 2004/014320 A2 | 2/2004 |
| WO | 2004/021994 A2 | 3/2004 |
| WO | 2004/037232 A1 | 5/2004 |
| WO | WO-2004/053103 A2 | 6/2004 |
| WO | 2005/014776 A2 | 2/2005 |
| WO | 2005/018544 A2 | 3/2005 |
| WO | WO-2006/007372 A2 | 1/2006 |
| WO | WO-2006/032039 A2 | 3/2006 |
| WO | WO-2007/050643 A2 | 5/2007 |
| WO | 2007/109564 A2 | 9/2007 |
| WO | WO-2007/099387 A1 | 9/2007 |
| WO | 2009/058913 A2 | 5/2009 |

OTHER PUBLICATIONS

Powelka, Aimee M. et al., "Suppression of oxidative metabolism and mitochondrial biogenesis by the transcriptional corepressor RIP140 in mouse adipocytes," The Journal of Clinical Investigation, vol. 116(1):125-136 (2006).

Soto, Ernesto R. et al., "Characterization of Multilayered Nanoparticles Inside Yeast Cell Wall Particles for DNA Delivery," Bioconjugate Chemistry, vol. 19(4):840-848 (2008).

Tang, Xiaoqing et al., "An RNA interference-based screen identifies MAP4K4/NIK as a negative regulator of PPARgamma, adipogenesis, and insulin-responsive hexose transport," PNAS, vol. 103(7):2087-2092 (2006).

Tesz, Gregory J. et al., "Tumor Necrosis Factor alpha (TNFalpha) Stimulates Map4k4 Expression through TNFalpha Receptor 1 Signaling to c-Jun and Activating Transcription Factor 2," The Journal of Biological Chemistry, vol. 282 (27):19302-19312 (2007).

Guilherme, Adilson et al., "Adipocyte dysfunctions linking obesity to insulin resistance and type 2 diabetes," Nature Reviews, Molecular Cell Biology, vol. 9:367-377 (2008).

Shoelson, Steven E. et al., "Inflammation and insulin resistance," The Journal of Clinical Investigation, vol. 116 (7):1793-1801 (2006).

Fattal, Elias et al., "State of the art and perspectives for the delivery of antisense oligonucleotides and siRNA polymeric nanocarriers," International Journal of Pharmaceutics, vol. 364:237-248 (2008).

International Search Report and Written Opinion for Application No. PCT/US2008/081653, dated Nov. 10, 2009.

Filleur, Stephanie et al., "SiRNA-mediated Inhibition of Vascular Endothelial Growth Factor Severely Limits Tumor Resistance to Antiangiogenic Thrombospondin-1 and Slows Tumor Vascularization and Growth," Cancer Research, vol. 63:3919-3922 (2003).

McCaffrey, Anton P. et al., "RNA interference in adult mice," Nature, vol. 418:38-39 (2002).

Peer, Dan et al., "Selective gene silencing in activated leukocytes by targeting siRNAs to the integrin lymphocyte function-associated antigen-1," PNAS, vol. 104(10):4095-4100 (2007).

Song, Erwei et al., "Antibody mediated in vivo delivery of small interfering RNAs via cell-surface receptors," Nature Biotechnology, vol. 23(6):709-717 (2005).

Sorensen, Dag R. et al., "Gene Silencing by Systemic Delivery of Synthetic siRNAs in Adult Mice," J. Mol. Biol., vol. 327:761-766 (2003).

Soutschek, Jurgen et al., "Therpeutic silencing of an endogenous gene by systemic administration of modified siRNAs," Nature, vol. 432:173-178 (2004).

Wesche-Soldato, Doreen E. et al., "In vivo delivery of caspase-8 or Fas siRNA improves the survival of septic mice," Blood, vol. 106(7):2295-2301 (2005).

Zimmermann, Tracy S. et al., "RNAi-mediated gene silencing in non-human primates," Nature, vol. 441:111-114 (2006).

Agarwal, Sarika et al., "Linkage Specificity and Role of Properdin in Activation of the Alternative Complement Pathway by Fungal Glycans," mBio, vol. 2(5):e00178, 10 pages (2011).

Aviner, S. et al., "Anaphylactoid Reaction to Imiglucerase, but Not to Alglucerase, in a Type I Gaucher Patient," Blood Cells, Molecules, and Diseases, vol. 25(5):92-94 (1999).

Beier, Rita et al., "Kinetics of particle uptake in the domes of Peyer's patches," Am. J. Physiol., vol. 275:G130-G137 (1998).

Bell, Stacey et al., "Effect of beta-Glucan from Oats and Yeast on Serum Lipids," Critical Reviews in Food Science and Nutrition, vol. 39(2):189-202 (1999).

Bogwald, Jarl et al., "Lysosomal Glycosidases in Mouse Peritoneal Macrophages Stimulated in Vitro With Soluble and Insoluble Glycans," Journal of Leukocyte Biology, vol. 35:357-371 (1984).

Bonfils, E. et al., "Drug targeting: synthesis and endocytosis of oligonucleotide-neoglycoprotein conjugates," Nucleic Acids Research, vol. 20(17):4621-4629 (1992).

Bonten, Erik J. et al., "Targeting macrophages with baculovirus-produced lysosomal enzymes: implications for enzyme replacement therapy of the glycoprotein storage disorder galactosialidosis," The FASEB Journal, doi:10.1096/fj.03-0941fje (2004).

Brooks, Doug A. et al., "Significance of immune response to enzyme-replacement therapy for patients with lysosomal storage disorder," Trends in Molecular Medicine, vol. 9(10):450-453 (2003).

Burke, Bernard, "Macrophages as novel cellular vehicles for gene therapy," Expert Opin. Biol. Ther., vol. 3 (6):919-924 (2003).

Burke, B. et al., "Macrophages in gene therapy: cellular delivery vehicles and in vivo targets," Journal of Leukocyte Biology, vol. 72:417-428 (2002).

Champagne, M.J. et al., "Binding of GM1-ganglioside to a synthetic peptide derived from the lysosomal sphingolipid-activator-protein saposin B," FEBS Lett., vol. 347(2-3):265-267 (1994).

Chang, P.L., "Microencapsulation—An alternative approach to gene therapy," Transfusion Science, vol. 17(1):35-43 (1996).

Charrow, Joel et al., "Enzyme Replacement Therapy and Monitoring for Children with Type 1 Gaucher Disease: Consensus Recommendations," J. Pediatr., vol. 144:112-120 (2004).

Chaudhary, Vijay K. et al., "A rapid method of cloning functional variable-region antibody genes in Escherichia coli as single-chain immunotoxins," Proc. Natl. Acad. Sci. USA, vol. 87:1066-1070 (1990).

Cho, Monique E. et al., "Fabry disease in the era of enzyme replacement therapy: a renal perspective," Pediatr. Nephrol., vol. 19:583-593 (2004).

Clark, M. Ann et al., "Exploiting M cells for drug and vaccine delivery," Advanced Drug Delivery Reviews, vol. 50:81-106 (2001).

Clonetech.com—pIRES2-DsRed2 Vector Information, PT3663-5, Catalog #6990-1, pp. 1-3 (2002).

Curiel, David T. et al., "Adenovirus enhancement of transferrin-polylysine-mediated gene delivery," Proc. Natl. Acad. Sci. USA, vol. 88:8850-8854 (1991).

D'Azzo, Alessandro et al., "Gene Transfer Strategies for Correction of Lysosomal Storage Disorders," Acta Haematol., vol. 110:71-85 (2003).

Dervan, Peter B., "Molecular Recognition of DNA by Small Molecules," Bioorganic & Medicinal Chemistry, vol. 9:2215-2235 (2001).

Desnick, Robert J. et al., "Fabry Disease, an Under-Recognized Multisystemic Disorder: Expert Recommendations for Diagnosis, Management, and Enzyme Replacement Therapy," Ann. Intern Med., vol. 138:338-346 (2003).

Donzelli, Bruno Giuliano Garisto et al., "Enhanced enzymatic hydrolysis of langostino shell chitin with mixtures of enzymes from bacterial and fungal sources," Carbohydrate Research, vol. 338:1823-1833 (2003).

Egan, William et al., "Evaluation of Polysaccharides," Characterization of Biotechnology Pharmaceutical Products. Dev. Biol. Stand., Brown, F. (Ed.), Karger, vol. 96, pp. 155-156 (1998).

Erickson, Ann H. et al., "Biosynthesis of the Lysosomal Enzyme Glucocerebrosidase," The Journal of Biological Chemistry, vol. 260:14319-14324 (1985).

Eto, Y. et al., "Treatment of lysosomal storage disorders: Cell therapy and gene therapy," J. Inherit Metab. Dis., vol. 27:411-415 (2004).

Fabrega, Sylvie et al., "Human glucocerebrosidase: heterlogous expression of active site mutants in murine null cells," Glycobiology, vol. 10(11):1217-1224 (2000).

Felgner, Philip L. et al., "Lipofection: A highly efficient, lipid-mediated DNA-transfection procedure," Proc. Natl. Acad. Sci. USA, vol. 84:7413-7417 (1987).

Fromen-Romano, Cécile et al., "Transformation of a non-enzymatic toxin into a toxoid by genetic engineering," Protein Engineering, vol. 10(10):1213-1220 (1997).

Germain, Dominiuqe P., "Fabry disease: recent advances in enzyme replacement therapy," Expert Opin. Investig. Drugs, vol. 11(10):1467-1476 (2002).

Grabowski, Gregory A., "Gaucher Disease: Lessons from a Decade of Therapy," J. Pediatr., vol. 144:S15-S19 (2004).

Hiraiwa, Masao et al., "Isolation, Characterization, and Proteolysis of Human Prosaposin, the Precursor of Saposins (Sphingolipid Activator Proteins)," Archives of Biochemistry and Biophysics, vol. 304(1):110-116 (1993).

Hong, Feng et al., "Beta-Glucan Functions as an Adjuvant for Monoclonal Antibody Immunotherapy by Recruiting Tumoricidal Granulocytes as Killer Cells," Cancer Research, vol. 63:9023-9031 (2003).

Hong, Feng et al., "Mechanism by Which Orally Administered Beta-1,3-Glucans Enhance the Tumoricidal Activity of Antitumor Monoclonal Antibodies in Murine Tumor Models," The Journal of Immunology, vol. 173:797-806 (2004).

Howell, Mark D. et al., "Limited T-cell receptor b-chain heterogeneity among interleukin 2 receptor-positive synovial T cells suggests a role for superantigen in rheumatoid arthritis," Proc. Natl. Acad. Sci. USA, vol. 88:10921-10925 (1991).

Huang, Haibin et al., "Distinct Patterns of Dendritic Cell Cytokine Release Stimulated by Fungal Beta-Glucans and Toll-Like Receptor Agonists," Infection and Immunity, vol. 77(5):1774-1781 (2009).

Huang, Haibin et al., "Robust Stimulation of Humoral and Cellular Immune Responses following Vaccination with Antigen-Loaded Beta-Glucan Particles," mBio, vol. 1(3):e00164-10, 7 pages, (2010).

Jamas, S. et al., "PGG-Glucans, A Novel Class of Macrophage-Activating Immunomodulators," Polymeric Drugs and Drug Delivery Systems, ACS Symposium Series, Chapter 5:44-51 (1991).

Jamas, S. et al., "PGG—A Novel Class of Macrophage Activating Immunomodulators," Polymer Preprints, vol. 31 (2):194-195 (1990).

Jepson, Mark A. et al., "M cell targeting by lectins: a strategy for mucosal vaccination and drug delivery," Advanced Drug Delivery Reviews, vol. 56:511-525 (2004).

Kurtzman, Aaron L. et al., "Advances in directed protein evolution by recursive genetic recombination: applications to therapeutic proteins," Current Opinion in Biotechnology, vol. 12:361-370 (2001).

Lebowitz, Jonathan H. et al., "Glycosylation-independent targeting enhances enzyme delivery to lysosomes and decreases storage in mucopolysaccharidosis type VII mice," PNAS, vol. 101(9):3083-3088 (2004).

Li, Yijun et al., "Direct Multiplex Assay of Lysosomal Enzymes in Dried Blood Spots for Newborn Screening," Clinical Chemistry, vol. 50:1785-1796 (2004).

Lozier, Jay N. et al., "Efficient Transfection of Primary Cells in a Canine Hemophilia B Model Using Adenovirus-Polylysine-DNA Complexes," Human Gene Therapy, vol. 5:313-322 (1994).

Magnelli, P. et al., "A refined method for the determination of *Saccharomyces cerevisiae* cell wall composition and beta-1,6-glucan fine structure. 1," Anal. Biochem., vol. 301(1):136-150 (2002).

Martin, Brian M. et al., "Glycosylation and Processing of High Levels of Active Human Glucocerebrosidase in Invertebrate Cells Using a Baculovirus Expression Vector," DNA, vol. 7(2):99-106 (1988).

Meikle, Peter J. et al., "Lysosomal storage disorders: emerging therapeutic options require early diagnosis," Eur. J. Pediatr, vol. 162:S34-S37 (2003).

Murphy, John E. et al., "A combinatorial approach to the discovery of efficient cationic peptoid reagents for gene delivery," Proc. Natl. Acad. Sci. USA, vol. 95:1517-1522 (1998).

Nakase, Hiroshi et al., "Biodegradable microspheres targeting mucosal immune-regulating cells: new approach for treatment of inflammatory bowel disease," J. Gastroenterl., vol. 38(Suppl. XV):59-62 (2003).

Nakase, Hiroshi et al., "Development of an Oral Drug Delivery System Targeting Immune-Regulating Cells in Experimental Inflammatory Bowel Disease: A New Therapeutic Strategy," The Journal of Pharmacology and Experimental Therapeutics, vol. 292(1):15-21 (2000).

Nakase, Hiroshi et al., "New Cytokine Delivery System Using Gelatin Microspheres Containing Interleukin-10 for Experimental Inflammatory Bowel Disease," The Journal of Pharmacology and Experimental Therapeutics, vol. 301 (1):59-65 (2002).

Neutra, Marian R., "Current Concepts in Mucosal Immunity V. Role of M cells in transepithelial transport of antigens and pathogens to mucosal immune system," Am. J. Physiol., vol. 274:C785-C791 (1998).

Niederman, Richard et al., "Enhanced neutrophil emigration and *Porphyromonas gingivalis* reduction following PGG-glucan treatment of mice," Archives of Oral Biology, vol. 47:613-618 (2002).

Niederman, R. et al., "PGG-glucan Enhances the Host Response to Periodontal Pathogens," J. Dent. Res., vol. 76:176, IADR Abstracts, Poster Presentation 1301 (1997).

NIH Guide: CNS Therapy Development for Lysosomal Storage Disorders, Department of Health and Human Services, pp. 1-12 (2004).

Novelli, Enrico M. et al., "Gene therapy for lysosomal storage disorders," Expert Opin. Biol. Ther., vol. 1(5):857-867 (2001).

Onderdonk, Andrew B. et al., "Anti-Infective Effect of Poly-beta1-6-Glucotriosyl-beta1-3-Glucopyranose Glucan In Vivo," Infection and Immunity, vol. 60(4):1642-1647 (1992).

Orvisky, Eduard et al., "Glucosylsphingosine accumulation in tissue from patients with Gaucher disease: correlation with phenotype and genotype," Molecular Genetics and Metabolism, vol. 76:262-270 (2002).

Ostroff, G.R. et al., "A New Beta-Glucan-Based Macrophage-Targeted Adjuvant," Polymeric Drugs and Drug Delivery Systems, ACS Symposium Series, Chapter 6:52-59 (1991).

Ostroff, G.R. et al., "Macrophage-Targeted Polysaccharide Microcapsules for Antigen and Drug Delivery," Polymer Preprints, vol. 31(2):200-201 (1990).

Ostroff, G.R. et al., "Molecular Cloning with Bifunctional Plasmid Vectors in *Bacillus subtilis*, I. Construction and Analysis of *B. subtilis* Clone Banks in *Escherichia coli*," Mol. Gen. Genet., vol. 193:299-305 (1984).

Ostroff, G.R. et al., "Molecular Cloning with Bifunctional Plasmid Vectors in *Bacillus subtilis*, II. Transfer of Sequences Propagated in *Escherichia coli* to *B. subtilis*," Mol. Gen. Genet., vol. 193:306-311 (1984).

Ostroff, G.R. et al., "Molecular Cloning with Bifunctional Plasmid Vectors in *Bacillus subtilis*: Isolation of a Spontaneous Mutant of *Bacillus subtilis* with Enhanced Transformability for *Escherichia coli*-Propagated Chimeric Plasmid DNA," Journal of Bacteriology, vol. 156(2):934-936 (1983).

Ostroff, Gary et al., "Potential for Beta 1,3-Glucans to Prevent and Treat Biological Warfare Infections," BTR2003: Unified Science & Technology for Reducing Biological Threats and Countering Terrorism, 13 pages (2002).

pIRES-EGFP, Vector Information, GenBank Accession #: Submission in Progress, PT3157-5, Clontech Laboratories, Inc., (1997).

Reichner, Jonathan S. et al., "Receptor-mediated phagocytosis of rat macrophages is regulated differentially for opsonized particle and non-opsonized particles containing b-glucan," Immunology, vol. 104:198-206 (2001).

Ribeiro, C.C. et al., "Calcium phosphate-alginate microspheres as enzyme delivery matrices," Biomaterials, vol. 25:4363-4373 (2004).

Selitrennikoff, Claude P. et al., "Emerging therapeutic cell wall targets in fungal infections," Emerging Therapeutic Targets, vol. 3(1):53-72 (1999).

Shetty, K. et al., "Gene therapy of hepatic diseases: prospects for the new millennium," Gut, vol. 46:136-139 (2000).

Simon, Ethan S. et al., "Preparation of Cytidine 5'-Monophospho-N-Acetylneuraminic Acid and Uridine 5'-Diphosphoglucuronic Acid; Syntheses of alpha-2, 6-Sialyllactosamine, alpha-2, 6-Sialyllactose, and Hyaluronic Acid," Methods in Enzymology, vol. 179:275-287 (1989).

Sleeper, M.M. et al., "Gene Therapy Ameliorates Cardiovascular Disease in Dogs With Mucopolysaccharidosis VII," Circulation, vol. 110:815-820 (2004).

Soto, Ernesto et al., "Glucan Particle Encapsulated Rifampicin for Targeted Delivery to Macrophages," Polymers, vol. 2:681-689 (2010).

Soto, E. et al., "Glucan Particles as an Efficient siRNA Delivery Vehicle," Nanotech 2008, vol. 2, Chapter 4, pp. 332-335 (2008).

Soto, Ernesto R. et al., "Glucan Particles for Macrophage Targeted Delivery of Nanoparticles," Journal of Drug Delivery, vol. 2012, 13 pp. (2011).

Soto, E. et al., "Oral Macrophage Mediated Gene Delivery System," NSTI-Nanotech, vol. 2:378-381 (2007).

Soto, Ernesto R. et al., "Yeast Cell Wall Particles as a Versatile Macromolecular Delivery System," Polymeric Materials: Science & Engineering, vol. 98:591-593 (2008).

Stashenko, P. et al., "Reduction of Infection-stimulated Periapical Bone Resorption by the Biological Response Modifier PGG Glucan," J. Dent. Res., vol. 74(1):323-330 (1995).

Tesz, Gregory J. et al., "Glucan particles for selective delivery of siRNA to phagocytic cells in mice," Biochem. J., vol. 436:351-362 (2011).

Trubetskoy, Vladimir S. et al., "Quantitative Assessment of DNA Condensation," Analytical Biochemistry, vol. 267:309-313 (1999).

Trubetskoy, V.S. et al., "Recharging cationic DNA complexes with highly charged polyanions for in vitro and in vivo gene delivery," Gene Therapy, vol. 10:261-271 (2003).

Tsuji, Shojl et al., "Signal sequence and DNA-mediated expression of human lysosomal a-galactosidase A," Eur. J. Biochem., vol. 165:275-280 (1987).

Uematsu, T. et al., "Increased Infection Resistance in PGG-glucan-Treated ICAM-1 Deficient Mice," J. Dent. Res., vol. 76:176, IADR Abstracts, Poster Presentation 1302 (1997).

Van Der Lubben, I.M. et al., "Transport of Chitosan Microparticles for Mucosal Vaccine Delivery in a Human Intestinal M-cell Model," Journal of Drug Targeting, vol. 10(6):449-456 (2002).

Vetvicka, Vaclav et al., "Pilot Study: Orally-Administered Yeast Beta1,3-glucan Prophylactically Protects Against Anthrax Infection and Cancer in Mice," JANA, vol. 5(2):5-9 (2002).

Wilcox, William R., "Lysosomal Storage Disorders: The Need for Better Pediatric Recognition and Comprehensive Care," J. Pediatr., vol. 144:S3-S14 (2004).

Williams, William V. et al., "Restricted Heterogeneity of T Cell Receptor Transcripts in Rheumatoid Synovium," J. Clin. Invest., vol. 90:326-333 (1992).

Wilson, H.M. et al., "Targeting Genetically Modified Macrophages to the Glomerulus," Nephron Exp. Nephrol., vol. 94:e113-e118 (2003).

Wu, George Y., et al., "Receptor-mediated in Vitro Gene Transformation by a Soluble DNA Carrier System," The Journal of Biological Chemistry, vol. 262(10):4429-4432 (1987).

Young, Shih-Houng et al., "A Comparison of the Pulmonary Inflammatory Potential of Different Components of Yeast Cell Wall," Journal of Toxicology and Environmental Health, Part A, vol. 70:1116-1124 (2007).

Zhao, H. et al., "Protein Glycoengineering," Journal of Chinese Biotechnology, vol. 23(9):18-20 (2003).

Zimmerman, Janet W. et al., "A Novel Carbohydrate-Glycosphingolipid Interaction between a b-(1-3)-Glucan Immunomodulator, PGG-glucan, and Lactosylceramide of Human Leukocytes," The Journal of Biological Chemistry, vol. 273(34):22014-22020 (1998).

Japanese Office Action for Application No. 2007-516687, pp. 1-4, dated Sep. 28, 2011.

Australian Office Action for Application No. 2005284727, dated Apr. 13, 2010.

Chinese Office Action for Application No. 200580037576.4, dated Mar. 23, 2010.

International Search Report for Application No. PCT/US2005/021161, dated Jul. 25, 2006.

International Search Report for Application No. PCT/US2005/033300.

First Office Action, Chinese Application for Invention No. 200580037576.4, and English translation as provided by the Chinese foreign asssociate.

Indian Office Action for Application No. 163/KOLNP/2007, dated Apr. 26, 2011.

* cited by examiner

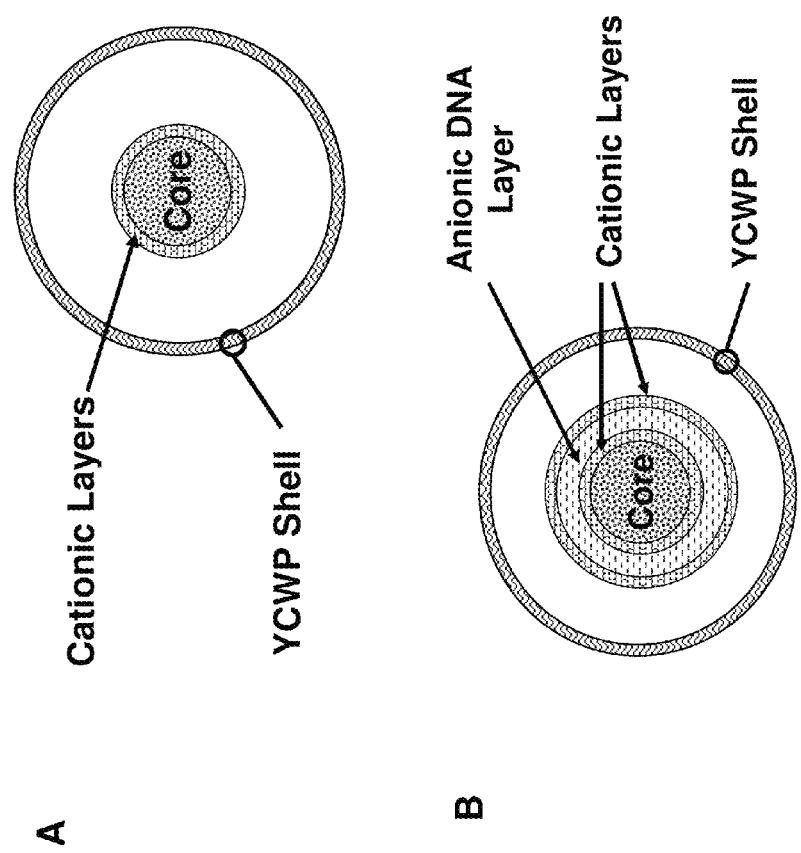
Figure 1 a-b

Figure 10 a-c

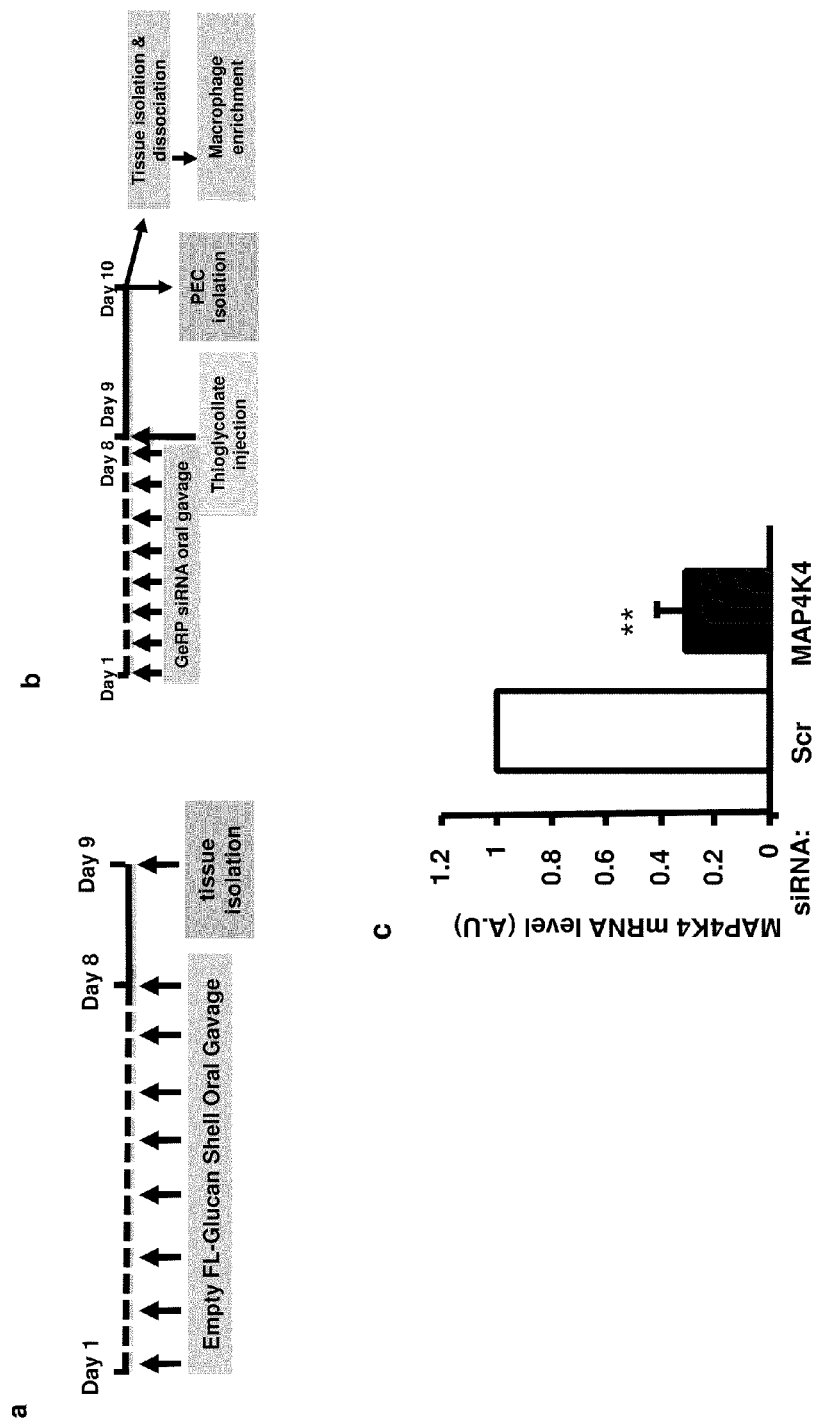
Figure 20a-c

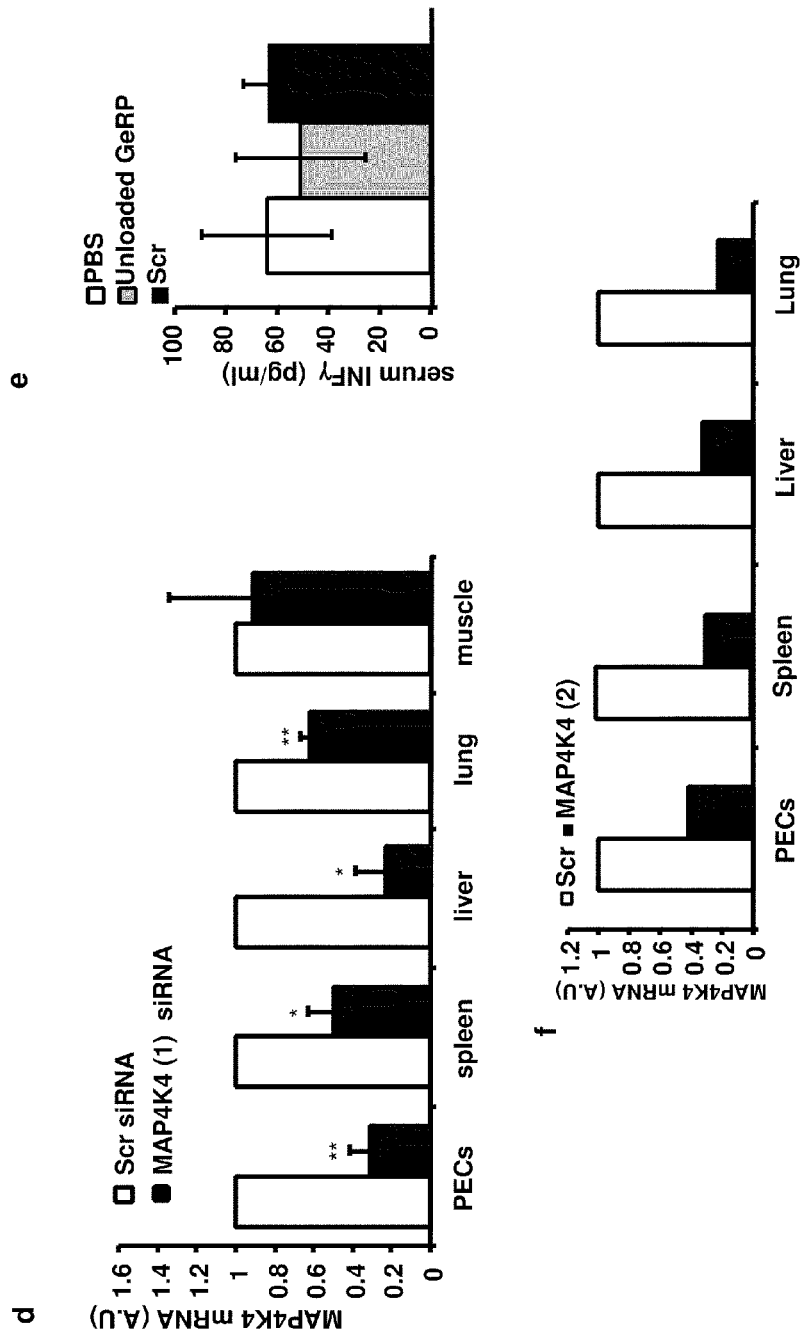
Figure 20d-f

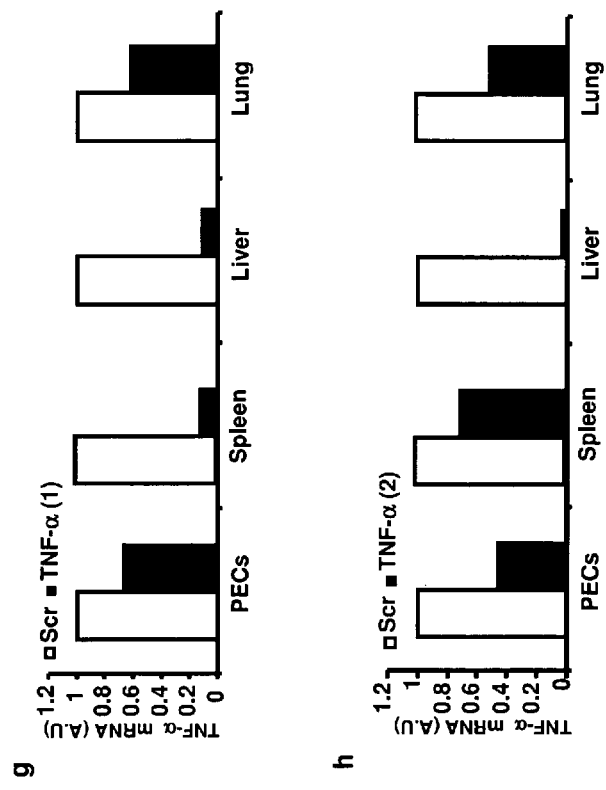
Figure 20g-h

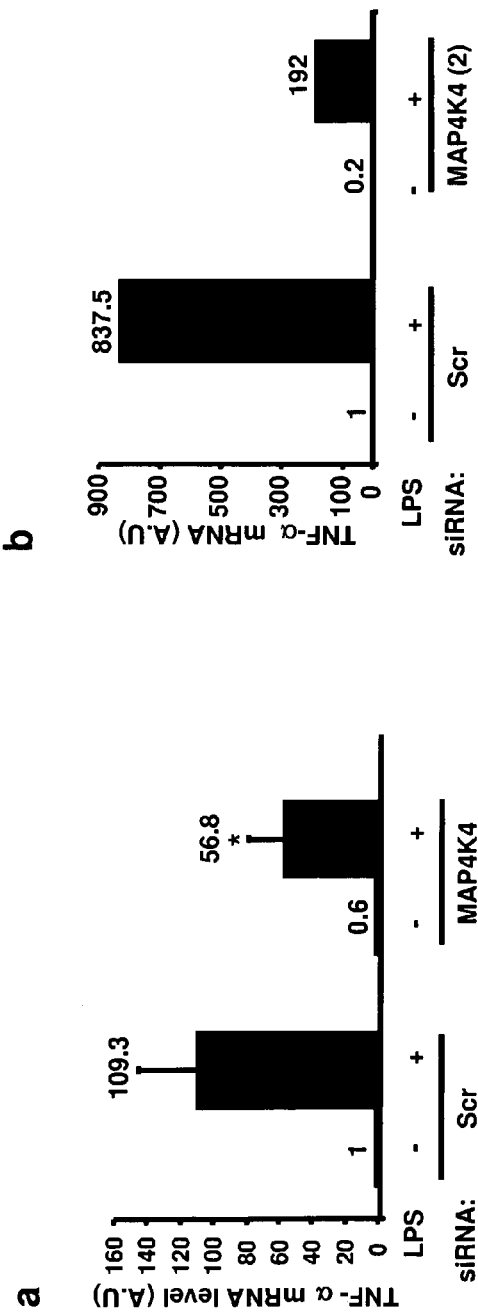
Figure 24a-b

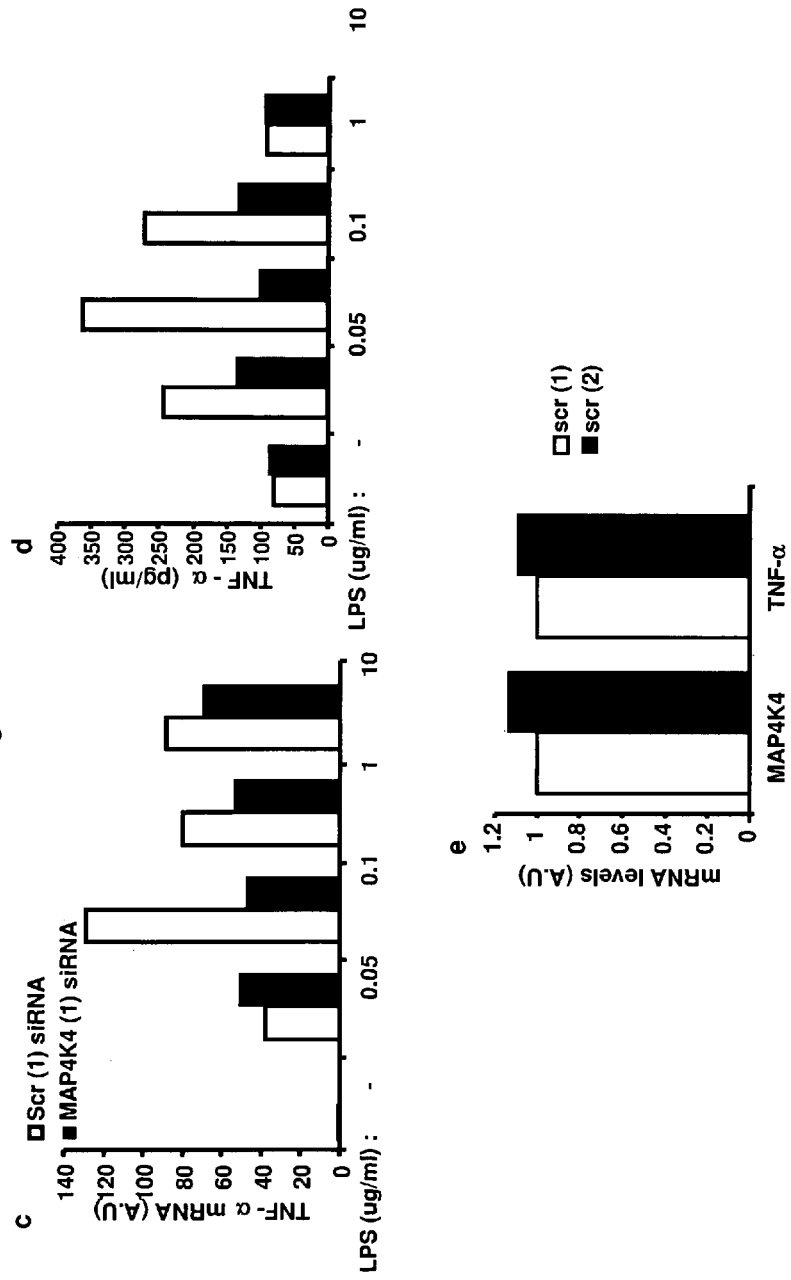
Figure 24c-e

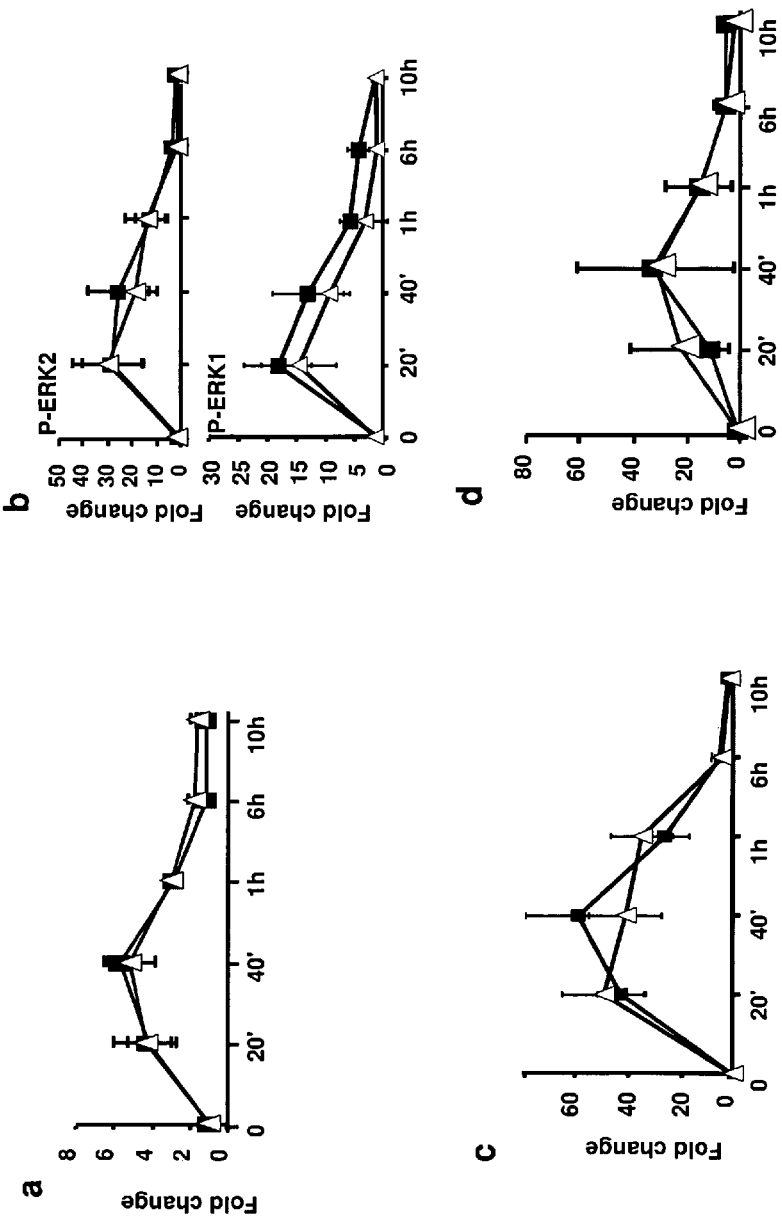
Figure 27 a-d

Figure 27 e-g
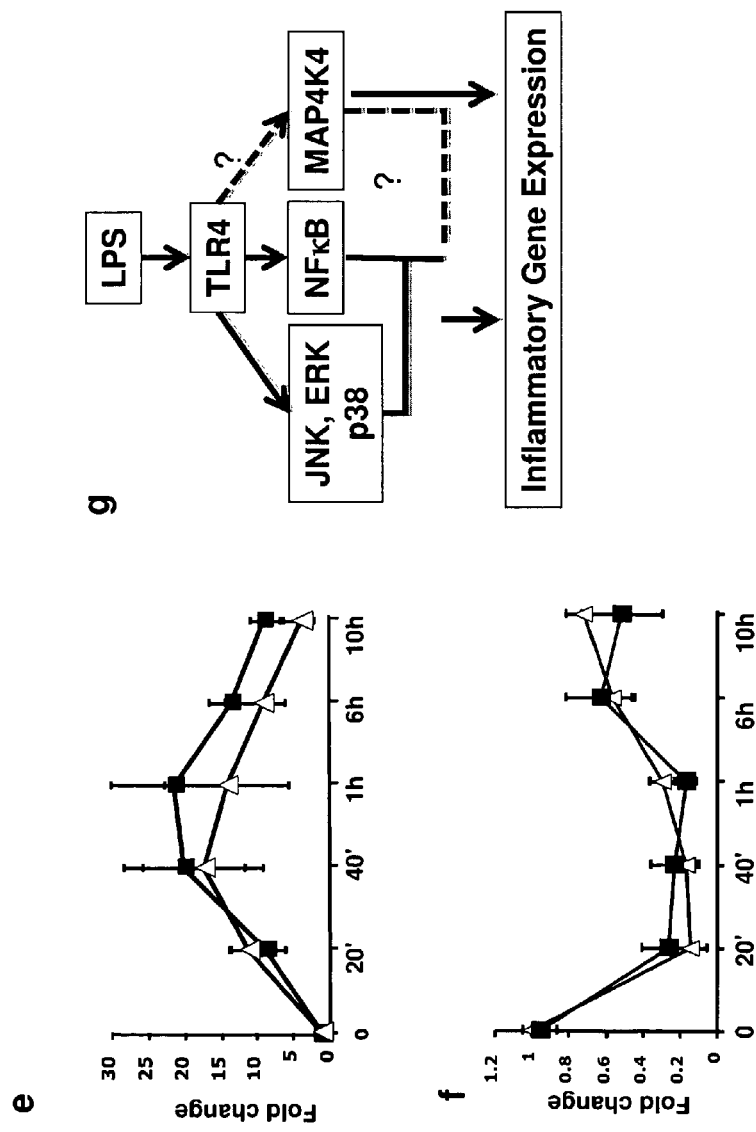

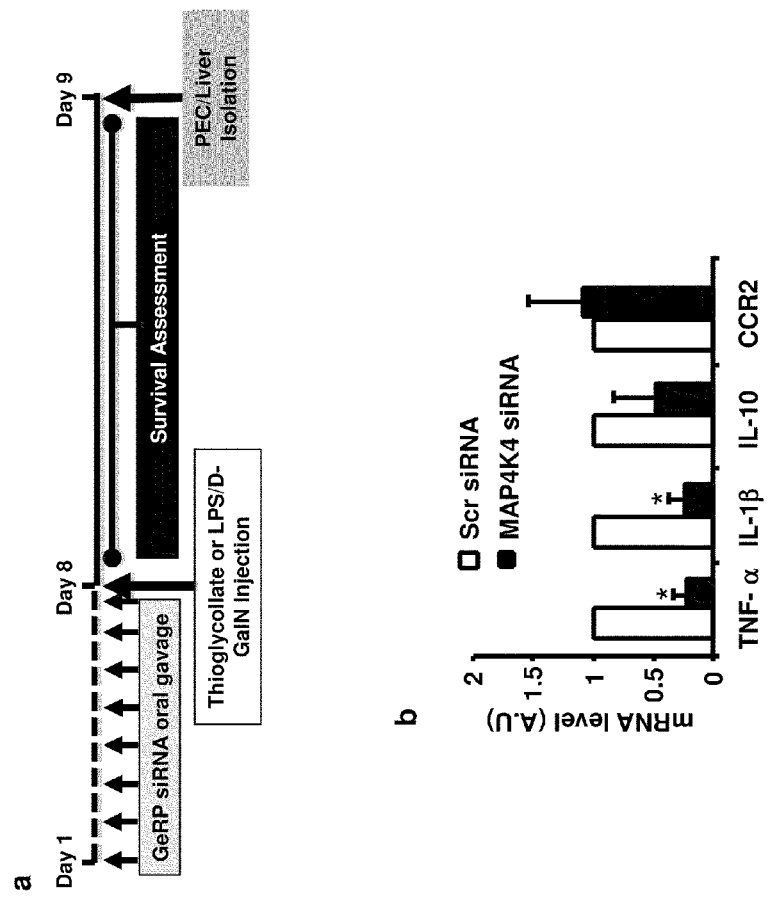
Figure 28 a-b

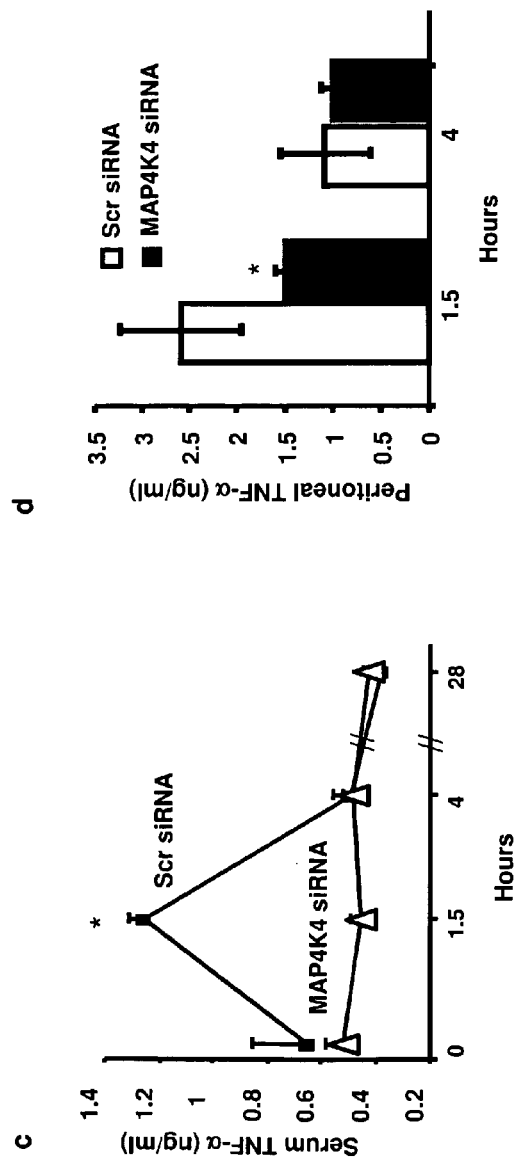
Figure 28 c-d

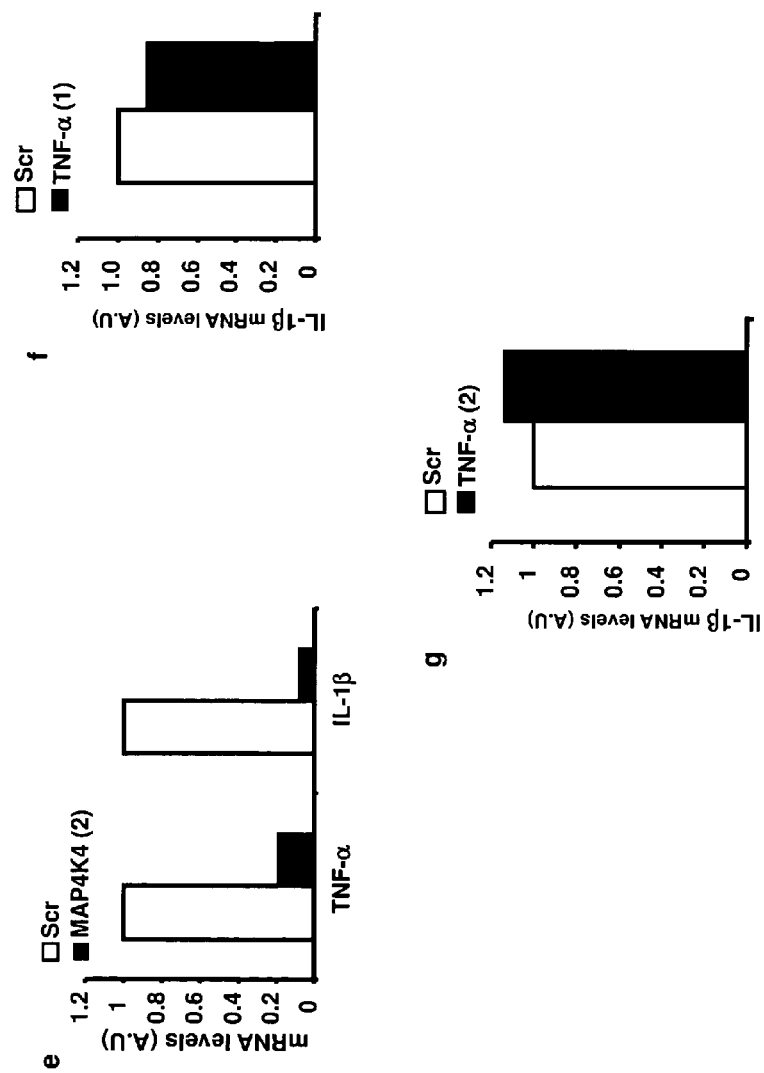
Figure 28e-g

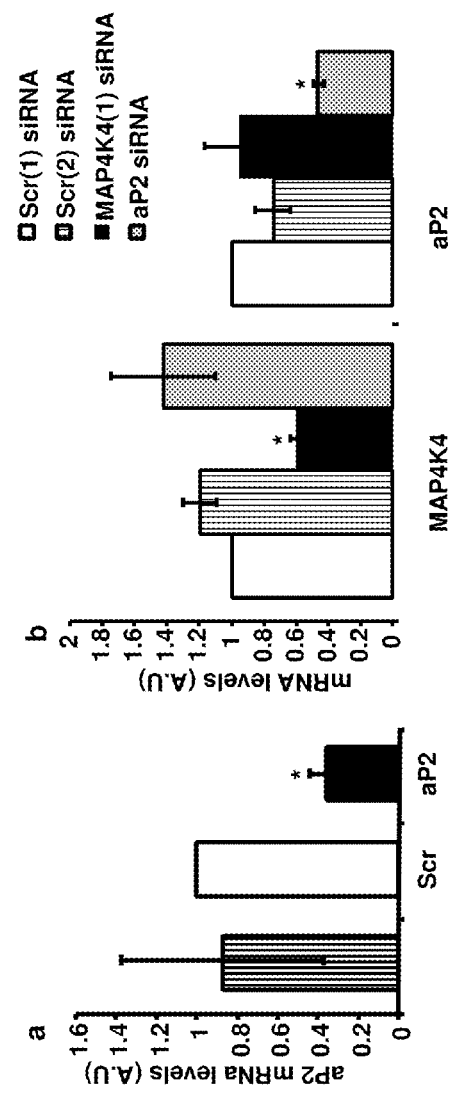
Figure 36a-b

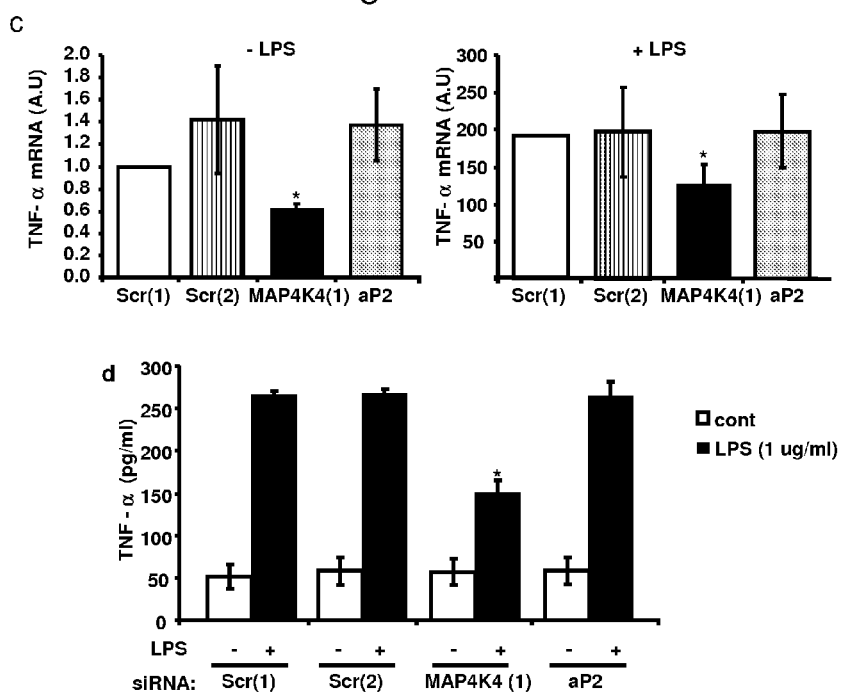

ENCAPSULATED NANOPARTICLES FOR NUCLEIC ACID DELIVERY

STATEMENT OF FEDERALLY SPONSORED RESEARCH

This invention was made with Government support under grant no. DK030648 awarded by the National Institutes of Health. The government has certain rights in the invention.

BACKGROUND OF THE INVENTION

RNA interference (RNAi) is the mechanism of sequence-specific, post-transcriptional gene silencing initiated by double-stranded RNAs (dsRNA) homologous to the gene being suppressed. dsRNAs are processed by Dicer, a cellular ribonuclease III, to generate duplexes of about 21 nt with 3'-overhangs (small interfering RNA, siRNA) which mediate sequence-specific mRNA degradation. In mammalian cells siRNA molecules are capable of specifically silencing gene expression without induction of the unspecific interferon response pathway. Thus, siRNAs have become a new and powerful alternative to other genetic tools such as antisense oligonucleotides and ribozymes to analyze gene function. Moreover, siRNAs are being developed for therapeutic purposes with the aim of silencing disease genes in humans.

A key problem in the development of effective gene therapy techniques is the delivery of nucleic acids to cells in vivo. The formation of stable complexes between negatively charged genetic material and cationic polymers is the most commonly studied approach to develop non-viral delivery agents. The work of several groups has focused on synthesizing and characterizing a range of cationic polymers to provide good DNA condensation necessary to prevent degradation of the genetic material in negatively charged nanoparticles capable of DNA delivery into cells. Once inside the cells, these nanocomplexes should be capable of releasing DNA, and the toxicity of the free cationic polymer must be minimal. Polyethylenimine (PEI) has proven to be one of the best cationic polymers for nanocomplex formation with DNA and provides good transfection efficiencies; however PEI is toxic to cells, thus limiting the concentration range that can be used. The goal of producing delivery agents that are non-toxic, capable of efficiently protecting DNA and delivering DNA to the interiors of cells has proven challenging, and an ideal gene delivery system remains elusive.

SUMMARY OF THE INVENTION

Methods and compositions for delivering payload molecules, including nucleic acids, have been created using yeast cell wall particles. Embodiments of the invention are useful for delivering a variety of molecules to cells. Aspects of the invention include yeast cell wall particles encapsulating nanoparticles comprising payload molecules.

In one aspect, the present invention features a payload delivery system which includes an exterior and a core, the core comprising a payload complexed with a trapping agent. In another aspect, the payload delivery system includes an exterior and a multilayered interior, wherein the interior has a core comprising a core agent and a trapping agent, at least one payload layer, and at least one trapping layer. In a related aspect, the present invention features a payload delivery system made up of a yeast cell wall particle (YCWP) exterior and a multilayered nanoparticle interior, wherein the multilayered nanoparticle interior has a core comprising a payload complexed with a trapping agent. In another related aspect, the delivery system is made up of a YCWP exterior and a multilayered nanoparticle interior, wherein the multilayered nanoparticle interior has a core comprising a core agent and a trapping agent, at least one payload layer, and at least one trapping layer. In some embodiments, the core agent is a payload agent. In some embodiments, the payload delivery system has at least a second payload layer and trapping layer. In further embodiments, the payload delivery system has third, fourth, fifth, or more payload layers and/or trapping layers. In certain embodiments, the exterior is yeast glucan particle (YGP). In other embodiments, the exterior is a yeast glucan mannan particle (YGMP).

In certain aspects of the invention, the payload layers and trapping layers of the payload delivery system of the invention are associated by electrostatic interactions. In other aspects, the core and trapping agents of the payload delivery system of the invention are associated by electrostatic interactions. In some embodiments, the core comprises an anionic agent and a cationic agent, e.g., a cationic trapping agent, complexed such that the core is cationic on the surface. In some embodiments, the core is coated with a trapping layer, e.g., a cationic trapping layer. In some embodiments, the trapping layer coating the core and/or payload layers is cationic. In related embodiments, the core and/or trapping layers comprise a cationic polymer, a cationic detergent or a mixture thereof. In a further embodiment, the cationic polymer may include chitosan, poly-L-lysine and polyethylenimine (PEI), or derivatives thereof. In a related embodiment, the cationic polymer of these aspects may include a protein, a polypeptide, a short synthetic peptide, a helical amphiphilic peptide, a cationic dendrimers, glucaramide polymer, a N-substituted glycine oligomer, poly(2-methyl-acrylic acid 2-[(2-dimethylamino)-ethyl)-methyl-amino]-ethyl-1 ester), poly(2-dimethylamino ethyl)-methacrylate and mixtures thereof. In an exemplary embodiment, the cationic polymer is polyethylenimine (PEI).

In alternative embodiments, the core comprises a cationic agent and an anionic agent, e.g., an anionic trapping agent, complexed such that the core is anionic on the surface. In some embodiments, the core is coated with a trapping layer, e.g., an anionic trapping agent. In some embodiments, the trapping layer coating the core and/or payload layers is anionic. In related embodiments, the core and/or trapping layers comprise an anionic polymer, an anionic detergent or a mixture thereof. In a further embodiment, the anionic polymer is an alginate or a xanthan. In another aspect, the core, payload and/or trapping layers of the payload delivery system of the invention are associated by hydrophobic interactions, Van der Waals interactions, and/or physical interactions.

In various aspects of the invention, the payload is a DNA, an RNA, a protein, a small molecule, or a mixture thereof. In one aspect, the payload delivery system is a nucleic acid delivery system, wherein the payload layer is made up of nucleic acid molecules. In one embodiment of this aspect, the nucleic acid is a DNA or an RNA, or a mixture thereof. In a further embodiment, the nucleic acid molecule is an oligonucleotide, an antisense molecule, a siRNA, a shRNA, a siRNA or shRNA expression vector, an enzymatic RNA, a recombinant DNA, an expression vector, an antisense DNA, or mixtures thereof.

In another aspect of the invention, the payload delivery system or nucleic acid delivery system of the invention features a core that is a payload core, which additionally comprises a payload. In one embodiment of this aspect, the payload core has a payload which is a nucleic acid molecule, a protein, a small molecule, or a mixture thereof. In a further embodiment, the nucleic acid molecule is a DNA or an RNA.

In one embodiment, the nucleic acid molecule is an oligonucleotide, an antisense molecule, a siRNA, a shRNA, a siRNA or shRNA expression vector, an enzymatic RNA, a recombinant DNA, an expression vector, or mixtures thereof. In one aspect, the payload core and the payload layer comprise the same payload. In an alternative aspect, the payload core and the payload layer comprise distinct payloads. In some embodiments, the core is a nanoplexed core.

In another aspect, the payload delivery systems or nucleic acid delivery systems of the invention further feature a core containing a biocompatible agent. In one embodiment, the biocompatible agent is a nucleic acid, a protein, a biopolymer, an inorganic salt, or mixtures thereof. In an exemplary embodiment the biocompatible agent is a nucleic acid, e.g., transfer RNA (tRNA). In another embodiment, the biocompatible core includes magnetic material. In another aspect, the YCWP of the payload or nucleic acid delivery systems of the invention has been modified, e.g., chemically modified, to contain a cell or tissue specific targeting agent.

In another aspect, the present invention features a method of delivering a payload to a phagocytic cell involving contacting the cell with the payload delivery system under conditions facilitating phagocytosis of the payload delivery system, such that delivery of the payload occurs. In one embodiment of this aspect, the phagocytic cell is selected from the group consisting of a monocyte, a neutrophil and a dendritic cell. In another embodiment, the phagocytic cell is a macrophage. In another aspect, the present invention features a method of delivering a payload to a non-phagocytic cell, involving contacting a phagocytic cell with a payload delivery system of the invention under conditions facilitating phagocytosis of the payload delivery system, such that delivery of all or a portion of the system occurs under conditions facilitating transfer (e.g., secondary transfer) of a portion of the delivery system (e.g., a payload-comprising portion) to the second (e.g., the non-phagocytic) cell.

In another aspect, the present invention features a method of making a payload delivery system, involving contacting a YCWP with at least the core components under conditions facilitating formation of the core. Optionally, the core-containing YCWP can be contacted with a trapping component under conditions facilitating formation of a trapping layer covering the core. In some embodiments, the core components comprise one or more payload components. In some embodiments, the core components are non-payload components. In some embodiments, the core-containing YCWP can be contacted with a payload component, under conditions facilitating formation of at least one payload layer; and a trapping component, under conditions facilitating formation of at least one trapping layer, under conditions such that the payload delivery system is formed. In exemplary embodiments, the system is made using a layer-by-layer (LbL) approach.

In another aspect, the present invention features a method of treating a disease or disorder, involving administering to a subject in need thereof a payload delivery system of the invention, under conditions facilitating delivery of the payload, such that the disease or disorder is treated. In one embodiment of this aspect, the disease or disorder is an inflammatory disease or disorder. In another embodiment, the disease or disorder is selected from the group consisting of an autoimmune disorder, sepsis, an intestinal disorder, an infectious disease, a malignancy, a pulmonary disorder, a cardiac disorder, and a neurological disorder. In another embodiment, the disease or disorder is selected from the group consisting of Crohn's disease, HIV, arthritis, cardiovascular disease and cancer. In another embodiment, the disease or disorder is a metabolic disease or disorder. In a further embodiment, the disease or disorder is selected from the group consisting of glucose tolerance, insulin sensitivity, diabetes and obesity. In various embodiments of these aspects, the payload delivery system is administered parenterally, subcutaneously (s.c.), and/or intraperitoneally (i.p.). In one embodiment of these aspects, the payload delivery system is administered orally. In another embodiment, the payload delivery system is administered systemically. In yet another embodiment, the payload delivery system is administered locally. In some embodiments, the payload delivery system is administered by injection.

In one aspect, the present invention features a method of oral drug delivery, involving administering to a subject a payload delivery system of the invention. In another aspect, the present invention features a method of oral drug delivery, involving administering to a subject a payload delivery system of the invention under conditions facilitating contact of the payload delivery system with macrophages in the subject, such that the payload is delivered to the macrophages. In another aspect, the present invention features a macrophage-mediated payload delivery method, involving contacting a macrophage with the payload delivery system of the invention under conditions facilitating phagocytosis of the payload delivery system, such that delivery of the payload occurs. In one embodiment, the macrophage is contacted in vitro. In another embodiment, the macrophage is contacted in vivo.

In one aspect, the present invention features a siRNA delivery system which includes an exterior and a core, the core comprising a siRNA complexed with a trapping agent. In another aspect, the siRNA delivery system includes an exterior and a multilayered interior, wherein the multilayered interior has a core comprising a core agent and a trapping agent, at least one siRNA layer, and at least one trapping layer. In another aspect, the siRNA delivery system includes an exterior and an interior core comprising a core agent and at least one siRNA. In one aspect, the present invention features a siRNA delivery system made up of a yeast cell wall particle (YCWP) exterior and a multilayered nanoparticle interior, wherein the multilayered nanoparticle interior has a core comprising a siRNA complexed with a trapping agent. In another related aspect, the siRNA delivery system is made up of a YCWP exterior and a multilayered nanoparticle interior, wherein the multilayered nanoparticle interior has a core comprising a core agent and a trapping agent, at least one siRNA layer, and at least one trapping layer. In some embodiments, the core agent is a siRNA. In some embodiments, the siRNA delivery system has at least a second siRNA and trapping layer. In further embodiments, the siRNA delivery system has third, fourth, fifth, or more siRNA layers and/or trapping layers. In certain embodiments, the exterior is a yeast glucan particle (YGP). In other embodiments, the exterior is a yeast glucan mannan particle (YGMP).

In certain aspects of the invention, the payload layers and trapping layers of the siRNA delivery system of the invention are associated by electrostatic interactions. In other aspects, the core and trapping agents of the siRNA delivery system of the invention are associated by electrostatic interactions. In some embodiments, the core comprises a siRNA and a cationic agent, e.g., a cationic trapping agent, complexed such that the core is cationic on the surface. In some embodiments, the core is coated with a trapping layer, e.g., a cationic trapping layer. In some embodiments, the trapping layer coating the core and/or siRNA layers is cationic.

In one aspect, the siRNA delivery system of the invention contains a Map4k4 siRNA, i.e., a siRNA targeting Map4k4. In another aspect, the siRNA delivery system contains an inflammatory cytokine siRNA, i.e., a siRNA targeting an inflammatory cytokine. In yet another aspect, the siRNA delivery system of the invention contains a TNFα siRNA. In another aspect, the siRNA is a RIP140 siRNA. In another aspect, the siRNA is a TLR4 signaling siRNA. In another aspect, the siRNA is an TNF-α siRNA.

In another aspect, the siRNA delivery system of the invention features a core that is a payload core which additionally comprises a payload. In one embodiment, the payload is a siRNA. In a further embodiment, the payload core and payload layer comprise the same siRNA. In an alternative embodiment, the payload core and payload layer comprise different siRNAs. In some embodiments, the siRNA delivery system contains between about $1 \times 10^{-7}$ to $10 \times 10^{-7}$ pmols of siRNA per YCWP. In some embodiments, the siRNA delivery system contains between about $0.1 \times 10^{-7}$ to $100 \times 10^{-7}$ pmols of siRNA per YCWP. In an exemplary embodiment, the siRNA delivery system contains $4 \times 10^{-7}$ pmols of siRNA per YCWP. In an exemplary embodiment, the siRNA delivery system contains siRNA present at a ratio of about 4 µg siRNA per milligram of YCWP. In another embodiment of this aspect, the payload is a non-siRNA payload. In one embodiment, the non-siRNA payload is a DNA, a protein, a non-siRNA RNA, an antisense DNA, or a small molecule. In a further embodiment, the DNA is an expression vector. In some embodiments, the core is a nanoplexed core.

In another aspect, the trapping layer of the siRNA delivery system of the invention contains a charged polymer, a charged detergent, and/or a mixture thereof. In one embodiment of this aspect, the trapping layer is made up of a cationic polymer, a cationic detergent or a mixture thereof. In a related aspect, the core contains a charged polymer, a charged detergent, and/or a mixture thereof. In one embodiment of this aspect, the core is made up of a cationic polymer, a cationic detergent or a mixture thereof. In a further embodiment, the cationic polymer of these aspects may include chitosan, poly-L-lysine and polyethylenimine (PEI), or derivatives thereof. In a related embodiment, the cationic polymer of these aspects may include a protein, a polypeptide, a short synthetic peptide, a helical amphiphilic peptide, a cationic dendrimers, glucaramide polymer, a N-substituted glycine oligomer, poly (2-methyl-acrylic acid 2-[(2-dimethylamino)-ethyl]-methylamino]-ethyl-1 ester), poly(2-dimethylamino ethyl)-methacrylate and mixtures thereof. In an exemplary embodiment, the cationic polymer is polyethylenimine (PEI). In some embodiments, siRNA delivery system comprises one or more additional payload layers. Depending on the nature of the additional payloads, associated trapping layers and/or the core layer can made up of cationic polymers, detergents, or mixtures thereof, or anionic polymers, detergents, or mixtures thereof (e.g., alginate or xanthan). In other aspects, the payload layers and trapping layers are associated by hydrophobic interactions, Van der Waals interactions, and/or physical interactions. Additional aspects of the invention feature siRNA delivery systems without trapping layers.

In another aspect, the siRNA delivery systems of the invention further features a core containing a biocompatible agent. In one embodiment, the biocompatible agent is a nucleic acid, a protein, a biopolymer, an inorganic salt, or mixtures thereof. In an exemplary embodiment the biocompatible agent is a nucleic acid, e.g., transfer RNA (tRNA). In another embodiment, the biocompatible core includes magnetic material. In another aspect, the YCWP of the siRNA delivery systems of the invention additionally has a coat layer containing a cell or tissue specific targeting agent.

In another aspect, the siRNA delivery system of the invention contains payload nucleic acid at a ratio of between about $1 \times 10^{-7}$ to $10 \times 10^{-7}$ pmol siRNA per YCWP. In another aspect, the siRNA delivery system of the invention contains payload nucleic acid at a ratio of between about $0.1 \times 10^{-7}$ to $100 \times 10^{-7}$ pmol siRNA per YCWP. In another aspect, the siRNA delivery system of the invention contains payload nucleic acid at a ratio of between about $0.01 \times 10^{-7}$ to $1000 \times 10^{-7}$ pmol siRNA per YCWP. In one embodiment of this aspect, the payload nucleic acid is present at a ratio of 4 µg per milligram of YCWP particles. In one embodiment, the nucleic acid may be a siRNA, a shRNA, or a DNA.

In one aspect, the present invention features a method of delivering an siRNA to a phagocytic cell, involving contacting the cell with an siRNA delivery system of the invention under conditions facilitating phagocytosis of the siRNA delivery system, such that delivery of the siRNA occurs. In one embodiment of this aspect, the phagocytic cell is selected from the group consisting of a monocyte, a neutrophil and a dendritic cell. In another embodiment, the phagocytic cell is a macrophage. In another aspect, the present invention features a method of delivering an siRNA to a non-phagocytic cell, involving contacting a phagocytic cell with an siRNA delivery system of the invention under conditions facilitating phagocytosis of the siRNA delivery system, such that delivery of all or a portion of the system occurs under conditions facilitating transfer (e.g., secondary transfer) of a portion of the delivery system (e.g., a payload-comprising portion) to the second (e.g., the non-phagocytic) cell.

In another aspect, the present invention features a method of making a siRNA delivery system, involving contacting a YCWP with at least the core components under conditions facilitating formation of the core. Optionally, the core-containing YCWP can be contacted with a trapping component under conditions facilitating formation of a trapping layer covering the core. In some embodiments, the core components comprise a siRNA. In some embodiments, the core components are non-siRNA components. In some embodiments, the core-containing YCWP can be contacted with a siRNA, under conditions facilitating formation of at least one siRNA layer; and a trapping component, under conditions facilitating formation of at least one trapping layer, under conditions such that the siRNA delivery system is formed. In exemplary embodiments, the system is made using a layer-by-layer (LbL) approach. In other exemplary embodiments, the core-containing YCWP can be contacted with a siRNA, under conditions facilitating formation of at least one siRNA layer, such that the siRNA delivery system is formed without a trapping layer.

In another aspect, the present invention features a method of treating a disease or disorder, involving administering to a subject in need thereof a siRNA-delivery system of the invention, under conditions facilitating delivery of the payload, such that the disease or disorder is treated. In one embodiment of this aspect, the disease or disorder is an inflammatory disease or disorder. In another embodiment, the disease or disorder is selected from the group consisting of an autoimmune disorder, sepsis, an intestinal disorder, an infectious disease, a malignancy, a pulmonary disorder, a cardiac disorder, an inflammatory disorder and a neurological disorder. In another embodiment, the disease or disorder is selected from the group consisting of Crohn's disease, HIV, arthritis, cardiovascular disease and cancer. In another embodiment, the disease or disorder is a metabolic disease or disorder. In a further embodiment, the disease or disorder is selected from the group consisting of glucose tolerance, insulin sensitivity, diabetes and obesity. A related aspect features a method of treating a TLR4-mediated disease or disorder, involving administering to a subject in need thereof a siRNA-delivery system of the invention, wherein the payload is an siRNA that targets a TLR4 signaling component, under conditions facilitating delivery of the siRNA and modulation of TLR4 signaling, such that the disease or disorder is treated. In various embodiments of these aspects, the siRNA delivery system is administered topically, parenterally, and/or enterally. In exemplary embodiments, the siRNA delivery system is administered orally. In some embodiments, the siRNA is delivered systemically. In yet other embodiments, the siRNA is delivered locally.

Accordingly, in one aspect, the invention features a method of oral drug delivery, involving administering to a subject a siRNA delivery system of the invention. In one embodiment of this aspect, the amount of siRNA administered to a subject using the methods of the invention is between about 0.1-100 μg/kg. In another embodiment, the amount of siRNA administered to a subject using the methods of the invention is between about 1-10 μg/kg. In another embodiment, the amount of siRNA administered to a subject using the methods of the invention is between about 0.01-1000 μg/kg. While not wishing to be bound in theory, a surprising aspect of the siRNA delivery systems of the invention is the high efficiency of siRNA delivery. Accordingly, these delivery systems provide advantages of lower cost and toxicity associated therewith. By contrast, the siRNA delivery systems are believed to be capable of delivering high amounts of siRNAs, for example, up to 100,000 μg/kg, if desired.

In another aspect, the invention features a method of oral drug delivery, involving administering to a subject a siRNA delivery system of the invention under conditions facilitating contact of the siRNA drug delivery system with macrophages in the subject, such that the siRNA is delivered to the macrophages. In another aspect, the present invention features a macrophage-mediated siRNA delivery method, involving contacting a macrophage with the siRNA delivery system of the invention under conditions facilitating phagocytosis of the siRNA delivery system, such that delivery of the siRNA occurs. In one embodiment, the macrophage is contacted in vitro. In another embodiment, the macrophage is contacted in vivo.

BRIEF DESCRIPTION OF THE DRAWINGS

FIGS. 10b and 10c, direct mRNA measurement).

FIG. 19a shows a timeline of i.p. treatment with siRNA formulations and PEC isolation. 10 week-old C57BL6/J male mice received one daily i.p injection of FITC-GeRPs containing Scr or MAP4K4 siRNA (10 ug/kg) coupled to Dy547 for the first 3 days. On day 4, the mice were i.p. injected with thioglycollate and PECs were isolated on day 5. FIG. 19b shows RT-PCR analysis of MAP4K4 mRNA expression. Results are expressed in arbitrary units and are the mean±SEM of four independent experiments. * p<0.001.

FIG. 20 shows the protocols and results for studies of the uptake of orally administered FL glucan particles (YCWPs) by macrophages in vivo and the ability of GeRPs to suppress gene expression in vivo. FIGS. 20 a-b show treatment protocol and sample collection timelines. FIG. 20c shows an analysis of MAP4K4 expression in PECs analysed by RT-PCR after treatment with MAP4K4 siRNA (1) according to the protocol of FIG. 20b. Using data from a subsequent experiment, FIG. 20d shows additional analysis of MAP4K4 expression in PECs and adherent cells from tissues analysed by RT-PCR after treatment with MAP4K4 siRNA (1) according to the protocol of FIG. 20b. FIG. 20e shows serum INFγ levels from control procedures (Scr siRNA-loaded GeRPs, unloaded GeRPs and PBS). FIGS. 20f, g and h show MAP4K4 or TNF-α expression in PECs and adherent cells from tissues after oral administration of MAP4K4 (2), TNF-α (1) or TNF-α (2) siRNAs, respectfully, according to the protocol of FIG. 20b. Comparative data analysis is provided in FIGS. 21 and 22.

FIG. 24a-b shows TNF-α mRNA expression in PECs treated with GeRP containing 40 pmoles of Scr, MAP4K4 siRNA (map4K4 siRNA (1), panel a of FIG. 24) or a second MAP4K4 siRNA ("MAP4K4 (2)", panel b of FIG. 24). Results are expressed in arbitrary units and are the mean±SEM (n=4). Statistical significance was determined by analysis of variance and Tukey post test.* (1)<0.01). FIG. 24c shows TNF-α mRNA expression in PECs treated with GeRP containing 40 pmoles of Scr (1) or MAP4K4 (1) siRNA and incubated with different concentrations of LPS, while FIG. 24d shows TNFα secretion by PECs treated under the same conditions. FIG. 24e shows that GeRPs loaded with Scr (1) siRNA or Scr (2) siRNA have no significant effect on expression of MAP4K4 or TNF-α.

FIG. 27 shows that MAP4K4 silencing does not affect LPS activation of MAP kinase and NFkB signaling pathways. PECs were treated with GeRPs containing 40 pmoles of Scr or MAP4K4 siRNA. 48 hours later cells were treated with 1 µg/ml LPS for the indicated amounts of time. Cells lysates were western blotted for phosphorylated and total (a) JNK1/2, (b) ERK1/2, (c) p38MAPK, (d) ATF-2, (e) phosphorylated cJUN and (f) total IkBα. Graphs show the mean densitometry analysis±SEM of western blot signals from three different experiments and are expressed in arbitrary units (n=3): Scr-siRNA data is represented by black squares and MAP4K4-siRNA is represented by white triangles. Under these conditions, MAP4K4 depletion markedly attenuated TNF-α expression (not shown). (g) Schematic diagram of potential MAP4K4 signaling to modulate the expression of inflammatory genes such as TNF-α and IL-1β.

FIG. 28 shows that MAP4K4 silencing inhibits LPS-induced lethality as well as TNF-α and IL-1β production in vivo. FIG. 28a shows a timeline of siRNA and D-galactosamine (D-GalN)/LPS administration. FIG. 28b shows expression of TNF-α, IL-1β, IL-10 and CCR2 in PECs isolated from mice orally treated with GeRP siRNA formulations (10 ug/kg). Statistical significance was determined by a two tailed student's T-test. FIGS. 28c-d show serum and peritoneal fluid TNF-α levels in MAP4K4 siRNA-treated mice 1.5, 4 and 28 hours after LPS/D-GalN injection. Statistical significance was determined by of variance and Tukey post test. FIGS. 28e-g compare knockdown of TNF-α and IL-1β by MAP4K4 (2) siRNA to knockdown of IL-1β by TNF-α (1) and (2) siRNAs.

FIG. 36a-b shows expression of aP2 mRNA (panels a and b) and MAP4K4 mRNA (panel b) after treatment with GeRPs loaded with aP2 siRNA, MAP4K4 (1) siRNA or Scr siRNA ((1) or (2)). Treatment with MAP4K4 and aP2 siRNAs decreases expression of their respective genes. FIG. 36-c-d shows the effects on TNF-α expression and secretion by PECs after treatment with GeRPs loaded with siRNAs. Only treatment with GeRPs loaded with MAP4K4 siRNA decreased TNF-α expression and secretion.

DETAILED DESCRIPTION OF THE INVENTION

Figure 1C:
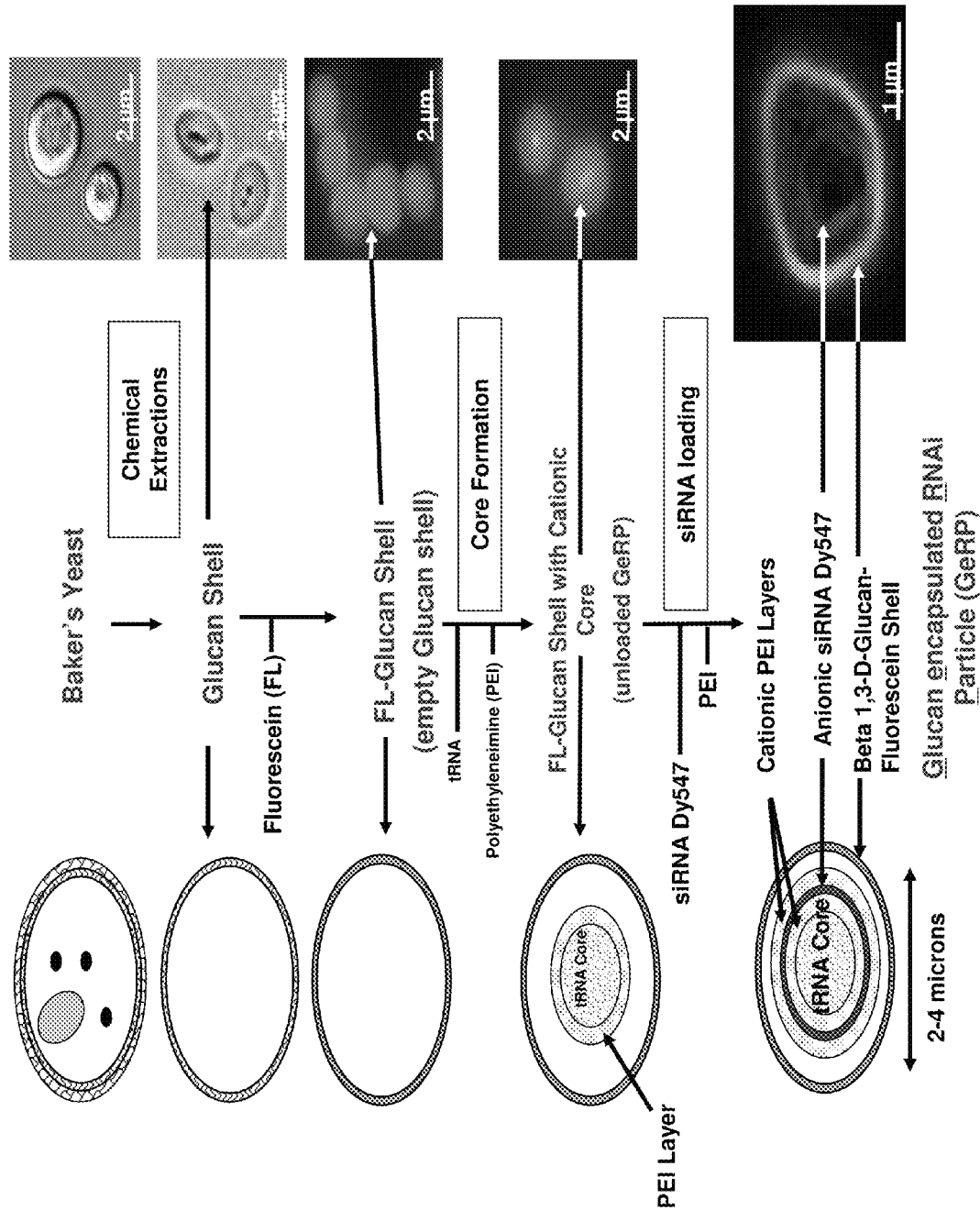
FIG. 1 shows a schematic depiction of (a) Nanoparticulate cores constructed within YCWP, (b) the adsorption of DNA onto the nanoparticulate core and (c) a process for generating GeRPs, starting with baker's yeast and ending with a schematic representation of the formulation of glucan-encapsulated siRNA particles (GeRPs).

The discovery that short sequences of double stranded RNA can cause depletion of cognitive RNA transcripts in eukaryotic cells has greatly expanded our understanding of gene regulation. The specificity and potency of gene silencing by RNA interference (RNAi) is facilitated by cellular machinery that mediates these actions. For therapeutic applications, double stranded short interfering RNA (siRNA) oligonucleotides are relatively nontoxic, readily designed for high specificity, and need not be restricted to genes that encode proteins that bind small molecule drugs. Thus RNAi can be targeted to all genes that encode protein sequences. Additionally, siRNAs are designed to minimize the interferon response associated with exposure of cells to long sequences of double stranded RNA.

Despite these properties, obstacles to in vivo delivery of siRNA are numerous and daunting. These include rapid degradation of siRNA oligonucleotides in extracellular environments, rapid excretion through the kidney, and low permeability through tight junctions and across cell surface membranes. The exists a need to develop techniques that orally deliver siRNA-mediated gene silencing to specific target tissues and cell types.

To achieve this goal, macrophages are used as targets because they control inflammatory responses associated with such major diseases as rheumatoid arthritis, colitis, and atherosclerosis. As a specialized host defense cell, the macrophage is a validated pharmaceutical target that contributes to pathogenesis through secretion of such inflammatory cytokines as tumor necrosis factor alpha (TNF-α) and interleukin-1 beta (IL-1β).

To accomplish oral delivery of siRNA to macrophages in mice, the present invention utilizes micron-sized particles of β1,3-D-glucan and their ability to pass through M cells in Peyer's patches in the intestinal wall to the underlying gut associated lymphatic tissue (GALT). Following transcytosis of such β1,3-D-glucan particles into the GALT, they undergo phagocytosis by resident macrophages and dendritic cells via the dectin-1 receptor and perhaps other beta glucan receptor-mediated pathways. GALT macrophages traffic away from the gut and infiltrate other reticuloendothelial system tissues, such that over time a significant proportion of total body macrophages contain ingested glucan particles.

Embodiments of the invention feature methods and compositions for delivering payloads to cells using particles comprising materials found in yeast cell walls. Particles of the invention can include yeast cell wall particle (YCWP) exteriors and nanocomplexed interiors. Nanocomplexed interiors of the invention can include payload agents, e.g., siRNAs, and trapping agents, e.g., cationic polymers and/or detergents.

In preferred aspects, the invention features glucan encapsulated nucleic acid delivery system (such as DNA and RNA, including siRNA) made using layer by layer (LbL) synthesis of nanocomplexed interiors within β-glucan containing microparticles, known as Yeast Cell Wall Particles (YCWP). YCWP are hollow and porous 2-4 micron microspheres prepared from, for example, Baker's yeast. The hydrocolloid shell is composed primarily of beta 1,3-D-glucan, mannoproteins and chitin and is typically <200 nm thick (FIG. 1a).

The encapsulation system cages polyelectrolyte nanocomplexes containing nucleic acid, within the YCWP that facilitates oral uptake into gut associated macrophages and dendritic cells, and intracellular nucleic acid (e.g., siRNA) delivery and gene modulation in these cells. Formation of the polyelectrolyte nanocomplexes follows a layer-by-layer (LbL) approach, with the different components assembled through electrostatic interactions. The use of YCWP as a carrier for transient gene therapy requires the formation of nanoparticulate cores within YCWP with the outmost layer being positively charged. This cationic layer can be used to electrostatically bind nucleic acid to the positively charged core surface. The nucleic acid is then coated with a second cationic polymer layer to protect the nucleic acid and the YCWP caged nanoplexed nucleic acid formulation is ready to be delivered to cells or administered to animals.

I. Definitions

So that the invention may be more readily understood, certain terms are first defined.

As used herein, the term "nanoparticle" refers to a particle (e.g., a spherical particle) of less than 1 micron in diameter, e.g., 500, 200, 100, 50 nanometers or less in diameter.

As used herein, the term "yeast cell wall particle" ("YCWP") refers to a micron-sized β-glucan shell or particle resulting from alkaline, acid and/or solvent extraction of yeast to remove cytoplasmic components and/or other proteins and/or polysaccharides.

As used herein, the term yeast glucan mannan particle ("YGMP") or glucan mannan particle ("GMP") or glucan mannan shell ("GMS") refers to a YCWP comprising a significant percentage of yeast cell wall β-glucan and mannan. The extraction process is such that a significant percentage of the β-glucan and mannan present in the source yeast cell wall remains in the particle following extraction.

As used herein, the term yeast glucan particle ("YGP") or glucan particle ("GP"), or glucan shell ("GS") refers to a YCWP comprising primarily yeast cell wall β-glucan. Harsher extraction conditional are used as compared to those for making YGMPs such that mannan is removed from the particle walls.

As used herein, the term "glucan encapsulated siRNA particle" ("GeRP") refers to a YCWP, GP or glucan shell containing siRNA encapsulated within.

As used herein, the term "core" refers to the center of a nanoparticle around which layers (e.g., payload layers and/or trapping layers) or sections are formed by encapsulation.

As used herein, the term "core agent" refers to an agent or molecule (e.g., compound, polymer, etc.) incorporated into a core. Core agents can include payload molecules, trapping molecules, etc.

As used herein, the term "payload molecule" or "payload agent" refers to an agent or molecule (e.g., a pharmaceutically active agent) of interest which is delivered or released from nanoparticle or a delivery system comprising said nanoparticle. In exemplary embodiments, a payload molecule is selected from the group consisting of a nucleic acid, a peptide, a protein, a small organic active agent, a small inorganic active agent, and a mixture thereof. For example, the payload molecule may be a therapeutic agent or a diagnostic agent.

As used herein, the term "payload layer" is a layer (e.g., a layer of a nanoparticle) including at least one payload molecule or agent.

As used herein, the term "payload core" is a core further comprising at least one payload molecule or agent.

As used herein, the term "trapping molecule" or "trapping agent" refers to a molecule or agent which facilitates the retention (e.g., the temporary retention) of a payload molecule or agent within a nanoparticle (or a delivery system comprising said nanoparticle) for at least period of time. In certain embodiments, the trapping molecule or agent facilitates retention of the molecule until the uptake of the delivery system by a target cell. In certain embodiments, the trapping molecule is biocompatible and pharmacologically acceptable. Preferably, the payload molecule and the trapping molecule are soluble in the same solvent system. Exemplary payload molecules includes natural and synthetic polymers (e.g., agarose, polyacrylamide, polysaccharides), charged (e.g., cationic or anionic) polymers, detergents, and the like.

As used herein, the term trapping layer is a layer including at least one trapping molecule.

II. Nucleic Acid Payload Agents

In exemplary embodiments, the compositions of the invention comprise nucleic acid-based payload agents. Exemplary payload agents include, but are not limited to RNA silencing agents (e.g., siRNAs, siRNA-like molecules, miRNAs, shRNAs), other nucleic acids with gene silencing activity (e.g., antisense molecules and/or ribozymes), or nucleic acid constructs (e.g., DNA constructs) encoding said RNA silencing agents and other gene silencing nucleic acids.

A. RNA Silencing Agents

The present invention features RNA silencing agents (e.g. siRNAs, miRNAs, shRNAs) for use in various compositions and methodologies of the invention. The RNA silencing agents comprise an antisense strand (or portions thereof), wherein the antisense strand has sufficient complementary to a target mRNA to mediate silencing of the mRNA via an RNA-mediated silencing mechanism (e.g., RNAi).

i. siRNA Molecules

An siRNA molecule of the invention is a duplex consisting of a sense strand and complementary antisense strand, the antisense strand having sufficient complementary to a target mRNA sequence to direct a target-specific RNA silencing mechanism. In preferred embodiments, the antisense strand has sufficient complementary to the target mRNA to direct RNA interference (RNAi), as defined herein, i.e., the siRNA has a sequence sufficient to trigger the destruction of the target mRNA by the RNA silencing machinery or process. In alternative embodiments, the antisense strand of the siRNA has sufficient complementarity to a target mRNA sequence to direct translation repression of the target mRNA.

In certain embodiments, the siRNA molecule has a length from 5-60 (e.g., about 10-50) or more nucleotides, i.e., each strand comprises 5-60 (e.g., 10-50) nucleotides (or nucleotide analogs). In certain exemplary embodiments, the siRNA molecule has a length from about 16-30, e.g., 16, 17, 18, 19, 20, 21, 22, 23, 24, 25, 26, 27, 28, 29, or 30 nucleotides in each strand, wherein one of the strands is sufficiently complementary to a target region, and the other strand is identical or substantially identical to the first strand (e.g., having 5 or fewer (e.g., 1, 2, 3, or 4) mismatches relative to the first strand). In certain particular embodiments, the siRNA molecule has a length of from about 18-25 nucleotides (e.g., 18, 19, 20, 21, 22, 23, 24, or 25 nucleotides). In other particular embodiments, the siRNA molecule has a length of from about 25-30 nucleotides (e.g., 25, 26, 27, 28, 29, or 30 nucleotides). In other particular embodiments, the siRNA molecule has a length of from about 25-35 nucleotides (e.g., 25, 26, 27, 28, 29, 30, 31, 32, 33, 34 or 35 nucleotides). In other embodiments, siRNAs may have shorter or longer lengths. In one embodiment, the siRNA has a length of about 5-15 nucleotides or nucleotide analogs (e.g., 5, 6, 7, 8, 9, 10, 11, 12, 13, 14, or 15 nucleotides) in each strand, wherein one of the strands is sufficiently complementary to a target region. In another embodiment, the siRNA has a length of about 30-35 nucleotides or nucleotide analogs (e.g., 30, 31, 32, 33, 34 or 35 nucleotides in each strand, wherein one of the strands is sufficiently complementary to a target region). In another embodiment, the siRNA has a length of about 30-60 nucleotides or nucleotide analogs (e.g., 35, 40, 45, 50, 55, or 60 nucleotides in each strand, wherein one of the strands is sufficiently complementary to a target region).

In certain embodiments, the strands of the siRNA molecule are of different lengths (e.g., they differ in length by 5 or fewer nucleotides (e.g., 1, 2, 3, or 4). In other embodiments, the strands of the siRNA molecule are of the same length.

In certain embodiments, the strands of the siRNA molecule aligned such that one or both ends of the siRNA molecule are blunt-ended (i.e., lack an overhang). In other embodiments, the strands of the siRNA molecule are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. In certain embodiments, at least one (preferably both) ends of the duplex comprise a 2 nucleotide overhands (e.g., dTdT overhangs).

Generally, siRNAs can be designed by using any method known in the art, for instance, by using the following protocol:

1. A target mRNA is selected and one or more target sites are identified within said target mRNA. Cleavage of mRNA at these sites results in mRNA degradation, preventing production of the corresponding protein. Polymorphisms from other regions of the mutant gene are also suitable for targeting.

In preferred embodiments, the target sequence comprises AA dinucleotide sequences; each AA and the 3' adjacent 16 or more nucleotides are potential siRNA targets. In another preferred embodiment, the nucleic acid molecules are selected from a region of the target mRNA sequence beginning at least 50 to 100 nt downstream of the start codon, e.g., of the sequence of the target mRNA. Further, siRNAs with lower G/C content (35-55%) may be more active than those with G/C content higher than 55%. Thus in one embodiment, the invention includes target sequences having 35-55% G/C content, although the invention is not limited in this respect.

2. The sense strand of the siRNA is designed based on the sequence of the selected target site. For example, the sense strand may include about 18 to 25 nucleotides, e.g., 18, 19, 20, 21, 22, 23, 24 or 25 nucleotides. The skilled artisan will appreciate, however, that siRNAs having a length of less than 19 nucleotides or greater than 25 nucleotides can also function to mediate RNAi. For example, in certain embodiments, the sense strand may include about 25 to about 30 nucleotides, e.g., 25, 26, 27, 28, 29, or 30 nucleotides. In other embodiments, the sense strand may include about 30 to about 35 nucleotides, e.g., 30, 31, 32, 33, 34 or 35 nucleotides. Accordingly, siRNAs of such length are also within the scope of the instant invention provided that they retain the ability to mediate RNAi. RNA silencing agents of longer lengths have been demonstrated to elicit an interferon or PKR response in certain mammalian cells which may be undesirable. Preferably the RNA silencing agents of the invention do not elicit a PKR response (i.e., are of a sufficiently short length). However, longer RNA silencing agents may be useful, for example, in cell types incapable of generating a PKR response or in situations where the PKR response has been downregulated or dampened by alternative means.

The siRNA molecules of the invention have sufficient complementarity with the target site such that the siRNA can mediate RNAi. In general, siRNA containing nucleotide sequences sufficiently identical to a portion of the target gene to effect RISC-mediated cleavage of the target gene are preferred. Accordingly, in a preferred embodiment, the sense strand of the siRNA is designed have to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. The invention has the advantage of being able to tolerate certain sequence variations to enhance efficiency and specificity of RNAi. In one embodiment, the sense strand has 4, 3, 2, 1, or 0 mismatched nucleotide(s) with a target region, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense strand sequence is designed such that nucleotides corresponding to the desired target cleavage site are essentially in the middle of the strand. For example, if a 21-nucleotide siRNA is chosen, nucleotides corresponding to the target cleavage site are at, for example, nucleotide 6, 7, 8, 9, 10, 11, 12, 13, 14, 15 or 16 (i.e., 6, 7, 8, 9, 10, 11, 12, 13, 14, 15 or 16 nucleotides from the 5' end of the sense strand. For a 22-nucleotide siRNA, nucleotides corresponding to the target cleavage site are at, for example, nucleotide 7, 8, 9, 10, 11, 12, 13, 14, 15 or 16. For a 23-nucleotide siRNA, nucleotides corresponding to the target cleavage site are at, for example, 7, 8, 9, 10, 11, 12, 13, 14, 15 or 16. For a 24-nucleotide siRNA, nucleotides corresponding to the target cleavage site are at, for example, 9, 10, 11, 12, 13, 14 or 16. For a 25-nucleotide siRNA, nucleotides corresponding to the target cleavage site are at, for example, 9, 10, 11, 12, 13, 14, 15, 16 or 17. Moving nucleotides corresponding to an off-center position may, in some instances, reduce efficiency of cleavage by the siRNA. Such compositions, i.e., less efficient compositions, may be desirable for use if off-silencing of a second (non-target) mRNA is detected.

The sense strand is designed such that complementarity exists between the antisense strand of the siRNA and the sense strand. In certain exemplary embodiments, the siRNA is designed such that the strands have blunt ends. In other exemplary embodiments, the siRNA is designed such that the strands have overhanging ends, e.g., overhangs of 1, 2, 3, 4, 5 or more nucleotide at one, or both, ends of the siRNA. Exemplary overhangs are deoxynucleotide overhangs, for example, a dTdT tail.

4. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 4, e.g., 2, nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus in another embodiment, the nucleic acid molecules may have a 3' overhang of 2 nucleotides, such as TT. The overhanging nucleotides may be either RNA or DNA.

5. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

6. Select one or more sequences that meet your criteria for evaluation. Further general information about the design and use of siRNA may be found in "The siRNA User Guide," available at The Max-Plank-Institut für Biophysikalishe Chemie website.

Alternatively, the siRNA may be defined functionally as comprising an antisense or guide strand having a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, $Tm(°C.)=2(\# \text{ of A+T bases})+4(\# \text{ of G+C bases})$. For hybrids between 18 and 49 base pairs in length, $Tm(°C.)=81.5+16.6(\log 10[Na+])+0.41(\% G+C)-(600/N)$, where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA; a homology search can be performed to ensure that the negative control lacks homology to any other gene in the appropriate genome. Negative control siRNA In addition, negative control siRNAs can be designed by introducing a significant number of base mismatches into the sequence.

7. To validate the effectiveness by which siRNAs cleave target mRNAs (e.g., mutant mRNAs), the siRNA may be incubated with target cDNA in a *Drosophila*-based in vitro mRNA expression system. Radiolabeled with $32^P$, newly synthesized mutant target mRNAs are detected autoradiographically on an agarose gel. The presence of cleaved mutant mRNA indicates mRNA nuclease activity. Suitable controls include omission of siRNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

a. Preferred siRNA Molecules

Embodiments of the invention feature encapsulated nanoparticles comprising siRNAs. In some preferred embodiments, the siRNAs are designed to decrease the expression of genes involved in metabolic disorders and/or in inflammatory disorders. In some preferred embodiments, these genes include Map4k4, TNF-alpha, RIP140, TLR4 and aP2.

Exemplary siRNA molecules for use with some embodiments of the invention are provided herein. Such molecules include siRNAs against mouse Map4k4 (GAC CAA CUC UGG CUU GUU A) (SEQ ID NO: 1), mouse TNFα (CUG UUG GUU GAU CAC CAC G) (SEQ ID NO: 2) and mouse Rip140 (GGA AUG AGC UCG AUU AUA A) (SEQ ID NO: 3) (sequences listed here 5' to 3'). In some embodiments, these siRNA sequences include an additional two nucleotides (UU) overhanging the 3' end of siRNA.

Embodiments of the invention include siRNAs directed to reducing expression of human Map4k4 (mitogen-activated protein kinase kinase kinase kinase 4), including the following open reading frame sequences in Table 1:

TABLE 1

| Sense Strand Sequence for human Map4k4 | SEQ ID NOS |
|---|---|
| GAAGAAGAGAGGCGAGAAA | 4 |
| UUACAGACCUUGUGAAGAA | 5 |
| GGAGAGAACAAGAAGAAAA | 6 |
| GGCCAGAGGUUGAAAGUGA | 7 |
| GAGCAAUGGUGAAACGGAA | 8 |

TABLE 1-continued

| Sense Strand Sequence for human Map4k4 | SEQ ID NOS |
|---|---|
| UGGUGGAAGUGGUUGGAAA | 9 |
| GGUGAAACUUGUUGACUUU | 10 |
| GGAUUGAGCAGCAGAAAGA | 11 |
| GAGGAGAGUUGAAAGAGAA | 12 |
| CCAAAUGAAAGGCAAGUUA | 13 |

In some embodiments, these siRNA sequences include an additional two nucleotides (UU) overhanging the 3' end of siRNA.

Additional exemplary siRNA sequences for use with embodiments of the invention include (5' to 3' sequences): CAGUCGCGUUUGCGACUGG (SEQ ID NO: 14) (scramble); GACCAACUCUGGCUUGUUA (SEQ ID NO: 1) (MAP4K4 (1)); CAGAAGTGGCCAAGGGAAA (SEQ ID NO: 15) (MAP4K4 (2)); CUGUUGGUUGAUCACCACG (SEQ ID NO: 2) (TNF-α (1)); GCATGGATCTCAAAGACAA (SEQ ID NO: 16) (TNF-α (2)); and CGACCACAATAAAGAGAAA (SEQ ID NO: 17) (aP2).

ii. siRNA-Like Molecules

In other embodiments, the compositions of the instant invention comprise siRNA-like molecules. siRNA-like molecules of the invention have a sequence (i.e., have a strand having a sequence) that is "sufficiently complementary" to a target mRNA to direct gene silencing either by RNA silencing or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNA silencing is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment, 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further preferred embodiment, the "bulge" is centered at nucleotide positions 12 and 13 from the 5' end of the miRNA molecule.

iii. miRNAs

In certain embodiments, the compositions of the invention comprise miRNAs. miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof.

The miRNA sequence can be similar or identical to that of any naturally occurring miRNA (see e.g. The miRNA Registry; Griffiths-Jones S, Nuc. Acids Res., 2004). Over one thousand natural miRNAs have been identified to date and together they are thought to comprise ~1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiR-Seeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans*, zebrafish, *Arabidopsis thalania*, mouse, and rat as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex but only one strand is taken up by the RISC complex to direct gene silencing. Certain miRNAs, e.g. plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between an miRNA and its target mRNA is believed to determine its mechanism of action. For example, perfect or near-perfect complementarity between a miRNA and its target mRNA is predictive of a cleavage mechanism (Yekta et al., Science, 2004), whereas less than perfect complementarity is predictive of a translational repression mechanism. In particular embodiments, the miRNA sequence is that of a naturally-occurring miRNA sequence, the aberrant expression or activity of which is correlated with a miRNA disorder.

Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, may comprise sequence derived from these naturally occurring pre-miRNAs, but are engineered to deliver desired RNA silencing agents (e.g., siRNAs of the invention). For example, by substituting the stem sequences of the pre-miRNA with sequence complementary to the target mRNA, a shRNA is formed. The shRNA is processed by the entire gene silencing pathway of the cell, thereby efficiently mediating RNAi.

In certain embodiments, where post-transcriptional gene silencing by translational repression of the target gene is desired, the miRNA sequence has partial complementarity with the target gene sequence. In exemplary embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

iv. Short Hairpin RNA (shRNA) Molecules

In certain embodiments, the compositions of the invention comprise shRNAs. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In exemplary shRNAs, one portion of the duplex stem is a nucleic acid sequence that is complementary (or anti-sense) to the target mRNA. Preferably, one strand of the stem portion of the shRNA is sufficiently complementary (e.g., antisense) to a target RNA (e.g., mRNA) sequence to mediate degradation or cleavage of said target RNA via RNA interference (RNAi). Thus, shRNAs may include a duplex stem with two portions and a loop connecting the two stem portions. The antisense portion can be on the 5' or 3' end of the stem. The stem portions of a shRNA are preferably about 15 to about 50 nucleotides in length. Preferably the two stem portions are about 18 or 19 to about 21, 22, 23, 24, 25, 30, 35, 37, 38, 39, or 40 or more nucleotides in length. In preferred embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs can be 2, 3, 4, 5, 6, 7, 8, 9, or more, e.g., 15 or 20, or more nucleotides in length.

A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In certain embodiments, shRNAs of the invention include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA, for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA, siRNA-like duplex, or miRNA desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro. In certain embodiments, shRNAs may include miRNA sequences, optionally end-modified miRNA sequences, to enhance entry into RISC.

B. Chemically-Modified RNA Silencing Agents

In certain aspects, the compositions of the invention comprise RNA silencing agents wherein the sense strand and/or antisense strand is modified by the substitution of nucleotides with chemically modified nucleotides. In one embodiment, the sense strand and/or the antisense strand are modified with one or more internal chemical modifications. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or the antisense strand are modified at the 5' end and/or the 3' end. In one embodiment, the sense strand and/or the antisense strand are modified at both the 5' end and the 3' end. As used herein, the term "modified at the end" when used in reference to the 5' or 3' ends, refers to any nucleotide within 10 nucleotides of the first and last nucleotide, for example any nucleotide within 7 nucleotides of the first and last nucleotide. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the nucleotides. In yet another embodiment, the sense strand and/or antisense strand is modified by the substitution of all of the nucleotides. Within the RNA silencing agents employed in the invention, as few as one and as many as all nucleotides of the oligonucleotide can be modified. In some embodiments, the RNA silencing agent will contain as few modified nucleotides as are necessary to achieve a desired level of in vivo stability and/or bioaccessibility while maintaining cost effectiveness.

Chemical modifications may lead to increased stability, e.g., increased or enhanced in vivo stability, compared to an unmodified RNA silencing agent or a label that can be used, e.g., to trace the RNA silencing agent, to purify an RNA silencing agent, or to purify the RNA silencing agent and cellular components with which it is associated. Such chemical modifications can also be used to stabilize the first (priming) strand of the siRNA for enhancing RISC activity/RNA silencing responsiveness in a cell (or cell extract or organism) and improve its intracellular half-life for subsequent receipt of the second strand wherein RNA silencing/gene silencing can now progress. Modifications can also enhance properties such as cellular uptake of the RNA silencing agents and/or stability of the RNA silencing agents, can stabilize interactions between base pairs, and can maintain the structural integrity of the antisense RNA silencing agent-target RNA duplex. RNA silencing agent modifications can also be designed such that properties important for in vivo applications, in particular, human therapeutic applications, are improved without compromising the RNA silencing activity of the RNA silencing agents e.g., modifications to increase resistance of, e.g., siRNA or miRNA molecules to nucleases. In certain embodiments, modified siRNA molecules of the invention can enhance the efficiency of target RNA inhibition as compared to a corresponding unmodified siRNA. In some embodiments, modified nucleotides do not affect the ability of the antisense strand to adopt A-form helix conformation when base-pairing with the target RNA sequence, e.g., an A-form helix conformation comprising a normal major groove when base-pairing with the target RNA sequence.

Chemical modifications generally include end-, sugar-, base- and/or backbone-modifications to the ribonucleotides (i.e., include modifications to the phosphate-sugar backbone).

In one embodiment, the RNA silencing agent of the invention comprises one or more (e.g., about 1, 2, 3, or 4) end modifications. For example, modification at the 5' end of an siRNA molecule comprises, for example, a 5'-propylamine group. Modifications of the 5' end may also include 5' terminal phosphate groups, such as those described by Formula I:

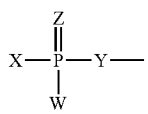

(I)

wherein each X and Y is independently O, S, N, alkyl, substituted alkyl, or alkylhalo; wherein each Z and W is independently O, S, N, alkyl, substituted alkyl, O-alkyl, S-alkyl, alkaryl, aralkyl, alkylhalo, or acetyl. In some embodiments, W, X, Y and Z are not all O. Modifications to the 3' OH terminus of an siRNA molecule can include, but are not limited to, 3'-puromycin, 3'-biotin (e.g., a photocleavable biotin), a peptide (e.g., a Tat peptide), a nanoparticle, a peptidomimetic, organic compounds (e.g., a dye such as a fluorescent dye), or a dendrimer. End modifications may be on the sense strand, on the antisense strand or both. In some embodiments, the 5' modifications are on the sense strand only.

In another embodiment, the RNA silencing agent of the invention may comprise one or more (e.g., about 1, 2, 3, 4, 5, 6, 7, 8, 9, 10, or more) sugar-modified nucleotides. Exemplary sugar modifications may include modifications represented by Formula II:

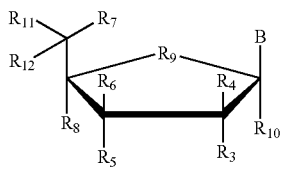

(II)

wherein each $R_3$, $R_4$, $R_5$, $R_6$, $R_7$, $R_8$, $R_{10}$, $R_{11}$ and $R_{12}$ is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-5-alkyl, alkyl-O-alkyl, ONO2, NO2, N3, NH2, aminoalkyl, aminoacid, aminoacyl, ONH2, O-aminoalkyl, O-aminoacid, or O-aminoacyl, heterocycloalkyl, heterocycloalkaryl, aminoalkylamino, polyalklylamino, substituted silyl; $R_9$ is O, S, CH2, S=O, CHF, or CF2, and B is a nucleosidic base. Sugar-modified nucleotides include, but are not limited to: 2'-fluoro modified ribonucleotides, 2'-OMe modified ribonucleotides, 2'-deoxy ribonucleotides, 2'-amino modified ribonucleotides and 2'-thio modified ribonucleotides. The sugar-modified nucleotide can be, for example, 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine or 2'-amino-butyryl-pyrene-uridine. In one embodiment, the sugar-modified nucleotide is a 2'-fluoro ribonucleotide. In some embodiments, when a 2'-deoxy ribonucleotide is present, it is upstream of the cleavage site referencing the antisense strand or downstream of the cleavage site referencing the antisense strand. The 2'-fluoro ribonucleotides can be in the sense and antisense strands. In some embodiments, the 2'-fluoro ribonucleotides are every uridine and cytidine. In other embodiments, the 2'-fluoro ribonucleotides are only present at the 3' and 5' ends of the sense strand, the antisense strand or both.

In another embodiment, the RNA silencing agent of the invention comprises one or more (e.g., about 1, 2, 3, 4, 5, 6, 7, 8, 9, 10, or more) nucleobase-modified nucleotides. Nucleobase-modified nucleotides useful in the invention include, but are not limited to: uridine and/or cytidine modified at the 5-position (e.g., 5-bromo-uridine, 5-(2-amino)propyl uridine, 5-amino-allyl-uridine, 5-iodo-uridine, 5-methyl-cytidine, 5-fluoro-cytidine, and 5-fluoro-uridine), ribo-thymidine, 2-aminopurine, 2,6-diaminopurine, 4-thio-uridine, adenosine and/or guanosines modified at the 8 position (e.g., 8-bromo guanosine), deaza nucleotides (e.g., 7-deaza-adenosine), O- and N-alkylated nucleotides (e.g., N6-methyl adenosine) and non-nucleotide-type bases (e.g., deoxy-abasic, inosine, N3-methyl-uridine, N6,N6-dimethyl-adenosine, pseudouridine, purine ribonucleoside and ribavirin).

In another embodiment, the RNA silencing agent of the invention comprises one or more (e.g., about 1, 2, 3, 4, 5, 6, 7, 8, 9, 10, or more) backbone-modified nucleotides. For example, backbone modifications may include modifications represented by Formula III:

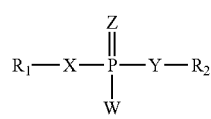

(III)

wherein each R1 and R2 is independently any nucleotide as described herein, each X and Y is independently O, S, N, alkyl, or substituted alkyl, each Z and W is independently O, S, N, alkyl, substituted alkyl, O-alkyl, S-alkyl, alkaryl, aralkyl, or acetyl. In some embodiments, W, X, Y, and Z are not all O. Exemplary backbone-modified nucleotides contain a phosphorothioate group or a phosphorodithioate. In another embodiment, a backbone modification of the invention comprises a phosphonoacetate and/or thiophosphonoacetate internucleotide linkage (see for example Sheehan et al., 2003, Nucleic Acids Research, 31, 4109-4118). The backbone-modifications can be within the sense strand, antisense strand, or both the sense and antisense strands. In some embodiments, only a portion of the internucleotide linkages are modified in one or both strands. In other embodiments, all of the internucleotide linkages are modified in one or both strands. In one embodiment, the modified internucleotide linkages are at the 3' and 5' ends of one or both strands.

In another embodiment, the siRNA molecule of the invention may comprise one or more (e.g., about 1, 2, 3, 4, 5, 6, 7, 8, 9, 10, or more) crosslinks, e.g., a crosslink wherein the sense strand is crosslinked to the antisense strand of the siRNA duplex. Crosslinkers useful in the invention are those commonly known in the art, e.g., psoralen, mitomycin C, cisplatin, chloroethylnitrosoureas and the like. In one embodiment, the crosslink of the invention is a psoralen crosslink. Preferably, the crosslink is present downstream of the cleavage site referencing the antisense strand, and more preferably, the crosslink is present at the 5' end of the sense strand.

In another embodiment, the RNA silencing agent of the invention comprises a sequence wherein the antisense strand and target mRNA sequences comprise one or more (e.g., about 1, 2, 3, 4, 5, 6, 7, 8, 9, 10, or more) mismatches. In some embodiments, the mismatch is downstream of the cleavage site referencing the antisense strand, e.g., within 1-6 nucleotides from the 3' end of the antisense strand. In another embodiment, the nucleic acid molecule, e.g., RNA silencing agent, of the invention is an siRNA molecule that comprises a bulge, e.g., one or more (e.g., about 1, 2, 3, 4, 5, 6, 7, 8, 9, 10, or more) unpaired bases in the duplex siRNA. In some embodiments, the bulge is in the sense strand.

It is to be understood that any of the above combinations can be used in any combination to provide the modified RNA silencing agent of the present invention. For example, in some embodiments, the invention includes an siRNA, wherein the sense strand includes one or more (e.g., about 1, 2, 3, 4, 5, 6, 7, 8, 9, 10, or more) phosphorothioate internucleotide linkages, and/or one or more (e.g., about 1, 2, 3, 4, 5, 6, 7, 8, 9, 10 or more) 2'-deoxy, 2'-O-methyl, and/or 2'-fluoro sugar modifications, and/or one or more (e.g., about 1, 2, 3, 4, 5, 6, 7, 8, 9, 10 or more) base modified nucleotides, and/or an end-modification at the 3'-end, the 5'-end, or both the 3'- and 5'-ends of the sense strand. In some embodiments, the invention includes an siRNA, wherein the antisense strand includes one or more (e.g., about 1, 2, 3, 4, 5, 6, 7, 8, 9, 10, or more) phosphorothioate internucleotide linkages, and/or one or more (e.g., about 1, 2, 3, 4, 5, 6, 7, 8, 9, 10 or more) 2'-deoxy, 2'-O-methyl, and/or 2'-fluoro sugar modifications, and/or one or more (e.g., about 1, 2, 3, 4, 5, 6, 7, 8, 9, 10 or more) base modified nucleotides, and/or an end-modification at the 3'-end, the 5'-end, or both the 3'- and 5'-ends of the antisense strand. In yet other embodiments, the invention includes an siRNA, wherein both the sense strand and the antisense strand include one or more (e.g., about 1, 2, 3, 4, 5, 6, 7, 8, 9, 10, or more) phosphorothioate internucleotide linkages, and/or one or more (e.g., about 1, 2, 3, 4, 5, 6, 7, 8, 9, 10 or more) 2'-deoxy, 2'-O-methyl, and/or 2'-fluoro sugar modifications, and/or one or more (e.g., about 1, 2, 3, 4, 5, 6, 7, 8, 9, 10 or more) base modified nucleotides, and/or an end-modification at the 3'-end, the 5'-end, or both the 3'- and 5'-ends of either or both the sense strand and/or the antisense strand.

Modified RNA silencing agents of the invention (i.e., duplex siRNA molecules) can be modified at the 5' end, 3' end, 5' and 3' end, and/or at internal residues, or any combination thereof. RNA silencing agent modifications can be, for example, end modifications, sugar modifications, nucleobase modifications, backbone modifications, and can contain mismatches, bulges, or crosslinks. Also included are 3' end, 5' end, or 3' and 5' and/or internal modifications, wherein the modifications are, for example, cross linkers, heterofunctional cross linkers and the like. RNA silencing agents of the invention also may be modified with chemical moieties (e.g., cholesterol) that improve the in vivo pharmacological properties of the RNA silencing agents.

In certain aspects of the present invention, the chemically modified siRNAs of the present invention are "terminally-modified siRNAs". That is, the siRNAs are modified at one or both of the 3' end and the 5' end of the sense and/or antisense strand. In certain embodiments, the chemically modified siRNAs are modified at both the 3' end and the 5' end of both the sense antisense strand. In some embodiments, the 3' end and/or the 5' end of the sense and/or antisense strands are end-modified such that 2 or 3 or 4 modified nucleotides are incorporated per end (e.g., within the 5-7 terminal nucleotides, e.g., within the duplex). In some embodiments, the 3' end and/or the 5' end of the sense and/or antisense strands are end-modified such that 2 or 3 or 4 2'-fluoro nucleotides, e.g., 2' fluorocytidine and/or 2'fluorouracil, are incorporated per end (e.g., within the 5-7 terminal nucleotides, e.g., within the duplex). In some embodiments, the 3' end and/or the 5' end of the sense and/or antisense strands are end-modified such that 2 or 3 or 4 internucleotide linkages are phosphorothioate linkages per end (e.g., between the 5-7 terminal nucleotides, e.g., within the duplex). In some embodiments, the modifications include any of the modifications described herein. In other embodiments, the modifications include phosphorothioate linkages. In still other embodiments, the modifications include 2'-sugar modifications. In still other embodiments, the modifications include 2'-fluoro nucleotide modifications. In yet other embodiments, the modifications include both phosphorothioate linkages and 2'-fluoro nucleotide modifications.

In other aspects, RNA silencing agents may be modified according to methods described in the art (Amarzguioui et. al., Nuc. Acids. Res., (2003) 31: 589-95; Chiu and Rana, RNA, (2003), 9: 1034-48; Chiu and Rana, Mol. Cell., (2002), 10: 549-61); Morrissey et al., Nat. Biotech., (2005), 23: 2002-7), each of which is incorporated by reference herein. In one embodiment, RNA silencing agent may be conjugated a lipophilic moiety. In one embodiment, the lipophilic moiety is a ligand that includes a cationic group. In another embodiment, the lipophilic moiety is attached to one or both strands of an siRNA. In a preferred embodiment, the lipophilic moiety is attached to one end of the sense strand of the siRNA. In another preferred embodiment, the lipophilic moiety is attached to the 3' end of the sense strand. In certain embodiments, the lipophilic moeity is selected from the group consisting of cholesterol, vitamin E, vitaminK, vitamin A, folic acid, or a cationic dye (e.g., Cy3). In a preferred embodiment, the lipophilic moiety is a cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, bomeol, menthol, 1,3-propanediol, heptadecyl group, palmitic acid, myristic acid, O3-(oleoyl)lithocholic acid, O3-(oleoyl)cholenic acid, dimethoxytrityl, or phenoxazine. In some embodiments, the RNA silencing agent of the instant invention may also contain a nuclear localization/nuclear targeting signal(s). Such modifications may be made exclusive of, or in addition to, any combination of other modifications as described herein. Nuclear targeting signals include any art-recognized signal capable of effecting a nuclear localization to a molecule, including, for example, NLS signal sequence peptides.

Oligonucleotide RNA silencing agents may be produced enzymatically or by partial/total organic synthesis. In one embodiment, an RNA silencing agent, e.g., siRNA, is prepared chemically. Methods of synthesizing RNA and DNA molecules are known in the art, in particular, the chemical synthesis methods as described in Verma and Eckstein (1998) Annul Rev. Biochem. 67:99-134. RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the RNA molecules, e.g., RNA silencing oligonucleotides, can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) Methods Enzymol. 180:51-62). The RNA may be dried for storage or dissolved in an aqueous solution. The solution may contain buffers or salts to inhibit annealing, and/or promote stabilization of the single strands.

In one embodiment, siRNAs are synthesized either in vivo, in situ, or in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the siRNA. Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses siRNA from a recombinant construct may be produced by introducing the construct into a zygote, an embryonic stem cell, or another multipotent cell derived from the appropriate organism. Expression levels of target and any other surveyed RNAs and proteins may be assessed by any of a wide variety of well known methods for detecting expression of non-transcribed nucleic acid, and transcribed nucleic acid or protein. Non-limiting examples of such methods include RT-PCR of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays.

RNA expression levels can be assessed by preparing mRNA/cDNA (i.e. a transcribed polynucleotide) from a cell, tissue or organism, and by hybridizing the mRNA/cDNA with a reference polynucleotide which is a complement of the assayed nucleic acid, or a fragment thereof. cDNA can, optionally, be amplified using any of a variety of polymerase chain reaction or in vitro transcription methods prior to hybridization with the complementary polynucleotide; preferably, it is not amplified. Expression of one or more transcripts can also be detected using quantitative PCR to assess the level of expression of the transcript(s).

C. Other Nucleic Acid Molecules

In other embodiments, a nucleic acid molecule employed in a composition of the invention is a nucleic acid molecule other than an RNA silencing agent. In certain embodiments, said nucleic acid molecules may comprise any of the chemical modifications discussed supra.

i. Antisense Oligonucleotides

In one embodiment, a nucleic acid molecule employed in the invention is an antisense nucleic acid molecule that is complementary to a target mRNA or to a portion of said mRNA, or a recombinant expression vector encoding said antisense nucleic acid molecule. Antisense nucleic acid molecules are generally single-stranded DNA, RNA, or DNA/RNA molecules which may comprise one or more nucleotide analogs. The use of antisense nucleic acids to downregulate the expression of a particular protein in a cell is well known in the art (see e.g., Weintraub, H. et al., Antisense RNA as a molecular tool for genetic analysis, Reviews—Trends in Genetics, Vol. 1(1) 1986; Askari, F. K. and McDonnell, W. M. (1996) N. Eng. J. Med. 334:316-318; Bennett, M. R. and Schwartz, S. M. (1995) Circulation 92:1981-1993; Mercola, D. and Cohen, J. S. (1995) Cancer Gene Ther. 2:47-59; Rossi, J. J. (1995) Br. Med. Bull. 51:217-225; Wagner, R. W. (1994) Nature 372:333-335). An antisense nucleic acid molecule comprises a nucleotide sequence that is complementary to the target mRNA sequence and accordingly is capable of hydrogen bonding to the mRNA. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Preferably, an antisense nucleic acid is designed so as to be complementary to a region preceding or spanning the initiation codon in the 3' untranslated region of an mRNA.

Given the known nucleotide sequence of a target mRNA, antisense nucleic acids of the invention can be designed according to the rules of Watson and Crick base pairing. The antisense nucleic acid molecule can be complementary to the entire coding region of an mRNA, but more preferably is antisense to only a portion of the coding or noncoding region of an mRNA. For example, the antisense oligonucleotide can be complementary to the region surrounding the translation start site of a target mRNA. An antisense oligonucleotide can be, for example, about 5, 10, 15, 20, 25, 30, 35, 40, 45, 50, 60, 70, 80, 100, 500, 1000 nucleotides or more in length. In some embodiments, the antisense oligonucleotide may be as long as, or longer than, the length of the mRNA that is targeted.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. To inhibit expression in cells, one or more antisense oligonucleotides can be used.

Alternatively, an antisense nucleic acid can be produced biologically using an expression vector into which all or a portion of a cDNA has been subcloned in an antisense orientation (i.e., nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA. The antisense expression vector is prepared according to standard recombinant DNA methods for constructing recombinant expression vectors, except that the cDNA (or portion thereof) is cloned into the vector in the antisense orientation. The antisense expression vector can be in the form of, for example, a recombinant plasmid, phagemid or attenuated virus. The antisense expression vector can be introduced into cells using a standard transfection technique.

The antisense nucleic acid molecules of the invention are typically administered to a subject or generated in situ such that they hybridize with or bind to cellular mRNA and/or genomic DNA encoding a protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of antisense molecules, vector constructs in which the antisense nucleic acid molecule is placed under the control of a strong pol II or pol III promoter are preferred.

In one particular embodiment, antisense oligonucleotides may be employed which are complementary to one or more of the RNA silencing agents (e.g., miRNA molecules) described supra. Said anti-miRNA oligonucleotides may be DNA or RNA oligonucleotides, or they may be comprised of both ribonucleotide and deoxyribonucleotides or analogs thereof. In preferred embodiments, said anti-miRNA oligonucleotides comprise one or more (e.g., substantially all) 2'-O-methyl ribonucleotides. Such molecules are potent and irreversible inhibitors of miRNA-mediated silencing and are therefore useful for modulating RNA silencing both in vitro and in vivo. In vivo methodologies are useful for both general RNA silencing modulatory purposes as well as in therapeutic applications in which RNA silencing modulation (e.g., inhibition) is desirable. For example, insulin secretion has been shown to be regulated by at least one miRNA (Poy et al. 2004), and a role for miRNAs has also been implicated in spinal muscular atrophy (SMA; Mourelatos et al. 2002).

ii. α-Anomeric Nucleic Acid Molecules

In yet another embodiment, a nucleic acid molecule employed in the invention is an α-anomeric nucleic acid molecule. An α-anomeric nucleic acid molecule forms specific double-stranded hybrids with complementary RNA in which, contrary to the usual 1-units, the strands run parallel to each other (Gaultier et al. (1987) *Nucleic Acids. Res.* 15:6625-6641). Such a nucleic acid molecule can also comprise a 2'—O— methylribonucleotide (Inoue et al. (1987) *Nucleic Acids Res.* 15:6131-6148) or a chimeric RNA-DNA analogue (Inoue et al. (1987) *FEBS Lett.* 215:327-330).

iii. Ribozymes

In still another embodiment, a nucleic acid molecule employed in the invention is a ribozyme. Ribozymes are catalytic RNA molecules having extensive secondary structure and which intrinsically capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave mRNA transcripts to thereby inhibit translation mRNAs. A ribozyme having specificity e.g., for a RCK (or a RCK ortholog or RCK interactor)-encoding nucleic acid can be designed based upon the nucleotide sequence of the cDNA. For example, a derivative of a Tetrahymena L-19 IVS RNA can be constructed in which the nucleotide sequence of the active site is complementary to the nucleotide sequence to be cleaved in a target mRNA. See, e.g., Cech et al. U.S. Pat. No. 4,987,071 and Cech et al. U.S. Pat. No. 5,116,742. Alternatively, a target mRNA can be used to select a catalytic RNA having a specific ribonuclease activity from a pool of RNA molecules. See, e.g., Bartel, D. and Szostak, J. W. (1993) *Science* 261:1411-1418.

iv. Triple Helix Molecules

Alternatively, gene expression can be inhibited by targeting nucleotide sequences complementary to the regulatory region of a target gene to form triple helical structures that prevent transcription of a gene in target cells. See generally, Helene, C. (1991) *Anticancer Drug Des.* 6(6):569-84; Helene, C. et al. (1992) *Ann. N.Y. Acad. Sci.* 660:27-36; and Maher, L. J. (1992) *Bioassays* 14(12):807-15.

v. Nucleic Acid Vectors

In other embodiments, a nucleic acid molecule of the invention is a vector, e.g., an expression vector containing a nucleic acid encoding a gene product (or portion thereof, e.g. a protein) or an RNA silencing agent or any other nucleic acid discussed supra. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, adeno-associated viruses, retroviral vectors, and lentiviruses), which serve equivalent functions.

In certain aspects, a vector of the invention encodes an RNA silencing agent described supra, e.g., small hairpin RNAs (shRNAs). Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), Science, 296, 550-553; Lee et al, (2002). supra; Miyagishi and Taira (2002), Nature Biotechnol., 20, 497-500; Paddison et al. (2002), supra; Paul (2002), supra; Sui (2002) supra; Yu et al. (2002), supra. Such expression constructs may include one or more inducible promoters, RNA Pol III promoter systems such as U6 snRNA promoters or HI RNA polymerase III promoters, or other promoters known in the art. The constructs can include one or both strands of the RNA silencing agent. Expression constructs expressing both strands can also include loop structures linking both strands, or each strand can be separately transcribed from separate promoters within the same construct. Each strand can also be transcribed from a separate expression construct, Tuschl (2002), supra

III. Yeast Cell Wall Particles

A. Yeast Glucan Particles and Yeast Glucan-Mannan Particles

Briefly, the process for producing the glucan particles (GPs) involves the extraction and purification of the alkali-insoluble glucan particles from the yeast or fungal cell walls. The structure-function properties of the glucan particle preparation depend directly on the source from which it is obtained and also from the purity of the final product. The source of glucan particles can be yeast or other fungi, or any other source containing glucan having the properties described herein. In certain embodiments, yeast cells are a preferred source of glucans. The yeast strains employed in the present process can be any strain of yeast, including, for example, *S. cerevisiae, S. delbrueckii, S. rosei, S. microellipsodes, S. carlsbergensis, S. bisporus, S. fermentati, S. rouxii, Schizosaccharomyces pombe, Kluyveromyces polysporus, Candida albicans, C. cloacae, C. tropicalis, C. utilis, Hansenula wingei, H. arni, H. henricii, H. americana, H. canadiensis, H. capsulata, H. polymorpha, Pichia kluyveri, P. pastoris, P. polymorpha, P. rhodanensis, P. ohmeri, Torulopsis bovin*, and *T. glabrata*. Alternatively, mutant yeast strains can be employed.

The yeast cells may be produced by methods known in the art. Typical growth media comprise, for example, glucose, peptone and yeast extract. The yeast cells may be harvested and separated from the growth medium by methods typically applied to separate the biomass from the liquid medium. Such methods typically employ a solid-liquid separation process such as filtration or centrifugation. In the present process, the cells are preferably harvested in the mid-to late logarithmic phase of growth, to minimize the amount of glycogen and chitin in the yeast cells. Glycogen, chitin and protein are undesirable contaminants that affect the biological and hydrodynamic properties of the glucan particles.

Preparation of glucan particles involves treating the yeast with an aqueous alkaline solution at a suitable concentration to solubilize a portion of the yeast and form an alkali-hydroxide insoluble glucan particles having primarily $\beta(1,6)$ and $\beta(1,3)$ linkages. The alkali generally employed is an alkali-metal hydroxide, such as sodium or potassium hydroxide or an equivalent. The starting material can comprise yeast separated from the growth medium.

The treating step is performed by extracting the yeast in the aqueous hydroxide solution. The intracellular components and, optionally, the mannan portion, of the cell are solubilized in the aqueous hydroxide solution, leaving insoluble cell wall material which is substantially devoid of protein and having substantially unaltered $\beta(1,6)$ and $\beta(1,3)$ linked glucan. The intracellular constituents are hydrolyzed and released into the soluble phase. The conditions of digestion are such that at least in a major portion of the cells, the three dimensional matrix structure of the cell walls is not destroyed. In particular circumstances, substantially all the cell wall glucan remains unaltered and intact.

In certain embodiments, the aqueous hydroxide digestion step is carried out in a hydroxide solution having initial normality of from about 0.1 to about 10.0. A preferred aqueous hydroxide solution is sodium hydroxide. The digestion can be carried out at a temperature of from about 20° C. to about 121° C., for example, at about 70° C. to about 100° C. with lower temperatures requiring longer digestion times. When sodium hydroxide is used as the aqueous hydroxide, the temperature can be about 70° C., 80° C., 90° C. or about 100° C. and the solution has an initial normality of from about 0.75 to about 1.5.

Generally from about 10 to about 500 grams of dry yeast per liter of hydroxide solution is used. In certain embodiments, the aqueous hydroxide digestion step is carried out by a series of contacting steps so that the amount of residual contaminants such as proteins are less than if only one contacting step is utilized. In certain embodiments, it is desirable to remove substantially amounts of protein material from the cell. Additional extraction steps are preferably carried out in a mild acid solution having a pH of from about 2.0 to about 6.0. Typical mild acid solutions include hydrochloric acid, sodium chloride adjusted to the required pH with hydrochloric acid and acetate buffers. Other typical mild acid solutions are in sulfuric acid and acetic acid in a suitable buffer. This extraction step is preferably carried out at a temperature of from about 20° C. to about 100° C. The digested glucan particles can be, if necessary or desired, subjected to further washings and extraction to reduce the protein and contaminant levels. After processing the product pH can be adjusted to a range of about 6.0 to about 7.8.

The glucan particles can be further processed and/or further purified, as desired. For example, the glucan can be dried to a fine powder (e.g., by drying in an oven); or can be treated with organic solvents (e.g., alcohols, ether, acetone, methyl ethyl ketone, chloroform) to remove any traces or organic-soluble material, or retreated with hydroxide solution, to remove additional proteins or other impurities that may be present.

In exemplary methods, about 100 g of yeast, e.g., Bakers yeast, are suspended in about 1 L 1M NaOH and heated to about 80° C. for about 1 hour. Following centrifugation, the insoluble material is suspended in about 1 L of water and the pH adjusted to about 4-5 with HCl and incubated at about 55° C. for about 1 hour. Water and solvent washes can be carried out about 1 to 5 times.

B. Yeast Cell Wall Particle Components

A new molecular delivery system has been developed based on the use of Yeast Cell Wall Particles (YCWP). YCWP are hollow and porous 2-4 micron microspheres prepared from yeast, for example, Baker's yeast, composed primarily of beta 1,3-D-glucan, chitin, and mannoproteins. YCWP can be used to deliver a molecule of interest to a cell. A payload comprised by a yeast cell wall particle may be a nucleic acid, a protein, a drug molecule, a hormone, or any one of a wide variety of different molecular species that one desires to deliver to a cell. In some embodiments, this encapsulation system incorporates polyelectrolyte-nucleic acid nanoparticles caged within YCWP to provide for either systemic or oral administration, efficient intracellular nucleic acid delivery and release, and gene expression. Formation of the YCWP encapsulated polyelectrolyte nanoparticles follows a layer-by-layer (LbL) approach, with the different components assembled through electrostatic interactions. In some embodiments, nucleic acid payload agents for use with the invention include DNA and RNA. In some embodiments, the RNA included in the YCWP is an RNAi agent, and may be siRNA. As used herein, the term RNAi agent refers to any anionic polymer which silences RNA via the RNAi pathway. In some embodiments, the payload comprises a mix of different molecules whose delivery to cells is desired.

Robust delivery systems can be fabricated by formation of nanocomplexes composed of additional constituents. This can been demonstrated by layer-by-layer (LbL) deposition of nucleic acid and cationic polymers on different templates to fabricate colloidal particles. For example, silica, polystyrene or gold nanoparticles and biological materials can be used as templates in combination with different synthetic polymers and biopolymers. These multilayer coated particles can operate as multifunctional carriers of biologically materials, such as nucleic acid and enzymes, by two different methods. One approach can be to incorporate the delivery material as part of the multilayered structure. A second method is to utilize removable cores to encapsulate the material inside the remaining hollow polyelectrolyte shell. Both methods utilize the efficient defoliation of the polyelectrolyte layers that occurs within cells.

Embodiments of the invention feature YCWP containing nanoparticles comprising one or more elements. Nanoparticles of the invention encapsulated by YCWP can include a trapping agent and a payload molecule of interest. Additional elements of nanoparticles of the invention may include a core element of a nanoparticle. In preferred embodiments, the nanoparticle is formed around a core comprising an inert nucleic acid, such as tRNA or scrambled RNA, and a trapping agent. Other exemplary core components include, but are not limited to, anionic polysaccharides, proteins, synthetic polymers and inorganic matrices. Exemplary trapping agents are cationic agents and can include, but are not limited to, cationic polysaccharides, proteins and synthetic polymers.

The layer-by-layer (LbL) self-assembly of materials held together by electrostatic interactions is a facile method for the fabrication of nanomaterials with potential applications in gene therapy. Some embodiments of the invention feature YCWP comprising multilayered structures. Characterization of LbL structures on planar 2D or 3D surfaces is possible by a variety of techniques, but most of these techniques are not amenable to characterize multilayered structures inside YCWP. The quantitative characterization of YCWP encapsulated polyelectrolyte nanoplex formation within YCWP can be approached by selectively labeling each layer of the multilayered nanocomplex with fluorescent markers to optimize experimental conditions for preparation of these complexes inside YCWP. Embodiments of the invention feature layers comprising a trapping molecule for the payload, which can be a cationic agent, such as an agent used to prepare nucleic acids for transfection into cells; an inert nucleic acid, such as tRNA; and/or a payload molecule, which may be a nucleic acid, such as DNA and/or RNA, a protein, a tracing molecule, such as a dye molecule and/or other molecules or molecular species as desired for delivery to cells.

Evaluation of the different layers inside the YCWP was characterized by qualitative fluorescent microscopy and quantitative fluorescent spectroscopy and flow cytometry. As seen below in the Examples section, in some embodiments, the layer-by-layer formation and characterization of nanoparticles synthesized inside YCWP is described as leading to the optimization of this nucleic acid delivery system for mammalian cell transfection.

Embodiments of the invention feature nanocomplexes and nanoparticles comprising a payload trapping molecule. In some embodiments, the trapping molecule is a cation, such as a cationic polymer. One effective synthetic cationic polymer is polyethylenimine (PEI), a commercially available compound that has been used for gene delivery. Some embodiments of the invention utilize PEI has a high positive charge that allows efficient condensation of anionic nucleic acids. The presence of amines (only 15-20% are protonated at physiological pH) contributes to a proton-sponge mechanism, which is believed to mediate endosomal DNA release and responsible for its high DNA transfection activity. Some embodiments feature strategies and/or ingredients that facilitate the creation and/or the function of the nanocomplexes and nanoparticles. Other strategies previously reported to enhance transfection efficiency, used copolymers in addition to PEI, such as EndoPortemm, and hyaluronic acid in the DNA layer to facilitate defoliation and endosomal DNA release, and Penetratin, a cationic peptide containing a nuclear localization signal to enhance DNA nuclear uptake.

The use of PEI, however, can be limited by its toxicity. The toxicity of PEI can be reduced by washing the PEI-coated YCWP caged nanoplexes/nanoparticles to remove any unbound PEI. Alternatively, lower ratios of PEI can be used, for example, in lieu of washing. Several studies have identified other potentially useful cationic polymers as gene-delivery vectors with the advantages of decreased toxicity and higher gene delivery efficiency than PEI. For example toxicity of PEI can be significantly reduced by partial acetylation of amine groups, or polymers constructed from biodegradable ester units. Some embodiments utilize more than one trapping agent, such as two or more cationic agents. Some embodiments of the invention feature nanoparticles/nanocomplexes that utilize one or more non-PEI cationic agents, with or without concurrent usage of PEI.

The payload trapping molecule is preferably a pharmaceutically acceptable excipient. The payload and trapping molecule are both soluble in a solvent system. The payload and trapping molecule are preferably water soluble. In preferred embodiments, the trapping molecule is biodegradable.

Embodiments of the invention feature a variety of mechanisms by which a payload is incorporated by the trapping molecules. The mechanism of action of the trapping reaction with a given payload dictates the choice of payload trapping molecule. For electrostatic interactions, a charged payload trapping molecule of opposite charge of the payload is preferred. For physical entrapment, the payload trapping molecule suitably participates in the formation of a matrix that reduces the diffusion of a payload. In other embodiments, the payload trapping molecule contributes a hydrophobic binding property that contributes to the retention of the payload. In further embodiments, the payload trapping molecule selectively binds to the payload, providing an affinity interaction that contributes to the retention of the payload.

In general, polyelectrolytes can be suitable payload trapping molecules. Several suitable polyelectrolytes are disclosed in U.S. Pat. No. 6,133,229. In some embodiments, the polyelectrolyte may be a cationic or anionic polyelectrolyte. Amphoteric polyelectrolytes may also be employed. The cationic polyelectrolyte is preferably a polymer with cationic groups distributed along the molecular chain. The cationic groups, which in certain embodiments may include quaternary ammonium-derived moieties, may be disposed in side groups pendant from the chain or may be incorporated in it. Examples of cationic polyelectrolytes include: copolymers of vinyl pyrollidone and quaternary methyl methacrylate e.g., GAFQUAT® series (755N, 734, HS-100) obtained from ISP; substituted polyacrylamides; polyethyleneimine, polypropyleneimine and substituted derivatives; polyamine homopolymers (GOLCHEM® CL 118); polyamine co-polymers (e.g., condensates of epichlorohydrin and mono or dimethylamine); polydiallyl dimethyl ammonium chloride (polyDADMAC); substituted dextrans; modified guar gum (substituted with hydroxypropytrimonium chloride); substituted proteins (e.g., quaternary groups substituted on soya protein and hydrolysed collagen); polyamino acids (e.g., polylysine); low molecular weight polyamino compounds (e.g., spermine and spermidine). Natural or artificial polymers may be employed. Cationic polyelectrolytes with MW 150 to 5,000,000, preferably 5000 to 500,000, more preferably 5000 to 100,000 may be employed. An amount of 0.01 to 10% is preferred, more preferably 0.1 to 2% w/v, especially 0.05 to 5%.

The anionic polyelectrolyte is preferably a polymer with anionic groups distributed along the molecular chain. The anionic groups, which may include carboxylate, sulfonate, sulphate or other negatively charged ionisable groupings, may be disposed upon groups pendant from the chain or bonded directly to the polymer backbone. Natural or artificial polymers may be employed.

Examples of anionic polyelectrolytes include: a copolymer of methyl vinyl ether and maleic anhydride, a copolymer of methyl vinyl ether and maleic acid, (Gantrez AN-series and S-series, respectively, International Specialty Products, Wayne, N.J.); alginic acid and salts; carboxymethyl celluloses and salts; substituted polyacrylamides (eg substituted with carboxylic acid groups); polyacrylic acids and salts; polystyrene sulfonic acids and salts; dextran sulphates; substituted saccharides e.g., sucrose octosulfate; heparin. Anionic polyelectrolytes with MW of 150 to 5,000,000 may be used, preferably 5000 to 500,000, more preferably 5000 to 100,000. An amount of 0.01% to 10% is preferred especially 0.05 to 5% more especially 0.1 to 2% w/v.

Biological polymers, such as polysaccharides, are preferred trapping polymers. Preferably, the polymers are processed to an average molecular weight to less than 100,000 Daltons. The polymers are preferably derivatized to provide cationic or anionic characteristics. Suitable polysaccharides include chitosan (deacetylated chitin), alginates, dextrans, such as 2-(diethylamino) ethyl ether dextran (DEAE-dextran) and dextran sulphate, xanthans, locust bean gums and guar gums.

Two general classes of cationic molecules are suitable for use as trapping molecules with negatively charged payloads such as polynucleotides: cationic polymers and certain cationic lipids.

A wide variety of cationic polymers have been shown to mediate in vitro transfection, ranging from proteins [such as histones (Fritz, J. D., et al, (1996) Hum. Gene Ther. 7, 1395-1404) and high mobility group (HMG) proteins (Mistry A. R., et al. (1997) BioTechniques 22, 718-729)] and polypeptides [such as polylysine (Wu, G. Y. & Wu, C. H. (1987) J. Biol. Chem. 262, 4429-4432, Wagner, E., et al., (1991) Bioconjugate Chem. 2, 226-231, short synthetic peptides (Gottschalk, S., et al., (1996) Gene Ther. 3, 448-457; Wadhwa, M. S., et al., (1997) Bioconjugate Chem. 8, 81-88), and helical amphiphilic peptides (Legendre, J. Y., et al., (1997) Bioconjugate Chem. 8, 57-63; Wyman, T. B., et al., (1997) Biochemistry 36, 3008-3017)] to synthetic polymers [such as polyethyleneimine (Boussif, O., et al., (1996) Gene Ther. 3, 1074-1080), cationic dendrimers (Tang, M. X., et al., (1996) Bioconjugate Chem. 7, 703-714; Haensler, J. et al., (1993) Bioconjugate Chem. 4, 372-379), and glucaramide polymers (Goldman, C. K., et al., (1997) Nat. Biotech. 15, 462-466)]. Other suitable cationic polymers include N-substituted glycine oligomers (peptoids) (Murphy, J. E., et al, A combinatorial approach to the discovery of efficient cationic peptoid reagents for gene delivery, Proc Natl Acad. Sci. USA, 1998 95 (4) 1517-1522), poly(2-methyl-acrylic acid 2-[(2-dimethylamino)-ethyl)-methyl-amino]-ethyl ester), abbreviated as pDAMA, and poly(2-dimethylamino ethyl)-methacrylate (pDMAEMA) (Funhoff, A. M., et al., 2004 Biomacromolecules, 5, 32-39).

Cationic lipids are also known in the art to be suitable for transfection. Felgner, P. Ll, et al., Lipofection: a highly efficient, lipid-mediated DNA-transfection procedure. Proc Natl Acad Sci USA. 1987 84 (21):7413-7. Suitable cationic lipids include N-[1-(2,3-dioleyloxy)pro-pyl]-N,N,N-trimethylammonium chloride (DOTMA), [N,N,N',N'-tetramethyl-N,N'-1-bis(2-hydroxyethyl)-2,3-di(oleoyloxy)-1,4-butanediammonium iodide] (Promega Madison, Wis., USA), dioctadecylamidoglycyl spermine (Promega Madison, Wis., USA), N-[1-(2,3-Dioleoyloxy)]-N,N,N-trimethylammonium propane methylsulfate (DOTAP), N-[1-(2,3-dioleyloxy)propyl]-N,N,N-trimeth-ylammonium chloride, 1,2-dimyristyloxypropyl-3-dimethyl-hydroxy ethyl ammonium bromide (DMRIE), dimyristoleoyl phosphonomethyl trimethyl ammonium (DMPTA) (see Floch et al. 1997. Cationic phosphonolipids as non-viral vectors for DNA transfection in hematopoietic cell lines and CD34+ cells. Blood Cells, Molec. & Diseases 23: 69-87), 1,2-dioleoyl-sn-glycero-3-phosphoethanolamine-N-(7-nitro-2-1,3-benzoxadia-zol-4-yl), ammonium salt (Avanti Polar Lipids, Inc. Alabaster, Ala., US), 1,2-dioleoyl-3-trimethylammonium-propane chloride (Avanti Polar Lipids, Inc. Alabaster, Ala., US), 1,2-dioleoyl-sn-glycero-3-phosphoethanolamine (Avanti Polar Lipids, Inc. Alabaster, Ala., US) and 1,3-dioleoyloxy-2-(6-carboxyspermyl)propylamide (DOSPER).

Cores and/or layers of the delivery systems of the invention can further include co-polymers that facilitate other functions. For example, co-polymers facilitating endosomal release of payloads can by included. An exemplary co-polymer facilitating endosomal release is Endoporter (Summerton J E. *Ann N Y Acad Sci*. 1058:62-75 (2005), hereby incorporated by reference in its entirety). In some embodiments, co-polymers facilitating nuclear localization can be included, for example, in one or more payload layers. In some embodiments, co-polymers can be included which facilitate defoliation kinetics can be included. For example, hyluronic acid or glutamic acid can be included as an anionic core polymer, facilitating defoliation kinetics and/or payload release. Additional co-polymers include, but are not limited to heparin sulfate, and the like.

Embodiments of the invention also include nanocomplexes and nanoparticles comprising decreased amounts of payload trapping molecule. For example, in one embodiment of the invention, up to 100 µg of payload nucleic acid is added per $1 \times 10^9$ YCWP with tRNA/PEI cores; a trapping molecule (e.g., PEI) is then added at a trapping molecule/nucleic acid ratio of 2.5 to coat the nucleic acid/tRNA-PEI core. In other embodiments of the invention, a lower amount of the trapping molecule is used, for a trapping molecule/nucleic acid ratio of 2.25, 2.1, 2.0, 1.9, 1.8, 1.7, 1.6, 1.5, 1.4, 1.3, 1.2, 1.1, 1.0.0.9, 0.8, 0.7, 0.6, 0.5, 0.4, 0.3, 0.2, 0.1, 0.05, 0.025, 0.01, 0.005, 0.0025 or 0.0001.

Embodiments of the invention also include nanocomplexes and nanoparticles wherein a trapping molecule/layer is not applied to the YCWP/tRNA-PEI core/payload nucleic acid complex. Additional embodiments include nanocomplexes and nanoparticles wherein a payload molecule is incorporate directly into the core, with or without tRNA. Additional embodiments include nanocomplexes and nanoparticles wherein a compound facilitating endosomal release (e.g., EndoPorter) is included.

C. YCWP for Molecular Delivery

The development of gene therapy relies on the design of optimal systems for the delivery and the expression and/or activity of nucleic acid agents, such as DNA and RNA, including siRNA. Gene delivery systems have been developed based on recombinant viruses, and non-viral vectors such as cationic polymers and lipids. Embodiments of the invention feature the use of YCWP as a delivery system, to deliver nucleic acid payload agents, other nucleic acids and/ or other payload molecules to cells.

Embodiments of the invention feature particles for the administration of at least one polynucleotide. In some embodiments, the one or more polynucleotides may be DNA or RNA, such as a cDNA, a ribozyme or other catalytic RNA, siRNA, miRNA, shRNA, and the like. In some embodiments, the particles of the present invention are used to administer at least one polynucleotide encoding a gene product of a missing gene, wherein the expression of the gene product is useful in the treatment of the genetic disorder or the genetic component of a condition. In preferred embodiments, the particles of the present invention include an RNA that will reduce the activity of one or more proteins in a subject to whom the particles are administered, for example, by gene silencing (e.g., by RNAi). In some embodiments, the particles will include an siRNA. In preferred embodiments, particles containing siRNA contain siRNA that has sequence complementary to the mRNA of a gene involved in an inflammatory response.

Encapsulated particles of the invention may comprise a nanoparticle core comprising a core agent and trapping agent. In some embodiments, the core has a trapping layer. Encapsulated particles of the invention may comprise a nanoparticle comprising more than one layer. Encapsulated nanoparticles of the invention can include a core element in the nanoparticle, such a core element being suitable for the addition of molecules to the surface of the core, such that a new layer or section to the nanoparticle is created. In some embodiments, the addition of molecules to the core complex, comprising the core and any layer that was previously added to the core, can be done one or more times, to create a subsequent layers or sections further outside from the center of the core. Initial and subsequent layers or sections may have the same compositions or may have different compositions. In some embodiments, a layer or section added to a core complex may contain a trapping molecule. In some embodiments, a layer or section added to a core complex may contain a payload agent, comprising a payload molecule and/or a nucleic acid payload agent. A multilayer encapsulated particle of the invention may have one or more layers that consist essentially of a payload substance trapped by a trapping layer, and/or comprising a mixture of payload molecules, trapping molecules, and/or other molecules. In some embodiments, nanoparticles of the invention may comprise two or more payload molecules, mixed together essentially uniformly. In some embodiments, various distinct layers of the particles comprising separate payload molecules or separate mixtures of one or more payload molecules.

Embodiments of the invention feature multilayered nanoparticles within yeast cell wall components, wherein the multilayered nanoparticles are designed to have a more interior part and a more exterior part. These parts may have distinct compositions and the compositions of the layers may contain one or more constituent molecular species in common. In some embodiments, different layers of the multilayered nanoparticles comprise different payload molecules and/or nucleic acid payload agents. For example, two layers of a nanoparticle may contain distinct nucleic acid molecules. In some embodiments, multilayered nanoparticles comprise more than one trapping molecule. Some nanoparticles of the invention comprise two or more trapping molecules and some multilayered nanoparticles comprise two or more trapping molecules wherein the molecules are found in separate layers or sections of the particle and/or are found in different relative amounts in distinct areas, layers or sections of the particle.

In some encapsulated nanoparticles of the invention, the two or more payload molecules will be found in separate layers or sections of the particle and/or are found in different relative amounts in distinct areas, layers or sections of the particle. In some embodiments, one or more payload molecules will be found in a more exterior section or layer than one or more payload molecules, and/or one or more payload molecules will be found predominantly in a more exterior section or layer than one or more payload molecules.

Multilayered nanoparticles of the invention can feature different payloads in outer layers, interior layers or intervening layers. Outer layers, interior layers and intervening layers may comprising unique payload molecules, unique trapping molecules and/or distinct formulations of trapping molecules, payload molecules or other molecules, as compared to other layers and/or other nanoparticles.

Design of nanoparticles of the invention can influence the kinetics of payload release from the YCWP. In some embodiments of the invention, the rate at which the introduction of payload molecules into the cell from a YCWP that has been contacted with or incorporated by the cell can be adjusted by adjusting the design of the nanoparticles of the YCWP. The relative time and speed with which one or more payload molecules is released can depend on the structure and formulation of the encapsulated nanoparticles included in the YCWP. While not wishing to be bound by any particular theory or model, the release of payload molecules from the exterior of a nanoparticle or from a layer or section at or near the exterior of the nanoparticle will occur sooner and at a faster rate than the release of payload molecules from the interior of the particle or from a layer or section at or near to the center, the core or the core complex of the nanoparticle. In some embodiments, multilayered nanoparticles will lose outer layers of the particle first, which dissolve or disperse into the surrounding media or cytoplasmic matrix, releasing the payload molecules contained within the layer. The release and/or dissolution of an exterior layer or section permits the contacting of a more interior layer with the medium surrounding the particle. Once contacted with the medium surrounding the particle, the release of a payload molecule from the more interior layer or section will begin or will speed up. Some embodiments feature intervening layers or sections without a payload molecule. Some embodiments featuring layers without a payload molecule or payload agent will feature layers or section consisting essentially of trapping molecules or agents. The sequential loss of exterior layers followed by interior layers is part of the process of defoliation of the particle and mirrors in reverse the layer-by-layer construction of the particle. Generally, payload molecules found in exterior layers will be released sooner and faster than payload molecules found in interior layers. This feature of the invention can be utilized, for example, when delivering multiple payloads. For example, therapeutic payloads suitable for acute action can be formulated in exterior layers and therapeutic payloads suitable for chronic action can be formulated in interior layers and/or payload cores. The process of defoliation permits encapsulated nanoparticle delivery systems of the invention to deliver two or more payload molecules at different times and/or rates than each other. In some embodiments, two or more payload molecules or agents are released at the same time or rate or at similar times and rates. In some embodiments, cores can be designed such that they release payload at a fast rate, for example, bursting upon an appropriate environmental cue.

Some embodiments of the invention feature nanoparticles designed with one or more payload molecules in separate layers or sections. This permits the release of one or more payload molecule species at different times and/or rates relative to one another. Each payload molecule incorporated into nanoparticles of the invention can have its own kinetic release profile. One or more payload molecules can share a kinetic release profile. In some embodiments, nanoparticles are designed so that one or more payload molecules or agents is released sooner or faster than other payload molecules or agents in the particle. In some embodiments, nanoparticles are designed so that one or more payload molecules or agents is released sooner or faster than payload molecules or agents from other nanoparticles in the same YCWP or from other nanoparticles in other YCWP.

In a preferred embodiment, glucan particles are purified from Baker's yeast by a series of alkaline and solvent extractions hydrolyzing outer cell wall and intracellular components yielding purified, porous 2-4 micron, hollow beta 1,3-D-glucan particles (FIG. 1c). Empty glucan particles are then labeled with fluorescein to track the glucan shells. Cationic cores are synthesized inside the glucan shells by absorbing a sub-saturating volume of yeast tRNA to partially swell the particles followed by reaction with an excess of polyethyleneimine (PEI) to form encapsulated complexed cationic cores as evidenced by the phase distinct structures within the fluorescent glucan shells. Layer by layer synthesis methods can then be used to absorb anionic Dy547-labeled siRNA onto the cationic surface of the cores followed by a final coat of PEI, as seen by the fluorescent siRNA (red) inside the fluorescent glucan shells (green) in the confocal image on the far right bottom (FIG. 1c).

The encapsulated particulate delivery system of the present invention is useful for in vivo or in vitro delivery of payload molecules including, but not limited to, polynucleotides such as oligonucleotides, antisense constructs, siRNA, miRNA, shRNA, enzymatic RNA, and recombinant DNA constructs, including expression vectors.

In exemplary embodiments, nucleic acid can be included in particles at a ratio of about 0.001-2000 ug per 109 particles, for example, about 0.005-1000 ug or 1-100 ug per 109 particles, e.g., 50 ug-100 ug, 25-50 ug, 5-25 ug or 1-12 ug per 109 particles (e.g., 5, 7.5, 10, 12, 12.5, 15, 20 or 25 ug per 109 particles).

i. siRNA Delivery

Preferred embodiments of the invention include YCWP for the delivery of siRNA to cells. One or more siRNAs may be found in the encapsulated nanoparticles of these embodiments. The nanoparticles may be essentially uniform throughout the particle or may comprise separate layers or sections. Separate layers or sections of a nanoparticle may consist of essentially one molecular component and may have separate formulas for one another.

Embodiments of the invention feature the incorporation of siRNAs into nanoparticles that are further encapsulated in YCWP. siRNAs may be found in nanoparticles that are essentially uniform throughout the particle or that have various layers or sections. siRNAs can be localized to a particular layer in a multilayered nanoparticle. Some embodiments of the invention contain two or more siRNA species, which may be localized to the same or different locations within the particle.

Through particular nanoparticle designs, the timing and/or the rate of release of siRNAs from the YCWP can be modulated. Some embodiments of the invention feature siRNAs interior to the nanoparticle from an exterior layer comprising essentially one or more trapping molecules. One or more siRNA species may be found in separate layers or sections of a nanoparticle, which can lead to different timing and rate of release for different siRNAs.

In some embodiments of the invention, particles include a cationic core comprising tRNA coated with PEI (e.g., about 50 ug tRNA per $5 \times 10^8$ YCWPs coated or trapped with excess PEI), an siRNA layer (optionally including EndoPorter (e.g., about 1-10 ug EndoPorter per $10^7$-$10^8$ particles) (as a colayer), and a PEI trapping layer (e.g., 5-100 ug per $10^7$-$10^8$ particles).

Exemplary particles are formed according to the methods described in the Examples, infra. Particles can be formulated to include high concentrations or amounts of silencing agent. For example, particles can be formulated to include up to 15 µg, 20 µg, 25 µg, 30 µg, 40 µg, 50 µg, or more silencing agent (e.g., siRNA) per $1 \times 10^9$ YCWP. However, concentration or amounts included are routinely lowered due to the high efficiency of delivery provided by this system, e.g., 1-12 µg silencing agent per $1 \times 10^9$ particles of YCWP. Exemplary amounts or concentrations of siRNA can include 10-1000 pmol/$5 \times 10^7$ particles, e.g., 20, 40, 100, 200 of 500 pmol siRNA/$5 \times 10^7$ particles.

Amounts can also vary depending on the nature of the particle delivery. For example, in vitro delivery to cells (e.g., $10^6$ cells) can feature contacting cells with 40 pmol siRNA/107 particles (or $40 \times 10^{-7}$ pmol siRNA/particle), I.P. delivery can feature administering 40 pmol siRNA/107 particles (or $8 \times 10^{-7}$ pmol/particle). Oral delivery can feature administering 40 pmol siRNA/$1 \times 10^7$ particles (or $4 \times 10^{-7}$ pmol/particle). Exemplary embodiments feature administering particles contains from about $1 \times 10^{-7}$ to about $500 \times 10^{-7}$ pmol siRNA/particle. The delivery systems of the invention, however, are believed to be capable of delivering significantly higher amounts of siRNA.

I.P. delivery to animals can feature administering about 40 pmol siRNA in $5 \times 10^7$ particles (100 µg particles) and oral delivery to animals can feature administering about 40 or more pmol siRNA in $1 \times 10^8$ particles (200 µg particles).

Delivery can also be tailored based on the desired amount of siRNA to be administered per kg animal. For example, delivery of about 0.01-1 mg/kg, 0.05-5 mg/kg, 0.1-0.35 mg/kg or, for example, 0.25 mg (40 pmol) siRNA/kg may be desirable.

ii. DNA Delivery

In preferred embodiments, the present invention provides compositions and methods for the treatment of genetic disorders or conditions having a genetic component. In further preferred embodiments, the present invention provides compositions useful for the manufacture of pharmaceutical products for the treatment of genetic disorders or conditions having a genetic component. Embodiments of the invention include YCWP compositions for the delivery of nucleic acid payload agents, as described supra, and/or other payload molecules.

Both environmental and genetic factors have roles in the development of any disease. A genetic disorder is a disease caused by abnormalities in an individual's genetic material (genome). There are four different types of genetic disorders: (1) single-gene, (2) multifactorial, (3) chromosomal, and (4) mitochondrial.

1) Single-gene (also called Mendelian or monogenic)—This type is caused by changes or mutations that occur in the DNA sequence of one gene. Genes code for proteins, the molecules that carry out most of the work, perform most life functions, and even make up the majority of cellular structures. When a gene is mutated so that its protein product can no longer carry out its normal function, a disorder can result. There are more than 6,000 known single-gene disorders, which occur in about 1 out of every 200 births. Some examples are cystic fibrosis, sickle cell anemia, Marfan syndrome, Huntington's disease, and hereditary hemochromatosis.

2) Multifactorial (also called complex or polygenic)—This type is caused by a combination of environmental factors and mutations in multiple genes. For example, different genes that influence breast cancer susceptibility have been found on chromosomes 6, 11, 13, 14, 15, 17, and 22. Its more complicated nature makes it much more difficult to analyze than single-gene or chromosomal disorders. Some of the most common chronic disorders are multifactorial disorders. Examples include heart disease, high blood pressure, Alzheimer's disease, arthritis, diabetes, cancer, and obesity. Multifactorial inheritance also is associated with heritable traits such as fingerprint patterns, height, eye color, and skin color.

3) Chromosomal—Chromosomes, distinct structures made up of DNA and protein, are located in the nucleus of each cell. Because chromosomes are carriers of genetic material, such abnormalities in chromosome structure as missing or extra copies or gross breaks and rejoinings (translocations), can result in disease. Some types of major chromosomal abnormalities can be detected by microscopic examination. Down syndrome or trisomy 21 is a common disorder that occurs when a person has three copies of chromosome 21.

4) Mitochondrial—This relatively rare type of genetic disorder is caused by mutations in the nonchromosomal DNA of mitochondria. Mitochondria are small round or rod-like organelles that are involved in cellular respiration and found in the cytoplasm of plant and animal cells. Each mitochondrion may contain 5 to 10 circular pieces of DNA.

In preferred embodiments, the encapsulated particulate delivery system of the present invention is used to administer at least one polynucleotide comprising a compensating gene. In other preferred embodiments, the particulate delivery system of the present invention is used to administer at least one polynucleotide encoding a gene product of a missing gene, wherein the expression of the gene product is useful in the treatment of the genetic disorder or the genetic component of a condition.

In aspects of the present invention that relate to gene therapy, the nucleic acid compositions contain either compensating genes or genes that encode therapeutic proteins. Examples of compensating genes include a gene that encodes dystrophin or a functional fragment, a gene to compensate for the defective gene in patients suffering from cystic fibrosis, a gene to compensate for the defective gene in patients suffering from ADA, and a gene encoding Factor VIII. Examples of genes encoding therapeutic proteins include genes which encodes erythropoietin, interferon, LDL receptor, GM-CSF, IL-2, IL-4 and TNF. Additionally, nucleic acid compositions which encode single chain antibody components which specifically bind to toxic substances can be administered.

DNA particles can be formulated in a manner similar to section i, supra. DNA can be included at, for example, 10-2000 ng/$10^6$ particles.

iii. Delivery of Other Payloads

Embodiments of the invention feature YCWP capable of delivering a wide variety of different molecules to cells, individually or in combination.

In some preferred embodiments, the encapsulated particulate delivery system of the present invention is useful for in vivo or in vitro delivery of payload molecules such as amino acids, peptides and proteins. By "protein" is meant a sequence of amino acids for which the chain length is sufficient to produce the higher levels of tertiary and/or quaternary structure. This is to distinguish from "peptides" or other small molecular weight drugs that do not have such structure. Typically, the protein herein will have a molecular weight of at least about 15-20 kD, preferably at least about 20 kD.

In some embodiments, the protein payload molecule is preferably essentially pure and desirably essentially homogeneous (i.e. free from contaminating proteins etc). "Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition. Proteins may be derived from naturally occurring sources or produced by recombinant technology. Proteins include protein variants produced by amino acid substitutions or by directed protein evolution (Kurtzman, A. L., et al., Advances in directed protein evolution by recursive genetic recombination: applications to therapeutic proteins, Curr Opin Biotechnol. 2001 12 (4): 361-70) as well as derivatives, such as PEGylated proteins.

In certain embodiments, the protein is an antibody. The antibody may bind to any of the above-mentioned molecules, for example. Exemplary molecular targets for antibodies encompassed by the present invention include CD proteins such as CD3, CD4, CD8, CD19, CD20 and CD34; members of the HER receptor family such as the EGF receptor, HER2, HER3 or HER4 receptor; cell adhesion molecules such as LFA-1, Mol, p150,95, VLA-4, ICAM-1, VCAM and alphav/beta3 integrin including either alpha or beta subunits thereof (e.g. anti-CD11a, anti-CD18 or anti-CD11b antibodies); growth factors such as VEGF; IgE; blood group antigens; flk2/flt3 receptor; obesity (OB) receptor; protein C, etc.

In addition to peptides, polypeptides and polynucleotides, the particulate delivery system of the present invention is suitable for the delivery of smaller molecules, preferably for the delivery of pharmaceutically active agent, more preferably therapeutic small molecules. Suitable small molecule payloads for the delivery system of the present invention include contraceptive agents such as diethyl stilbestrol, 17-beta-estradiol, estrone, ethinyl estradiol, mestranol, and the like; progestins such as norethindrone, norgestryl, ethynodiol diacetate, lynestrenol, medroxyprogesterone acetate, dimethisterone, megestrol acetate, chlormadinone acetate, norgestimate, norethisterone, ethisterone, melengestrol, norethynodrel and the like; and spermicidal compounds such as nonylphenoxypolyoxyethylene glycol, benzethonium chloride, chlorindanol and the like. Preferably, for such steroidal payloads, a mixture of trapping molecules is used, comprising a sufficient amount of a detergent to solubilize the payload and a polymer to retain the payload within the yeast cell wall particle.

Other active agents that can be incorporated in the delivery system of the present invention include gastrointestinal therapeutic agents such as aluminum hydroxide, calcium carbonate, magnesium carbonate, sodium carbonate and the like; non-steroidal antifertility agents; parasympathomimetic agents; psychotherapeutic agents; major tranquilizers such as chloropromazine HCl, clozapine, mesoridazine, metiapine, reserpine, thioridazine and the like; minor tranquilizers such as chlordiazepoxide, diazepam, meprobamate, temazepam and the like; rhinological decongestants; sedative-hypnotics such as codeine, phenobarbital, sodium pentobarbital, sodium secobarbital and the like; other steroids such as testosterone and testosterone propionate; sulfonamides; sympathomimetic agents; vaccines; vitamins and nutrients such as the essential amino acids, essential fats and the like; antimalarials such as 4-aminoquinolines, 8-aminoquinolines, pyrimethamine and the like; anti-migraine agents such as mazindol, phentermine and the like; anti-Parkinson agents such as L-dopa; anti-spasmodics such as atropine, methscopolamine bromide and the like; antispasmodics and anticholinergic agents such as bile therapy, digestants, enzymes and the like; antitussives such as dextromethorphan, noscapine and the like; bronchodilators; cardiovascular agents such as anti-hypertensive compounds, Rauwolfia alkaloids, coronary vasodilators, nitroglycerin, organic nitrates, pentaerythritotetranitrate and the like; electrolyte replacements such as potassium chloride; ergotalkaloids such as ergotamine with and without caffeine, hydrogenated ergot alkaloids, dihydroergocristine methanesulfate, dihydroergocomine methanesulfonate, dihydroergokroyptine methanesulfate and combinations thereof; alkaloids such as atropine sulfate, Belladonna, hyoscine hydrobromide and the like; analgesics; narcotics such as codeine, dihydrocodienone, meperidine, morphine and the like; non-narcotics such as salicylates, aspirin, acetaminophen, d-propoxyphene and the like.

In preferred embodiments, the system of the present invention is used to deliver antibiotics such as the cephalosporins, chloramphenical, gentamicin, kanamycin A, kanamycin B, the penicillins, ampicillin, streptomycin A, antimycin A, chloropamtheniol, metronidazole, oxytetracycline penicillin G, the tetracyclines, and the like. In preferred embodiments, the ability of the body's macrophages to inactivate pathogens is enhanced by the delivery of antibiotics, such as tetracycline, to the macrophages.

In other preferred embodiments, the present invention provides a system to deliver anti-cancer agents; anti-convulsants such as mephenyloin, phenobarbital, trimethadione; anti-emetics such as thiethylperazine; antihistamines such as chlorophinazine, dimenhydrinate, diphenhydramine, perphenazine, tripelennamine and the like; anti-inflammatory agents such as hormonal agents, hydrocortisone, prednisolone, prednisone, non-hormonal agents, allopurinol, aspirin, indomethacin, phenylbutazone and the like; prostaglandins; cytotoxic drugs such as thiotepa, chlorambucil, cyclophosphamide, melphalan, nitrogen mustard, methotrexate and the like.

In other embodiments, the system can be used to deliver enzymes such as ribonuclease, neuramidinase, trypsin, glycogen phosphorylase, sperm lactic dehydrogenase, sperm hyaluronidase, adenossinetriphosphatase-, alkaline phosphatase, alkaline phosphatase esterase, amino peptidase, trypsin chymotrypsin, amylase, muramidase, acrosomal proteinase, diesterase, glutamic acid dehydrogenase, succinic acid dehydrogenase, beta-glycophosphatase, lipase, ATP-ase alpha-peptate gamma-glutamylotranspeptidase, sterol-3-beta-ol-dehydrogenase, DPN-di-aprorase.

In preferred embodiments, the system can deliver antigens of bioterrorism critical biological agents. In preferred embodiments, the system can be used to deliver inactivated antigenic toxins, such as anatoxin antigens, including toxoids (inactivated but antigenic toxins), and toxoid conjugates. A wide variety of payloads that can be incorporated into embodiments of the invention are described in U.S. Patent Application No. 2005/0281781, to Ostroff, hereby incorporated by reference.

IV. siRNA Targets

A. Inflammatory Signaling Pathway Targets

Inflammation is a mechanism that protects mammals from invading pathogens and disease. However, while acute inflammation is necessary to protect a mammal from infection, chronic inflammation causes tissue damage and is the underlying cause of many illnesses, including metabolic diseases and disorders. The role of inflammation in metabolic disorders is believed to be due, at least in part, activation of inflammatory signaling in adipose tissue, both in the adipocyte cell population and in infiltrating macrophage populations within the adipose tissue. Inflammatory signaling activates both IKKβ/NF-κB and JNK pathways during metabolic dysregulation and can lead to increased expression of further inflammation mediators and markers. Activation of inflammatory pathways has been linked to obesity (i.e., obesity induces the inflammatory state in insulin responsive tissues) and is believed to be responsible, at least in part, for insulin resistance associated with type 2 diabetes. Accordingly, pharmacological intervention with inflammatory activity is believed to be a desirable target for treatment of metabolic diseases and disorders.

Examples of metabolic disorders that involve inflammation include obesity, type I diabetes, type II diabetes, atherosclerosis, Crohn's Disease/IBD, arthritis, AIDS (in which it is thought that HIV is harbored in macrophages when it is blocked from replicating in other cells in long term disease), hyperphagia, hypophagia, endocrine abnormalities, triglyceride storage disease, Bardet-Biedl syndrome, Lawrence-Moon syndrome, Prader-Labhart-Willi syndrome, Keams-Sayre syndrome, anorexia, medium chain acyl-CoA dehydrogenase deficiency, and cachexia.

The instant invention provides methods of treating metabolic disorders by decreasing inflammation through the targeting of inflammatory signaling pathway genes. Embodiments of the invention feature the targeting of particular genes through the delivery of nucleic acid payload agents to cells (e.g., silencing). Many of these genes involve regulated inflammatory processes that are mediated by macrophages and other cells that undergo phagocytosis and enhance immune responses. Preferred gene targets are gene products within macrophages. Especially preferred gene targets include TNFα, Map4k4, RIP140, and TLR4.

i. TNFα

Tumor necrosis factor (TNF) alpha is a cytokine which acts through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, sixteen members of the TNF ligand superfamily have been identified and seventeen members of the TNF-receptor superfamily have been characterized.

TNFα is a cytokine secreted by macrophages and adipocytes that contributes to the low grade inflammation and insulin resistance observed in obesity. TNFα signaling decreases PPARγ and GLUT4 glucose transporter expression in adipocytes, impairing insulin action, which is mediated in part by the yeast Step 20 protein kinase ortholog Map4k4 (see, e.g., Tang et al., Proc. Natl. Acad. Sci. U.S.A., 103(7): 2087-2092, 2006, the entire contents of which are incorporated herein by reference). TNFα selectively stimulates the expression of a key component of its own signaling pathway, Map4k4, through a TNFR1-dependent mechanism that targets the transcription factors cJUN and ATF2 (Tesz et al., J. Biol. Chem., 282(27):19302-19312, 2007, the entire contents of which are incorporated herein by reference). As described in more detail in the Examples, silencing of TNFα successfully depletes of TNFα in macrophages, leading to a decrease in inflammation. Thus, inhibition of TNFα expression may be used to treat metabolic diseases associated with inflammation, such as Type II Diabetes, obesity, and fatty acid metabolism disorders.

ii. Map4k4

Mitogen-activated Protein Kinase Kinase Kinase Kinase 4 (Map4k4; also known as NCK-interacting Kinase, or NIK; also referred to herein as Map4k4/NIK) is a serine/threonine kinase that regulates diverse signaling pathways, including cell migration, and is essential for mammalian development (see, e.g., Xue et al., Development, 128(9):1559-1572, 2001; Collins et al., Proc. Natl. Acad. Sci., 103(10): 3775-3780, 2006; and U.S. Patent Application Publication No. 20050239731, the entire contents of each of which are incorporated herein by reference). This kinase has been shown to specifically activate MAPK8/JNK and inhibit GLUT4. The activation of MAPK8 by Map4k4 is found to be inhibited by the dominant-negative mutants of MAP3K7/TAK1, MAP2K4/MKK4, and MAP2K7/MKK7, which suggests that this kinase may function through the MAP3K7-MAP2K4-MAP2K7 kinase cascade, and mediate the TNFα signaling pathway (see, e.g., U.S. Patent Application Publication No. 20060160133, the entire contents of which are incorporated herein by reference). Specifically, silencing of Map4k4 in macrophages, as described in more detail in the Examples, leads to blunting of secretion of TNFα and other inflammatory cytokines, indicating that macrophage function to promote inflammation is attenuated by silencing of Mapk4. It is also important to note that MAP4K4 expression is also increased by TNFα or depletion of PPARγ, which leads to the attenuation of adipogenesis. Thus, MAP4K4 functions in a signaling pathway that negatively regulates adipogenic gene expression, including GLUT4, in cultured adipocytes. Thus, inhibition of Map4k4 expression may be used to treat metabolic diseases involving inflammation, such as type II diabetes, obesity, and fatty acid metabolism disorders.

Exemplary nucleic acid and amino acid sequences for human Map4k4 are found under GenBank Nos. NM_145686 and NP_663719, respectively. The N-terminus of the human Map4k4 polypeptide has a catalytic kinase domain with 11 kinase subdomains (see, e.g., Yao et al., J. Biol. Chem., 274: 2118-2125, 1999, the entire contents of which are incorporated herein by reference). Map4k4 shares 47% and 48% amino acid sequence identity to the catalytic domain of Hematopoietic Progenitor Kinase 1 (HPK1) and Germinal Center Kinase, GCK, respectively. Other polypeptides which have been shown to interact with human Map4k4 include: Caspase 8, Docking protein 1; guanylate binding protein 3; Integrin beta 1; Nck adaptor protein 1; Solute carrier family 9, isoform A1; RasGAP; solute carrier family 9 (sodium/hydrogen exchanger), member 1; and MEKK1.

iii. RIP140

RIP140 (receptor interacting protein 140, also known as NRIP1, for Nuclear Receptor-interacting Protein 1) is a corepressor that can inhibit the transcriptional activity of a number of nuclear receptors (see, e.g., Cavailles et al., EMBO J. 14:3741-3751, 1995 and L'Horset et al., Mol. Cell. Biol. 16:6029-6036, 1996, the entire contents of each of which are incorporated herein by reference). RIP140 is essential for female fertility and plays a crucial role in lipid metabolism (see, e.g., White et al., Nat. Med, 6:1368-1374, 2000; Leonardsson et al., Proc. Natl. Acad. Sci, U.S.A. 101:8437-8442, 2004; and Christian et al., Mol. Cell. Biol., 25:9383-9391, 2005, the entire contents of each of which are incorporated herein by reference). Affymetrix GeneChip profiling has demonstrated that RIP140 depletion upregulates the expression of clusters of genes in the pathways of glucose uptake, glycolysis, TCA cycle, fatty acid oxidation, mitochondrial biogenesis, and oxidative phosphorylation in these cells (see, e.g., Powelka et al., J. Clin. Invest., 116(1): 125-136, 2006, the entire contents of which are incorporated herein by reference). RIP140-null mice, which resist weight gain on a high-fat diet, display enhanced glucose tolerance and enhanced responsiveness to insulin compared with matched wild-type mice (see, e.g., Leonardsson et al., Proc. Natl. Acad. Sci, U.S.A. 101:8437-8442, 2004, the entire contents of which are incorporated herein by reference). Thus, RIP140 suppresses genes that control energy expenditure, and inhibition of expression of a RIP140 in a cell that normally conducts glucose transport in response to stimulation by insulin (e.g., a fat cell) results in decreased inflammation (see, e.g., Christian et al., Trends Endocrinology & Metabolism, 17(6):243-250, 2006, the entire contents of which are incorporated herein by reference). Thus, inhibition of RIP140 expression may be used to treat metabolic diseases involving inflammation, such as type II diabetes, obesity, and fatty acid metabolism disorders.

RIP140 is a nuclear protein containing approximately 1158 amino acids, with a size of approximately 128 kDa. RIP140 binds to nuclear receptors via LXXLL motifs, wherein L is leucine and X is any amino acid (see, e.g., Heery et al., Nature, 387(6634):733-6, 1997, the entire contents of which are incorporated herein by reference). Ten LXXLL motifs are found in the RIP140 sequence. RIP140 also interacts with histone deacetylases and with C-terminal binding protein (CTBP) via a PXDLS motif found in the RIP140 sequence.

A human RIP140 nucleotide sequence is listed in GenBank™ under Accession No. NM_003489. The corresponding human amino acid sequence is found under Accession No. NP_003480. The nucleotide sequence of the chromosomal region containing the entire human RIP140 gene can be found in GenBank™ under Accession No. AF248484. A murine RIP140 nucleotide sequence can be found in GenBank™ under Accession No. NM_173440. The corresponding murine amino acid sequence is found under Accession No. NP_775616. RIP140 is highly conserved between vertebrate species. A number of RIP140 homologs are known in the art (see, e.g., U.S. Application Publication No. 20050261223, the entire contents of which are incorporated herein by reference).

In some embodiments, RIP140 activity can be determined by examining levels of RIP140 binding to PPARs. PPAR sequences are known in the art, for example see GenBank™ accession nos. NP_005027 (PPARα), Q03181 (PPARδ), P37231 (PPARγ).

iv. Toll-Like Receptor 4 (TLR4)

Toll-like receptors (TLRs) are generally described as pattern recognition molecules that recognize foreign constituents (polysaccharides, proteins and nucleic acid patterns) expressed by invading pathogens. As such, TLRs are the immune system's first line of innate immune defense, recognizing and responding to newly encountered microbes without a need for prior exposure (see, e.g., Kopp and Medzhitov, Curr. Opin. Immunol. 2003 15:396-401; Beutler and Rietschel, Nat. Rev. Immunol. 2003 3:169-176, the entire contents of each of which are incorporated herein by reference). Initial triggering of TLR signaling results in stimulation of inflammatory responses and induction of pathogen defense genes (see, e.g., Zhang et al., Science 303: 1522-1526, 2004, the entire contents of which are incorporated herein by reference). TLRs are also important in bridging innate and adaptive immune responses. TLR signaling stimulates the development of memory (adaptive) immune responses and molds the type of ensuing response. In addition to recognizing patterns associated with invading pathogens, TLRs also participate in "sterile inflammation," recognizing aberrant expression of endogenous molecules that could signal ongoing pathology.

Among the immediate outcomes of the TLR-dependent immune response is the production of cytokines by inflammatory cells such as macrophages. The production and release of such cytokines is responsible for the inflammatory response that accompanies bacterial infection. Toll-like receptor 4 (TLR4) activation by endotoxin or lipopolysaccharide (LPS) produced by gram-negative bacteria leads to septic shock (Cohen, J. Nature 2002 420:885-891, the entire contents of which are incorporated herein by reference). In addition, the interaction of TLR4 with the cholesterol-dependent cytolysin pneumolysin was recently reported to be critically involved in the innate immune response to gram-positive Pseudococcus (Malley et al. Proc. Natl. Acad. Sci. 2003 100 (4):1966-1971, the entire contents of which are incorporated herein by reference). In particular, these experiments demonstrate that the inflammatory response of macrophages is dependent on TLR4.

TLR4 is a type I transmembrane glycoprotein characterized by the presence of 22 leucine rich repeats (LRR) on the extracellular domain. A human TLR4 nucleotide sequence is listed in GenBank™ under Accession No. NM_138554. The corresponding human amino acid sequence is found under Accession No. NP_612564. Initiation of the signal elicited by LPS depends on the dimerization of the cytoplasmic TIR (Toll-Interleukin-1 Resistance) domain of TLR4. The activation signal is then propagated by the recruitment of a dedicated array of intracellular signaling protein adaptors followed by the activation of a complex serine/threonine kinase cascade, which eventually leads to the transcription of immunologically relevant genes.

Recently, it has been shown that nutritional fatty acids activate toll-like receptor-4 (TLR4) signaling in adipocytes and macrophages and that the capacity of fatty acids to induce inflammatory signaling in adipose cells or tissue and macrophages is blunted in the absence of TLR4 (see, e.g., Shi et al., J. Clin. Invest., 116:3015-3025, 2006, the entire contents of which are incorporated herein by reference). Furthermore, adipose tissue lipolysis, from hypertrophied adipocytes, could serve as a naturally occurring ligand for TLR4 to induce inflammation (see, e.g., Suganami et al., Biochem. Biophys. Res. Comm., 354:45-49, 2007, the entire contents of which are incorporated herein by reference). In addition, TLR4 mRNA concentration was induced during adipocyte differentiation, further enhancing free fatty acid-induced inflammation (see, e.g., Song et al., Biochem. Biophys. Res. Comm., 346:739-745, 2006, the entire contents of which are incorporated herein by reference). Therefore, inhibition of TLR4 expression may be used to treat metabolic diseases that involve inflammation, such as type II diabetes, obesity, and fatty acid metabolism disorders.

v. Secondary Knockdown Targets

Direct targeting of a particular gene (e.g., with an siRNA that targets its sequence) is not required for effective knockdown of expression of that gene. In some embodiments of the invention, siRNA is delivered to a cell to knockdown the expression of a gene whose product induces or upregulates the expression of a second gene. For example, by targeting MAP4K4 in a cell with an anti-MAP4K siRNA, expression of TNF-α can be reduced or substantially eliminated (see, for example, FIGS. 24-26). Delivery of MAP4K4 siRNA can also reduce expression of other inflammatory molecules and markes, such as IL-1β (see, for example, FIG. 28e).

B. aP2

Adipocyte fatty acid binding protein (aP2) mediates intracellular transport and metabolism of fatty acids in adipocytes as well as macrophages. A murine aP2 nucleotide sequence is listed in GenBank™ under Accession No. NM_024406. The corresponding murine amino acid sequence is found under Accession No. NP_077717. aP2 expression is regulated via the activity of PPARγ (peroxisome proliferator-activated receptor γ) and CCAAT/enhancer binding protein α(C/EBPα) (Sun et al., Journal of Lipid Research, 44:1877 (2003)). Studies of mice deficient in aP2 have indicated that it plays a role in the development of metabolic syndrome, type II diabetes and atherosclerosis and that a small molecule inhibitor of aP2 can be an effective agent to combat severe atherosclerosis and type II diabetes in mouse models (Furuhashi et al, Nature 447:959 (2007), hereby incorporated by reference in its entirety).

As shown in Example 16 below, the positive effects of aP2 downregulation can also be obtained with the delivery of GeRPs loaded with aP2-specific siRNA.

V. Modes of Delivery

The present invention comprises a payload delivery system for delivering a payload molecule to a cell. Preferred embodiments feature the delivery of nucleic acid payload agents (e.g., gene silencing agents). The delivery system of the invention uses components extracted from yeast to form yeast cell wall particles. One or more payload molecules and one or more other molecules are incorporated into the YCWP and can be delivered to cells through the interaction of the YCWP with cells.

A. Mechanisms

As noted above, extracted yeast cell wall particles are readily available, biodegradable, substantially spherical particles about 2-4 μm in diameter. Preparation of extracted yeast cell wall particles is known in the art, and is described, for example in U.S. Pat. Nos. 4,992,540, 5,082,936, 5,028,703, 5,032,401, 5,322,841, 5,401,727, 5,504,079, 5,968,811, 6,444,448 B1, 6,476,003 B1, published U.S. applications 2003/0216346 A1, 2004/0014715 A1, and PCT published application WO 02/12348 A2. A form of extracted yeast cell wall particles, referred to as "whole glucan particles," have been suggested as delivery vehicles, but have been limited either to release by simple diffusion of active ingredient from the particle or release of an agent chemically crosslinked to the whole glucan particle by biodegradation of the particle matrix. See U.S. Pat. Nos. 5,032,401 and 5,607,677.

Extracted yeast cell wall particles, primarily due to their beta-glucan content, are targeted to phagocytic cells, such as macrophages and cells of lymphoid tissue. The mucosal-associated lymphoid tissue (MALT) comprises all lymphoid cells in epithelia and in the lamina propria lying below the body's mucosal surfaces. The main sites of mucosal-associated lymphoid tissues are the gut-associated lymphoid tissues (GALT), and the bronchial-associated lymphoid tissues (BALT).

Another important component of the GI immune system is the M or microfold cell. M cells are a specific cell type in the intestinal epithelium over lymphoid follicles that endocytose a variety of protein and peptide antigens. Instead of digesting these proteins, M cells transport them into the underlying tissue, where they are taken up by local dendritic cells and macrophages.

M cells take up molecules and particles from the gut lumen by endocytosis or phagocytosis. This material is then transported through the interior of the cell in vesicles to the basal cell membrane, where it is released into the extracellular space. This process is known as transcytosis. At their basal surface, the cell membrane of M cells is extensively folded around underlying lymphocytes and antigen-presenting cells, which take up the transported material released from the M cells and process it for antigen presentation.

A study has shown that transcytosis of yeast particles (3.4+/−0.8 micron in diameter) by M cells of the Peyer's patches takes less than 1 hour (Beier, R., & Gebert, A., Kinetics of particle uptake in the domes of Peyer's patches, Am J. Physiol. 1998 July; 275 (1 Pt 1):G130-7). Without significant phagocytosis by intraepithelial macrophages, the yeast particles migrate down to and across the basal lamina within 2.5-4 hours, where they quickly get phagocytosed and transported out of the Peyer's patch domes. M cells found in human nasopharyngeal lymphoid tissue (tonsils and adenoids) have been shown to be involved in the sampling of viruses that cause respiratory infections. Studies of an in vitro M cells model have shown uptake of fluorescently labeled microspheres (Fluospheres, 0.2. mu.m) and chitosan microparticles (0.2. mu.m) van der Lubben I. M., et al., Transport of chitosan microparticles for mucosal vaccine delivery in a human intestinal M-cell model, J Drug Target, 2002 September; 10 (6):449-56. A lectin, *Ulex europaeus* agglutinin 1 (UEA1, specific for alpha-L-fucose residues) has been used to target either polystyrene microspheres (0.5. mu.m) or polymerized liposomes to M cells (0.2. mu.m) (Clark, M. A., et al., Targeting polymerised liposome vaccine carriers to intestinal M cells, Vaccine. 2001 Oct. 12; 20 (1-2):208-17). In vivo studies in mice have reported that poly-D,L-lactic acid (PDLLA) microspheres or gelatin microspheres (GM) can be efficiently taken up by macrophages and M cells. (Nakase, H., et al., Biodegradable microspheres targeting mucosal immune-regulating cells: new approach for treatment of inflammatory bowel disease, J. Gastroenterol. 2003 March; 38 Suppl 15:59-62).

However, it has been reported that uptake of synthetic particulate delivery vehicles including poly(DL-lactide-co-glycolide) microparticles and liposomes is highly variable, and is determined by the physical properties of both particles and M cells. Clark, M. A., et al., Exploiting M cells for drug and vaccine delivery, Adv Drug Deliv Rev. 2001 Aug. 23; 50 (1-2):81-106. The same study reported that delivery may be enhanced by coating the particles or liposomes with reagents including appropriate lectins, microbial adhesins and immunoglobulins which selectively bind to M cell surfaces. See also, Florence, A. T., The oral absorption of micro- and nano-particulates: neither exceptional nor unusual, Pharm Res. 1997 March; 14 (3):259-66.

Pathogen pattern recognition receptors (PRRs) recognize common structural and molecular motifs present on microbial surfaces and contribute to induction of innate immune responses. Mannose receptors and beta-glucan receptors in part participate in the recognition of fungal pathogens. The mannose receptor (MR), a carbohydrate-binding receptor expressed on subsets of macrophages, is considered one such PRR. Macrophages have receptors for both mannose and mannose-6-phosphate that can bind to and internalize molecules displaying these sugars. The molecules are internalized by endocytosis into a pre-lysosomal endosome. This internalization has been used to enhance entry of oligonucleotides into macrophages using bovine serum albumin modified with mannose-6-phosphate and linked to an oligodeoxynucleotide by a disulfide bridge to a modified 3' end; see Bonfils, E., et al., Nucl. Acids Res. 1992 20, 4621-4629. see E. Bonfils, C. Mendes, A. C. Roche, M. Monsigny and P. Midoux, Bioconj. Chem., 3, 277-284 (1992). Macrophages also express beta-glucan receptors, including CR3 (Ross, G. D., J. A. Cain, B. L. Myones, S. L. Newman, and P. J. Lachmann. 1987. Specificity of membrane complement receptor type three (CR3) for β-glucans. Complement Inflamm. 4:61), dectin-1. (Brown, G. D. and S. Gordon. 2001. Immune recognition. A new receptor for β-glucans. Nature 413:36), and lactosylceramide (Zimmerman J W, Lindermuth J, Fish P A, Palace G P, Stevenson T T, DeMong D E. A novel carbohydrate-glycosphingolipid interaction between a beta-(1-3)-glucan immunomodulator, PGG-glucan, and lactosylceramide of human leukocytes. J. Biol. Chem. 1998 Aug. 21:273 (34):22014-20). The beta-glucan receptor, CR3 is predominantly expressed on monocytes, neutrophils and NK cells, whereas dectin-1 is predominantly expressed on the surface of cells of the macrophages. Lactosylceramide is found at high levels in M cells. Microglia can also express a beta-glucan receptor (Muller, C. D., et al. Functional beta-glucan receptor expression by a microglial cell line, Res Immunol. 1994 May; 145 (4):267-75).

There is evidence for additive effects on phagocytosis of binding to both mannose and beta-glucan receptors. Giaimis et al. reported observations suggesting that phagocytosis of unopsonized heat-killed yeast (*S. cerevisiae*) by murine macrophage-like cell lines as well as murine peritoneal resident macrophages is mediated by both mannose and beta-glucan receptors. To achieve maximal phagocytosis of unopsonized heat-killed yeast, coexpression of both mannose and beta-glucan receptors is required (Giaimis, J., et al., Both mannose and beta-glucan receptors are involved in phagocytosis of unopsonized, heat-killed *Saccharomyces cerevisiae* by murine macrophages, J Leukoc Biol. 1993 December; 54 (6):564-71).

As noted above, the nanoparticles of the invention may be designed to modulate the kinetics of payload molecule effects. The LbL construction of a nanoparticle can effectively be reversed upon contact or entry of the YCWP with a cell or organism. By designing the nanoparticle of the invention to contain particular a particular payload molecule within a particular layer or section of the nanoparticle, the timing and rate of release of the payload molecule can be adjusted.

As a particular species of payload molecule is release into a cell or organism, the effect of that payload molecule on the cell or organism will begin. Through design of a nanoparticle of the invention, the onset of effects on a cell or on an organism created by the introduction of a payload molecule to a cell or organism can be modulated for speed of onset and/or duration of the effect. In some embodiments, a payload molecule is released sooner and/or faster in order to treat an acute condition. In some embodiments, a payload molecule is released later or more slowly in order to treat a chronic condition. In some embodiments, two or more payload molecules are delivered by nanoparticles, either contained within the same nanoparticle or contained within a set of two or more nanoparticle. The kinetics of release may be the same or different for any two payload molecules released. The kinetics of release may be different for a payload molecule contained in two or more layers or sections of one or more nanoparticles.

Embodiments of the invention feature treatments comprising the delivery of a payload molecule to a cell or organism from more than one layer or section of one or more nanoparticles, such that some payload molecules are delivered at a faster rate and/or sooner in time than other payload molecules. Some embodiments feature one or more nanoparticles that comprise two or more payload molecules, in similar or different layers or sections of the one or more nanoparticles. In some embodiments, nanoparticles are designed to release payload molecules of one or more species sequentially, with some or no overlap between the release periods. Some embodiments feature treatments that require or are improved by the sequential release of payload molecules to a cell or organism.

In preferred embodiments of the invention, two or more siRNAs are released from YCWP-encapsulated nanoparticles at different rates and/or speeds, so that gene silencing effects created by the siRNAs also occur at different rates and/or speeds. Some embodiments feature two or more siRNAs co-localized within particles, enabling the release of the siRNAs to occur at the same or essentially similar rates and speeds. In some preferred embodiments, the siRNAs released serve to silence the expression of genes found in signaling pathways important for creating or augmenting inflammation.

B. Formulations

Embodiments of the invention feature YCWP that encapsulate nanoparticles (e.g., GeRPs). The nanoparticles may have a uniform consistency. Some nanoparticles may contain layers or sections that contain distinct formulations or ingredients. Different YCWP within a single allotment or dosage may contain nanoparticles with different ingredients, structures or formulas.

In preferred embodiments, the particulate delivery system of the present invention including the desired payload molecule is useful for the manufacture of a pharmaceutical product for the treatment of genetic disorder or the genetic component of a condition. Preferred embodiments feature nucleic acid payload agents as the desired payload molecules for delivery. Such pharmaceutical products are suitably administered orally, rectally, parenterally, (for example, intravenously, intramuscularly, or subcutaneously) intracistemally, intravaginally, intraperitoneally, intravesically, locally (for example, powders, ointments or drops), or as a buccal or nasal spray. The pharmaceutical products are preferably administered orally, buccally, and parenterally, more preferably orally. Particles loaded with different payloads, e.g. a polynucleotide, a polynucleotide expression vector or a small molecule therapeutic can be mixed in the appropriate proportions and administered together, e.g., in a capsule, for combination therapy.

The encapsulated particulate delivery system of the present invention is administered to a patient in a therapeutically effective amount. The encapsulated particulate delivery system can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using a controlled release formulation. It is also noted that the dose of the compound can be varied over time. The particulate delivery system can be administered using an immediate release formulation, a controlled release formulation, or combinations thereof. The term "controlled release" includes sustained release, delayed release, and combinations thereof.

Oral formulations suitable for use in the practice of the present invention include capsules, gels, cachets, tablets, effervescent or non-effervescent powders or tablets, powders or granules; as a solution or suspension in aqueous or non-aqueous liquid; or as an oil-in-water liquid emulsion or a water-in-oil emulsion. The compounds of the present invention may also be presented as a bolus, electuary, or paste.

Generally, formulations are prepared by uniformly mixing the active ingredient with liquid carriers or finely divided solid carriers or both, and then if necessary shaping the product. A pharmaceutical carrier is selected on the basis of the chosen route of administration and standard pharmaceutical practice. Each carrier must be "acceptable" in the sense of being compatible with the other ingredients of the formulation and not injurious to the subject. This carrier can be a solid or liquid and the type is generally chosen based on the type of administration being used. Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g., PEG, are also preferred carriers.

The formulations for oral administration may comprise a non-toxic, pharmaceutically acceptable, inert carrier such as lactose, starch, sucrose, glucose, methyl cellulose, magnesium stearate, dicalcium phosphate, calcium sulfate, mannitol, sorbitol, cyclodextrin, cyclodextrin derivatives, or the like.

Capsule or tablets can be easily formulated and can be made easy to swallow or chew. Tablets may contain suitable carriers, binders, lubricants, diluents, disintegrating agents, coloring agents, flavoring agents, flow-inducing agents, or melting agents. A tablet may be made by compression or molding, optionally with one or more additional ingredients. Compressed tables may be prepared by compressing the active ingredient in a free flowing form (e.g., powder, granules) optionally mixed with a binder (e.g., gelatin, hydroxypropylmethylcellulose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, or the like. Lubricants used in these dosage forms include sodium oleate, sodium stearate, magnesium stearate, sodium benzoate, sodium acetate, sodium chloride, or the like. Disintegrators include, for example, starch, methyl cellulose, agar, bentonite, xanthan gum, or the like. Molded tablets may be made by molding in a suitable machine a mixture of the powdered active ingredient moistened with an inert liquid diluent.

The tablets may optionally be coated or scored and may be formulated so as to provide slow- or controlled-release of the active ingredient. Tablets may also optionally be provided with an enteric coating to provide release in parts of the gut other than the stomach.

Exemplary pharmaceutically acceptable carriers and excipients that may be used to formulate oral dosage forms of the present invention are described in U.S. Pat. No. 3,903,297 to Robert, issued Sep. 2, 1975, incorporated by reference herein in its entirety. Techniques and compositions for making dosage forms useful in the present invention are described in the following references: 7 Modem Pharmaceutics, Chapters 9 and 10 (Banker & Rhodes, Editors, 1979); Lieberman et al., Pharmaceutical Dosage Forms: Tablets (1981); and Ansel, Introduction to Pharmaceutical Dosage Forms 2nd Edition (1976).

Formulations suitable for parenteral administration include aqueous and non-aqueous formulations isotonic with the blood of the intended recipient; and aqueous and non-aqueous sterile suspensions which may include suspending systems designed to target the compound to blood components or one or more organs. The formulations may be presented in unit-dose or multi-dose sealed containers, for example, ampoules or vials. Extemporaneous injections solutions and suspensions may be prepared from sterile powders, granules and tablets of the kind previously described. Parenteral and intravenous forms may also include minerals and other materials to make them compatible with the type of injection or delivery system chosen.

VI. Methods of Treatment

YCWPs with molecular payloads (e.g., GeRPs) provide a powerful and novel method for delivery of sensitive molecules subject to in vivo degradation to cells and tissues, as well as specific targeting of macrophages and delivery of payloads to numerous tissues and cells throughout an organism. Following transcytosis of YCWPs into the GALT, YCWPs undergo phagocytosis by macrophages, which subsequently travel to other tissues and organs.

A. Metabolic Diseases and Disorders

Methods of treating metabolic diseases and disorders (e.g., disorders related to glucose metabolism) are provided herein. "Treating" includes methods that cure, alleviate, relieve, alter, ameliorate, palliate, improve or affect the disorder, the symptoms of the disorder or the predisposition toward the disorder. The methods can be used in vivo or on cells in culture, e.g., in vitro or ex vivo. For in vivo embodiments, the method is effected in a subject and includes administering the agent to the subject under conditions effective to permit the agent to modulate the expression or activity of the target gene or polypeptide in a cell.

Embodiments of the invention include methods of preparing and administering to a subject an agent for modulating (e.g., downregulating) the expression of a target gene or protein in vivo. Preferred embodiments feature a nanoparticle-encapsulating YCWP, including YCWP with encapsulated nanoparticles comprising nucleic acids. In some embodiments, the nucleic acids are siRNAs (e.g., GeRPs). In preferred embodiments, the siRNAs are directed against the activity of genes in an inflammatory pathway, including Map4k4. In some embodiments, the YCWP agent with encapsulated nanoparticles is delivered orally. In some embodiments, the YCWP agent is delivered by injection.

Agents that modulate expression or activity of a target gene or polypeptide in vitro can be further tested in vivo in animal models. For example, a compound identified as a modulator of a the target gene or polypeptide is tested in an animal such as an animal model for obesity or diabetes (e.g., type II diabetes, e.g., ob/ob mice obtained from Jackson Laboratories (Strain Name: B6.V-Lep.sup.ob/J), db/db mice; see, e.g., Sima A A F, Shafrir E. Animal Models in Diabetes: A Primer. Taylor and Francis, Publ Amsterdam, Netherlands, 2000). At various time points after administration of the test agent, levels of expression or activity of the target gene or polypeptide. Levels of inflammatory signaling (e.g., inflammatory markers or mediators) and/or levels of glucose, glucose tolerance, and plasma insulin are monitored to determine whether the test compound has a beneficial effect on the metabolic disease or disorder, relative to control, i.e., whether the test compound causes an increase in insulin sensitivity, a decrease in insulin resistance, a reduction in hyperglycemia or plasma insulin levels. Other measurements of gene activity and of whole organism status can be made. Examples 6 through 14 below feature testing of YCWP agents encapsulating siRNAs given to mice either orally or by intraperitoneal injection.

Data obtained from the cell culture assays and animal studies can be used in formulating an appropriate dosage of any given agent for use in humans. A therapeutically effective amount of an agent will be an amount that delays progression of or improves one or more symptoms of the condition, whether evident by improvement in an objective sign (e.g., increased insulin sensitivity, decreased blood glucose levels, for example, fasting blood glucose levels) or subjective symptom of the disease. Certain factors may influence the dosage and timing required to effectively treat a subject (e.g., the severity of the disease or disorder, previous treatments, the general health and/or age of the subject, and other diseases present). YCWP encapsulating nanoparticles may be designed as described above to improve the kinetics of delivery of a payload molecule in order.

Compositions useful for modulating expression or activity of target genes or proteins in vivo can be incorporated into pharmaceutical compositions and administered to subjects who have, or who are at risk of developing, a disorder or condition related to the activity of the genes or proteins, such as those involved in glucose metabolism (e.g., related to disregulated glucose metabolism such as type I diabetes, type II diabetes, or obesity). Such compositions will include one or more agents that modulate the expression or activity of the genes or proteins and a pharmaceutically acceptable carrier (e.g., a solvent, dispersion medium, coating, buffer, absorption delaying agent, and the like, that are substantially non-toxic). Supplementary active compounds can also be incorporated into the compositions. In preferred embodiments, compositions useful for modulating expression or activity of genes or proteins in vivo comprise nucleic acid payload agents (e.g., silencing agents for knocking down gene expression), as described supra.

Pharmaceutical compositions are formulated to be compatible with their intended route of administration, whether oral or parenteral (e.g., intravenous, intradermal, subcutaneous, transmucosal (e.g., nasal sprays are formulated for inhalation), or transdermal (e.g., topical ointments, salves, gels, patches or creams as generally known in the art). The compositions can include a sterile diluent (e.g., sterile water or saline), a fixed oil, polyethylene glycol, glycerine, propylene glycol or other synthetic solvents; antibacterial or antifungal agents such as benzyl alcohol or methyl parabens, chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates; and isotonic agents such as sugars (e.g., dextrose), polyalcohols (e.g., manitol or sorbitol), or salts (e.g., sodium chloride). Liposomal suspensions (including liposomes targeted to affected cells with monoclonal antibodies specific for neuronal antigens) can also be used as pharmaceutically acceptable carriers (see, e.g., U.S. Pat. No. 4,522,811). Preparations of the compositions can be formulated and enclosed in ampules, disposable syringes or multiple dose vials. Where required (as in, for example, injectable formulations), proper fluidity can be maintained by, for example, the use of a coating such as lecithin, or a surfactant. Absorption of the active ingredient can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Where oral administration is intended, the agent can be included in pills, capsules, troches and the like and can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Compositions containing the agents that modulate gene expression of targeted proteins and peptides in vivo, such as glucose transport-related polypeptides, can be formulated for oral or parenteral administration in dosage unit form (i.e., physically discrete units containing a predetermined quantity of active compound for ease of administration and uniformity of dosage). Toxicity and therapeutic efficacy of compounds can be determined by standard pharmaceutical procedures in cell cultures or experimental animals. One can, for example, determine the $LD_{50}$ (the dose lethal to 50% of the population) and the $ED_{50}$ (the dose therapeutically effective in 50% of the population), the therapeutic index being the ratio of $LD_{50}$:$ED_{50}$. Agents that exhibit high therapeutic indices are preferred. Where an agent exhibits an undesirable side effect, care should be taken to target that agent to the site of the affected tissue (the aim being to minimize potential damage to unaffected cells and, thereby, reduce side effects). Toxicity and therapeutic efficacy can be determined by other standard pharmaceutical procedures.

Data obtained from the cell culture assays and animal studies can be used in formulating an appropriate dosage of any given agent for use in humans. A therapeutically effective amount of an agent will be an amount that delays progression of or improves one or more symptoms of the condition, whether evident by improvement in an objective sign (e.g., blood glucose levels) or subjective symptom of the disease. Certain factors may influence the dosage and timing required to effectively treat a subject (e.g., the severity of the disease or disorder, previous treatments, the general health and/or age of the subject, and other diseases present).

As noted above, payload molecules administered according to the methods described here can be small molecules, polypeptides, polynucleotides (or analogs thereof), or organic or inorganic compounds. Typically, such molecules will have a molecular weight less than about 10,000 grams per mole (e.g., less than about 7,500, 5,000, 2,500, 1,000, or 500 grams per mole). Salts, esters, and other pharmaceutically acceptable forms of any of these compounds can be assayed and, if a desirable activity is detected, administered according to the therapeutic methods described herein. Exemplary doses include milligram or microgram amounts of the small molecule per kilogram of subject or sample weight (e.g., about 1 μg-500 mg/kg; about 100 μg-500 mg/kg; about 100 μg-50 mg/kg; 10 μg-5 mg/kg; 10 μg-0.5 mg/kg; or 1 μg-50 μg/kg). While these doses cover a broad range, one of ordinary skill in the art will understand that therapeutic agents, including small molecules, vary in their potency, and effective amounts can be determined by methods known in the art. Typically, relatively low doses are administered at first, and the attending physician or veterinarian (in the case of therapeutic application) or a researcher (when still working at the clinical development stage) can subsequently and gradually increase the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

The invention will be further described in the following examples which do not limit the scope of the invention described in the claims.

The foregoing disclosure teaches to those of skill in the art the aspects of the invention including how to make and use the invention. The following examples are meant to provide further elucidation of the invention but are not meant as limitations thereof.

EXAMPLES

Non-viral gene delivery technologies have been developed using layer by layer self-assembly of nanomaterials held together by electrostatic interactions in order to provide nanoparticulate materials that protect and deliver DNA to cells. Here we report a new payload agent delivery technology based on the in situ layer by layer synthesis of nanoparticles caged within hollow yeast cell wall particles (YCWP). YCWP provide protection and facilitate oral and systemic receptor-targeted delivery of payload molecules to phagocytic cells.

In particular embodiments, yeast cell wall particles have been shown to be an effective material to encapsulate DNA following layer-by-layer assembly of polymers by electrostatic interactions caged inside hollow YCWP. Labeling of each layer with rhodamine allowed quantitative fluorescence analysis and optimization of LbL nanoplex formation within YCWP. The YCWP DNA delivery system efficiently delivered the plasmid, gWizGFP, and transfected NIH3T3-D1 cells.

YCWP are porous hollow 2-4 micron microspheres prepared from Baker's yeast composed primarily of beta 1,3-D-glucan, mannoproteins and chitin. Nanoparticulate cores composed of anionic and cationic polymers were constructed from tRNA and PEI within YCP as described above (FIG. 1a). These YCWP encapsulated cationic nanoparticulate cores were used to absorb DNA onto the nanoparticulate surface and then coated with PEI to generate the YCWP DNA transfection formulations (FIG. 1b).

Rhodamine labeled tRNA, DNA or PEI were used for optimization of the formation of each layer of the encapsulated nanoparticles. A calibration curve for each labeled compound was used to quantitate binding.

The nanoparticles inside YCWP consist of a core of tRNA/polyethylenimine (PEI) followed by a DNA layer that is finally coated with a protective layer of PEI. Using rhodamine labeling of tRNA, PEI and DNA, the layer-bylayer formation of the nanoparticles was visualized by fluorescent microscopy and quantitated by fluorescence spectroscopy and flow cytometry. Optimal conditions (tRNA/YCWP, PEI/YCWP ratios and DNA loads) to synthesize YCWP encapsulated nanoparticles were determined from these results. The efficiency of this DNA encapsulation technology to deliver DNA and transfect cells was evaluated by the expression of green fluorescent protein (GFP) encoded by the plasmid gWizGFP delivered by YCWP tRNA/PEI/gWizGFP/PEI formulations to 3T3-D1 cells.

Materials and Methods

Ribonucleic acid from Torula yeast, Type VI, (tRNA); high molecular weight water-free polyethylenimine (PEI, 25 kDa); deoxyribonucleic acid sodium salt from Salmon testes (DNA); and rhodamine β isothiocyanate were purchased from Sigma Aldrich (Allentown, Pa.) and used as received. 5-([4,6-dichlorotriazin-2-yl]-amino)fluorescein monohydrochloride (DTAF) was purchased from Research Organics Inc.

(Cleveland, Ohio). Solvents and buffers solutions were purchased from Sigma Aldrich or VWR and used without further purification.

Rhodamine and Fluorescein Labeling of Nucleic Acids

DNA or tRNA (10 mg) was dissolved in 10 mLs of 5 mM EDTA. The material was sonicated until viscosity was lost and 1.2 mL of 0.1 M carbonate buffer (pH 9.2) was added. DTAF or rhodamine at a concentration of 1 mg/mL in DMSO was added to the buffered DNA solution (10% v/v) and the solution was stirred at room temperature in the dark overnight. Tris buffer (2 mLs 1M, pH 8.3) was added and the reaction mixture was stirred for additional 15 minutes at room temperature to quench free fluorescent labeling reagent. Sodium chloride (1 mL of 1 M aqueous NaCl) and ethanol (30 mLs) were added to the solution and incubated at $-20°$ C. until a colored precipitate appeared. The precipitate was collected by centrifugation, and washed with 70% ethanol until the supernatant was clear. The solid was completely dried and dissolved in water at a 10 mg/mL concentration and stored at 4° C. in the dark. The amount of fluorescent probe bound to each nucleic acid was determined spectrophotometrically by adsorption at 495 nm (DTAF) or 540 nm (rhodamine). The labeled DNA contains ~2.3±0.3% (w/w) of rhodamine, and 5.9±1.7% (w/w) of DTAF. tRNA was labeled with ~0.15±0.05% (w/w) of rhodamine and 0.6±0.1% (w/w) of DTAF.

Rhodamine and Fluorescein Labeling of PEI

PEI was labeled following a similar procedure used for labeling of DNA and tRNA, with the following changes: PEI was dissolved in 5 mM EDTA at a concentration of 3 mg/mL. Rhodamine and DTAF were used at a concentration of 1 mg/mL in DMSO. After incubation with Tris buffer, 1M NaCl was added (1 mL for each 10 mLs of initial PEI solution). The product was purified by dialysis against water and lyophilized. Spectrophotometric characterization of the labeled PEI showed that the final product contains ~3.1±0.3% (w/w) of rhodamine and 5.7±0.1% (w/w) of DTAF. Preparation of Yeast Cell Wall Particles (YCWP) (24) Yeast glucan particles (YGP): Sacharomyces cerevisiae (100 g Fleishmans Bakers yeast, AB Mauri™ Food Inc., Chesterfield, Mo.) was suspended in 1 liter 1M NaOH heated to 80° C. for 1 hour. The insoluble material containing the yeast cell walls was collected by centrifugation at 2000×g for 10 minutes. This insoluble material was then suspended in 1 liter of water and brought to pH 4-5 with HCl, and incubated at 55° C. for 1 hour. The insoluble reside was again collected by centrifugation and washed once with 1 L water, four times with 200 ml isopropanol and twice with 200 mL acetone. The resulting slurry was placed in a glass tray and dried at room temperature to produce 12.4 g of a fine, slightly off-white powder. Yeast glucan mannan particles (YGMP): S. cerevisiae cell walls (75 g SAF-Mannan, SAF Agri, Milwaukee, Wis.) were suspended in 1 liter water and adjusted to pH 12-12.5 with 1 M NaOH and heated to 60° C. for 1 hour. The insoluble material containing the cell walls was recovered by centrifuging at 2000×g for 10 minutes. This material was then suspended in 1 liter of water and brought to pH 4-5 with HCl, and incubated at 55° C. for 1 hour. The insoluble reside was recovered by centrifugation and washed once with 1 L water, four times with 200 ml dehydrated isopropanol and twice with 200 mL acetone. The resulting slurry was placed in a glass tray and dried at room temperature to produce 15.6 g of a fine, slightly off-white powder.

Preparation of YCWP Cationized Cores

Dry yeast glucan particles or yeast glucan mannan particles were mixed with a volume of the anionic core polymer tRNA (10 mg/ml in 50 mM Tris HCl pH 8, 2 mM EDTA and 0.15M NaCl (TEN)) to minimally hydrate the YCWP and incubated for 2 hours to allow the YCWP to swell and adsorb tRNA solution. Neutral PEI (2 mg/ml in TEN) was added in excess to form YCWP encapsulated polyplexes, and the YCWP were resuspended by homogenization or sonication. PEI adsorption and nanocomplex formation was allowed to proceed for at least one hour. The suspension was centrifuged and particles were resuspended in 70% ethanol to sterilize the particles, and then washed three times in 0.9% saline, resuspended, counted and diluted to $1\times10^8$ particles/mL in 0.9% saline and stored at $-20°$ C.

Preparation of YCWP Cores with DNA-PEI Coated Nanocomplexes

The binding of a DNA layer to the cationized nanoplexed cores inside the YCWP was accomplished by preparing a suspension of YCWP-tRNA-PEI cores ($1\times10^8$ particles/mL), DNA and saline solution (total volume=75 µL). The suspension was incubated for 2 hours to allow for DNA binding to the cationic nanoparticle surface, and neutral PEI (25 µl 0.01% w/v) in 0.9% saline added to coat the bound DNA.

Fluorescence Assays

Fluorescence characterizations were carried out for each layer of the nanoplex delivery system by preparing YCWP samples containing one fluorescently labeled layer. The samples were prepared over a range of tRNA/YCWP and PEI/YCWP ratios, and DNA concentrations to determine the optimal concentration for each layer. Fluorescence measurements were obtained with a Spectra Max Gemini XS plate reader (Molecular Devices, Union City, Calif.) using the SoftMax Pro v 5.0.1 software. Rhodamine fluorescence measurements were obtained at 573 nm after excitation at 540 nm, and the final fluorescence result was the average of nine measurements. The samples were mixed for five seconds before measurement. To avoid error introduced by light scattering produced by the particles, control measurements were obtained with a sample containing the same amount of particles/mL without any fluorescent compound. The final fluorescence results were corrected by subtracting the response for the control samples from the YCWP encapsulated fluorescent nanoplex samples. The amount of any particular fluorescent compound bound contained within the YCWP was determined from the fluorescence response using calibration curves obtained by measuring the fluorescence of each rhodamine labeled material in solution over a linear range response.

Fluorescence Microscopy

An Arcturus fluorescence microscope was used to acquire fluorescent photomicrographs, and to score transfection results for Green Fluorescent Protein (GFP).

Flow Cytometry (FACS)

FACS measurements were obtained with a Becton Dickinson FACSCalibur instrument (BD, Franklin Lakes, N.J.). Samples were prepared for FACS analysis at a concentration of $2\times10^6$ particles/mL in PBS. Unmodified YGP and YGMP particles were used as negative controls, and YCWP particles with the yeast cell wall chemically modified with rhodamine were used as the positive control. The particles were analyzed with an FL2 laser (570-610 nm) by collecting 20000 measurements. Gating and analysis was performed using FlowJo 6.4.2 software.

Transfection Experiments

YCWP-tRNA/PEI (10 µL, $1\times10^8$ particles/mL) suspensions were mixed with the indicated amount of gWizGFP plasmid DNA (Genlantis, San Diego, Calif.) over a concentration range of 0.01 to 0.1 µg/µL, and 0.9% saline solution was added to bring the total volume to 75 µL. DNA was bound to the YCWP/tRNA/PEI cationic nanoparticle surface for 2 hours at room temperature. Then, 25 μL of 0.01% neutral PEI in 0.9% saline was added to coat the DNA surface for 20 minutes. Dulbecco's Modified Eagles Medium (DMEM medium with 10% fetal calf serum, 1% penicillin-streptomycin and 1% glutamine) was added and the final mixture was transferred to 24-well plates containing $5\times10^5$ cells/well of the murine fibroblast cell line NIH3T3-D1. The plates were incubated at 37° C. under 5% $CO_2$ overnight, the medium was changed and the plates were incubated for an additional 16-24 hours. After 40-48 hours, the medium was removed, cells washed once with phosphate buffer saline (PBS), fixed with 250 μL of 0.5% formalin in PBS, and scored for GFP expression by manual counting of the proportion of fluorescent cells with a fluorescence microscope.

Preparation of Hollow β1,3-D-Glucan Shells and siRNA Encapsulation

The siRNA was incorporated into the interior of hollow glucan shells to make glucan encapsulated siRNA Particles (GeRP) by a layer by layer synthesis strategy. All siRNA was custom ordered from Dharmacon (Lafayette, Colo.). Ribonucleotide acid from Torula yeast, Type VI, (tRNA), high molecular weight water-free polyethylenimine (PEI, 25 kDa), collagenase, D-galactosamine, *Escherichia coli* lipoplysaccharide (LPS), bovine serum albumin (BSA) and thioglycollate broth were purchased from Sigma Aldrich (Allentown, Pa.) and used as received. 5-([4,6-dichlorotriazin-2-yl]-amino) fluorescein monohydrochloride (DTAF) was purchased from Invitrogen (Eugene, Oreg.). Solvents and buffer solutions were purchased from Signma Aldrich or VWR (West Chester, Pa.) and used without further purification.

Hollow glucan shells were prepared from *Saccharomyces cerevisiae* as follows. *S. cerevisiae* (100 g Fleishmans Bakers yeast, AB Mauri™ Food Inc., Chesterfield, Mo.) was suspended in 1 liter 1M NaOH and heated to 80° C. for 1 h. The insoluble material containing the yeast cell walls was collected by centrifugation at 2000×g for 10 minutes. This insoluble material was then suspended in 1 liter of water and brought to pH 4-5 with HCl, and incubated at 55° C. for 1 h. The insoluble residue was again collected by centrifugation and washed once with 1 liter of water, four times with 200 ml isopropanol and twice with 200 ml acetone. The resulting slurry was placed in a glass tray and dried at room temperature to produce 12.4 g of a fine, slightly off-white powder.

Glucan particles were labeled with fluorescein as follows. Glucan shells (1 g) were suspended in 100 ml 0.1M carbonate buffer (pH 9.2), collected by centrifugation at 2000×g for 10 minutes and resuspended in 100 ml 0.1M carbonate buffer (pH 9.2). 5-(4,6-Dichlorotriazinyl) aminofluorescein at a concentration of 1 mg/ml in DMSO was added to the buffered glucan shell suspension (10% v/v) and the reaction was mixed at room temperature in the dark overnight. Tris buffer (2 ml 1M, pH 8.3) was added and the reaction mixture was stirred for additional 15 minutes at room temperature to quench free fluorescent labeling reagent. The fluorescently labeled glucan shells were collected by centrifugation at 2000×g for 10 minutes and washed with sterile pyrogen-free water until the color was removed. The glucan shells were then dehydrated by four washes with absolute ethanol, two washes with acetone and dried in the dark at room temperature. The resulting powder was ground to a fine bright yellow powder to produce ~1 g of FL-glucan shells.

Next, RNA was absorbed into dry hollow glucan shells and encapsulated cationic nanocomplexes formed by cationic polymer trapping, as follows. Dry glucan shell or FL-glucan shell were mixed with a volume of the anionic core polymer tRNA (10 mg/ml in 50 mM Tris HCl pH 8, 2 mM EDTA and 0.15M NaCl (TEN)) to minimally hydrate the glucan shell and incubated for 2 h to allow the glucan shell to swell and adsorb tRNA solution. Neutral PEI (2 mg/ml in TEN) was added in excess to form glucan encapsulated nanoplexed particles, and the encapsulated nanoplexes were resuspended by homogenization or sonication. PEI adsorption and nanocomplex formation was allowed to proceed for at least 1 h. The suspension was centrifuged and particles were resuspended in 70% ethanol, and then washed three times in 0.9% saline, resuspended, counted and diluted to $1\times10^8$ particles/ml in 0.9% saline and stored at −20° C.

Negatively charged fluorescently labeled siRNA was absorbed onto the positively charged nanocomplex surface and finally coated with a cationic polymer layer to produce multi-layered GeRP formulations, as follows. The binding of an siRNA layer to the cationized nanoplexed core surfaces inside the glucan shell or FL-glucan shell was accomplished by preparing a suspension of glucan encapsulated nanoplexed particles, ($1\times10^8$ particles/ml), siRNA and saline solution (total volume=75 μl). The suspension was incubated for 2 hours to allow for siRNA binding to the cationic nanoparticle surfaces, and neutral PEI (25 μl 0.01% w/v) in 0.9% saline was added to trap and coat the bound siRNA. For animal experiments the siRNA formulation process was carried out at 20-fold higher concentration of all components, and following the addition of the final layer of PEI the GeRP formulations were collected by centrifugation at 2000×g for 10 minutes and resuspended in sterile pyrogen-free saline to deliver 100 μg of formulation in 200 μl. The concentrated GeRP formulations were briefly sonicated to break up any aggregates and frozen until use.

Exemplary formulations are as follows:

| Formulation for 10 + 6 cells in 1 well of a 6-well plate | | | | |
|---|---|---|---|---|
| component | Saline | Endoporter | YGP-F tR/P | |
| concentration volume (ul) | 0.09% 57.5 | 0.05X 20 | $1 \times 10 + 9$/ml 10.0 | vortex and incubate for 1 hr |
| siRNA | | | PEI | |
| 20 ng = 3.2 pmoles/ul 12.5 | add siRNA while vortexing and incubate for 2 hr | 0.01% = 100 ug/ml 50.0 | add PEI while vortexing and incubate for 20 min | |

Add 600 ul of Media (DMEM+10% FBS+Antibiotics for PECs) and treat cells with 600 ul of the final mix.

| formulation for 1 dose for in vivo gavage | | | | |
|---|---|---|---|---|
| component | Saline | Endoporter | YGP-F tR/P | |
| concentration volume (ul) | 0.09% 339.6 | 0.1X 10 | $1 \times 10 + 9$/ml 100.0 | vortex and incubate for 1 hr |
| siRNA | | | PEI | |
| 0.625 ug = 100 pmoles/ul 0.4 | add siRNA while vortexing and incubate for 2 hr | 0.1% = 1 mg/ml 50.0 | add PEI while vortexing and incubate for 20 min | |

Centrifuge at 2000 rpm 10 min, resuspend the pellet in 200 ul of saline and sonicate.

| formulation for 1 dose for in vivo i.p. | | | | |
|---|---|---|---|---|
| component | Saline | Endoporter | YGP-F tR/P | |
| concentration | 0.09% | 0.1X | 1 × 10 + 9/ml | vortex and incubate for 1 hr |
| volume (ul) | 389.6 | 10 | 50.0 | |
| siRNA | | PEI | | |
| 0.625 ug = 100 pmoles/ul 0.4 | add siRNA while vortexing and incubate for 2 hr | 0.1% = 1 mg/ml 50.0 | add PEI while vortexing and incubate for 20 min | |

Centrifuge at 2000 rpm 10 min, resuspend the pellet in 200 ul of saline and sonicate.

Cell Culture and GeRP Treatment 10 week-old C57BL6/J male were i.p. injected with 1 ml 4% thioglycollate broth. After 1-3 days, peritoneal exudates cells (PECs) (106) were isolated and incubated for 48 h with GeRPs and FL-GeRPs at a 10:1 particle-to-cell ratio, as previously determined (Hong et al., *J Immunol* 173, 797-806 (2004), hereby incorporated by reference). For microscopic analysis, cells were stained with the macrophage specific antibody, F4/80 coupled to an AlexaFluor405 probe from AbD-Serotec (Raleigh, N.C.).

Isolation of RNA and Real Time PCR

RNA isolation was performed according to the Trizol Reagent Protocol from (Invitrogen, Carlsbad Calif.). The cDNA was synthesized from 1 μg of total RNA using iScript cDNA Synthesis Kit according to the manufacturer's instructions from (Bio-Rad, Hercules Calif.). For real time PCR, synthesized cDNA forward and reverse primers along with the iQ SYBR Green Supermix (Bio-Rad, Hercules Calif.) were run on the MyIQ Realtime PCR System (Bio-Rad, Hercules Calif.). Sequences of the primers used are listed in Table 2 below and were designed with Primer Bank (Xu, V. et al. Nucleic Acids Res 31, 5582 (2003)).

TABLE 2

| Primer Sequences | | |
|---|---|---|
| Primer | Sequence | SEQ ID NOS |
| 36B4 F | GACCATTAGCCTTGTGTGTACTGTATG | 18 |
| 36B4 R | TGGATCGATTGTGCTTCAAGTT | 19 |
| MAP4K4 F | CATCTCCAGGGAAATCCTCAGG | 20 |
| MAP4K4 R | TTCTGTAGTCGTAAGTGGCGTCTG | 21 |
| TNF-a F | CCCTCACACTCAGATCATCTTCT | 22 |
| TNF-a R | GCTACGACGTGGGCTACAG | 23 |
| IL-1b F | GCAACTGTTCCTGAACTCAACT | 24 |
| IL-1 b R | ATCTTTTGGGGTCCGTCAACT | 25 |
| IL-10 F | CTGGACAACATACTGCTAACCG | 26 |
| IL-10 R | GGGCATCACTTCTACCAGGTAA | 27 |
| CCR2-F | ATCCACGGCATACTATCAAGATC | 28 |
| CCR2-R | CAAGGGTCACCATCATGGTAG | 29 |
| OAS1-F | ATTACCTCCTTCCCGACACC | 30 |
| OAS1-R | CAAACTCCACCTCCTGATGC | 31 |
| MX1-F | GATCCGACTTCACTTCCAGATGG | 32 |
| MX1-R | CATCTCAGTGGTAGTCAACCC | 33 |
| IL-12p40-F | AGACATGGAGTCATAGGCTCTG | 34 |
| IL-12p40-F | CCATTTTCCTTCTTGTGGAGCA | 35 |
| aP2 | CGACCACAATAAAGAGAAA | 36 |

The ribosomal mRNA, 36B4 (Aouadi, M. et al., *Diabetes* 55, 281 (2006), hereby incorporated by reference in its entirety) was used as an internal loading control, as its expression did not change over a 24 h period with the addition of LPS, TNF-α, or the silencing of the genes used in this study. Relative gene expression levels were determined using the delta CT method (Livak, K. and Schmittgen, T., *Methods* 25, 402 (2001)).

siRNA Sequences siRNA experiments utilized GeRPs containing siRNA with sequences as found below in Table 3.

TABLE 3

| | | siRNA sequences | | | |
|---|---|---|---|---|---|
| | Accession numbers | siRNA sequence | SEQ ID NOS | Percentage in vitro knockdown | Percentage in vivo knockdown |
| Scramble | — | 5'-CAGUCGCGUUUGCGACUGG-3' | 14 | 0 | 0 |
| Map4K4 (1) | NM_008696 | 5'-GACCAACUCUGGCUUGUUA-3' | 1 | 72 | 70 |
| Map4K4 (2) | | 5'-CAGAAGUGGCCAAGGGAAA-3' | 15 | 60 | 60 |
| TNF-α (1) | NM_013693 | 5'-CUGUUGGUUGAUCACCACG-3' | 2 | 40 | 33 |
| TNF-α (2) | | 5'-GCAUGGAUCUCAAAGACAA-3' | 16 | 31 | 54 |
| aP2 | NM_024406 | 5'-CGACCACAAUAAAGAGAAA-3' | 17 | | |

Animals. GeRP i.p. Injection.

10 week-old C57BL6/J male mice were i.p. injected daily for 3 days, from day 1 to day 3, with $2 \times 10^9$ GeRPs/kg (4 mg/kg) containing 10 µg/kg scrambled (Scr) or MAP4K4 siRNA. On day 4, mice were i.p. injected with thioglycollate and PECs isolated on day 5. GeRP gavage. 10 week-old C57BL6/J male mice were administered $4 \times 10^9$ GeRPs/kg (8 mg/kg) containing 10 µg/kg Scr or MAP4K4 siRNA by daily oral gavage for 8 days, from day 1 to day 8. To minimize gastric acid secretion due to food ingestion, mice were fasted 2 h before and after gavage. On day 9, mice were i.p. injected with thioglycollate, and PECs and cells from spleen, liver, lung and muscle were isolated on day 10. Spleen, liver, lung and muscle tissues were cut into small pieces, washed with Dulbecco's phosphate-buffered saline (PBS) and digested at 37° C. for 30 min. with agitation using 10 mg/ml collagenase. Digested tissues were then filteres through a 70 mm pore nylon mesh filter (VWR) and centrifuged 10 min at 2000 rpm. Cells were plated in plastic dishes for 3 h, followed by washing and adherent cells were used for the experiments.

LPS Lethality Test.

11 week old mice (20-25 g) treated with GeRPs containing Scr or MAP4K4 siRNA according to the protocol of FIG. 5A were i.p. injected with a single dose of D-galactosamine (25 mg per mouse) followed by an i.p. injection of *E. coli* LPS (0.25 µg per mouse) in a total volume of 0.2 ml of PBS containing 1% BSA. Animals were monitored for lethality for 24 h after LPS/D-GalN challenge (n=22 per treatment group). Blood and peritoneal fluid were collected at 1.5 and 4 h after LPS/DGalN injection for TNF-α level measurements. All procedures involving animals were approved by the Institutional Animal Care and Use Committee at University of Massachusetts Medical School.

ELISA Assay

Mouse TNF alpha ELISA kit from (Pierce, Rockland Ill.) was used to measure concentrations of mouse TNF-α in the PEC supernatant, plasma and peritoneal fluid. The ELISA immunoreactivity was quantified by measuring O.D at 450 nm and quantitated by a standard curve.

Histology and TUNEL Assay

Tissue sections were stained with F4/80-AlexaFluor405 antibody and hematoxylin stained. TUNEL assay was performed on liver sections from mice challenged with LPS/D-GalN according to the manufacturer's instructions (Upstate, Lake Placid N.Y.). Histological images were obtained with a Solamere CSU10 Spinning Disk confocal system mounted on a Nikon TE2000-E2 inverted microscope. Images were taken with a multi-immersion 20x objective with a N.A. 0.75; Oil: W.D.=0.35 mm, or a 100x Plan Apo VC objective NA=1.4, Oil: W.D.=0.13 mm. TUNEL images were obtained using a Zeiss Axiovert 200 inverted microscope equipped with a Zeiss AxioCam HR CCD camera with 1,300×1,030 pixels basic resolution and a Zeiss Plan NeoFluar 20x/0.50 Ph2 (DIC II) objective.

Statistics

The distributional characteristics of the outcomes were evaluated by both a visual inspection of histograms and the Kolmogorov-Smirnoz test performed on model residuals. Transformations by natural logarithms were used in some cases to better approximate a normal distribution and to stabilize variances. The observed effects were evaluated by either one-way or multifactorial analysis of variance (ANOVA). In the presence of significant main and/or interaction effects pairwise comparisons were made using the Tukey (HSD) multiple comparisons procedure with the exception of FIG. 5F where the Kaplan-Meier analysis was used. Statistical significance of $p<0.01$ was determined using Log Rank (Mantel-Cox), Breslow and Tarone-Ware tests. Computations were performed using SAS or SPSS Statistical software packages. The data are presented as means+/−SEM.

To optimize the preparation of the nanocomplexes inside YCWP, a series of experiments were carried out to determine the conditions for maximal binding of each layer in the encapsulated nanocomplexes. These studies (Examples 1-5) used tRNA and PEI to form the nanoparticulate cores, DNA as the payload and PEI to coat and protect the DNA payload caged inside YCWP. Each of these polymers was fluorescently labeled with rhodamine, and nanocomplexes prepared using these materials were used to quantify the binding of each layered component.

Example 1

Formation and Optimization of YCWP Encapsulated tRNA/PEI Nanoplex Cores

Figure 2:
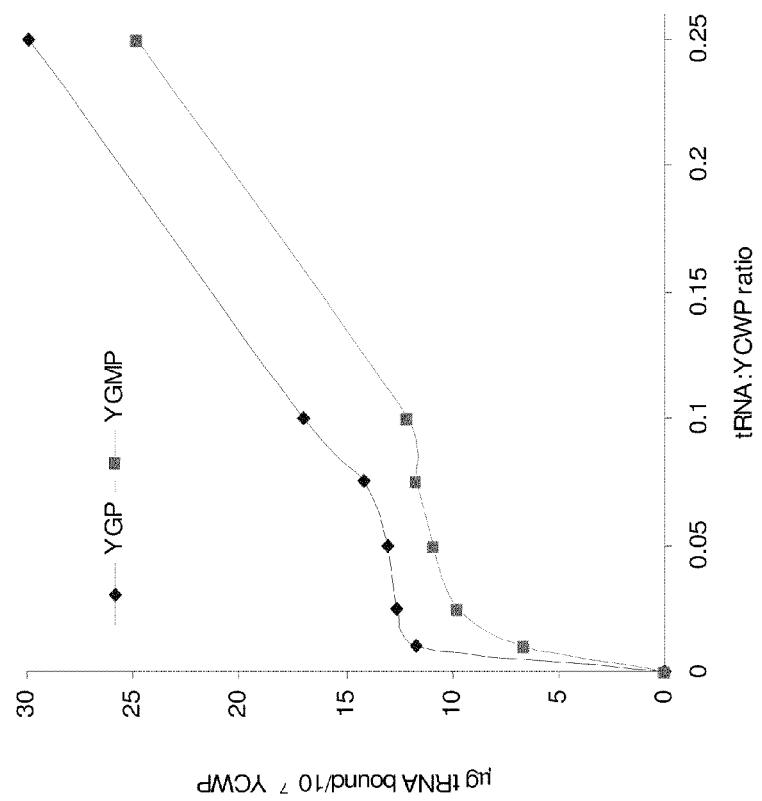
FIG. 2 shows the amount of tRNA (μg) bound within YCWP nanoplex cores as a function of tRNA loaded.

The first step was to characterize and optimize tRNA/PEI concentrations to maximize YCWP-caged nanocomplexed core formation. In these experiments, YCWP encapsulated tRNA:PEI nanocomplexes were prepared at different PEI/tRNA ratios using rhodamine labeled tRNA. The fluorescence of YCWP encapsulated rhodamine labeled tRNA increased as a result of the formation of insoluble PEI:tRNA nanocomplexes within the YCWP. From these measurements it was determined that PEI:tRNA ratios of 5 or higher were necessary to optimally incorporate the tRNA into encapsulated nanocomplexes. At these ratios between 50 to 60% of the tRNA was effectively encapsulated as nanoparticles in the YCWP. The results in FIG. 2 show that it was possible to prepare YCWP encapsulated cationic nanocomplexes containing greater than 30 µg tRNA per 200 µg YCWP particles ($1 \times 10^7$ particles).

The amount of tRNA bound within the nanoplex cores inside $10^7$ YCWP was evaluated at tRNA:YCWP ratios ranging from 0 to 0.25 as indicated in Table 2. FIG. 2 shows the corresponding amount of tRNA in nanoplex cores that the fluorescence signal represents for each tRNA:particle ratio. The tRNA was efficiently incorporated into YCWP encapsulated nanoplexes over the tRNA:particle ratio tested. YGP particles were capable of incorporating more tRNA in nanoplexes than YGMP particles due to their larger hollow internal cavity.

Figure 3:
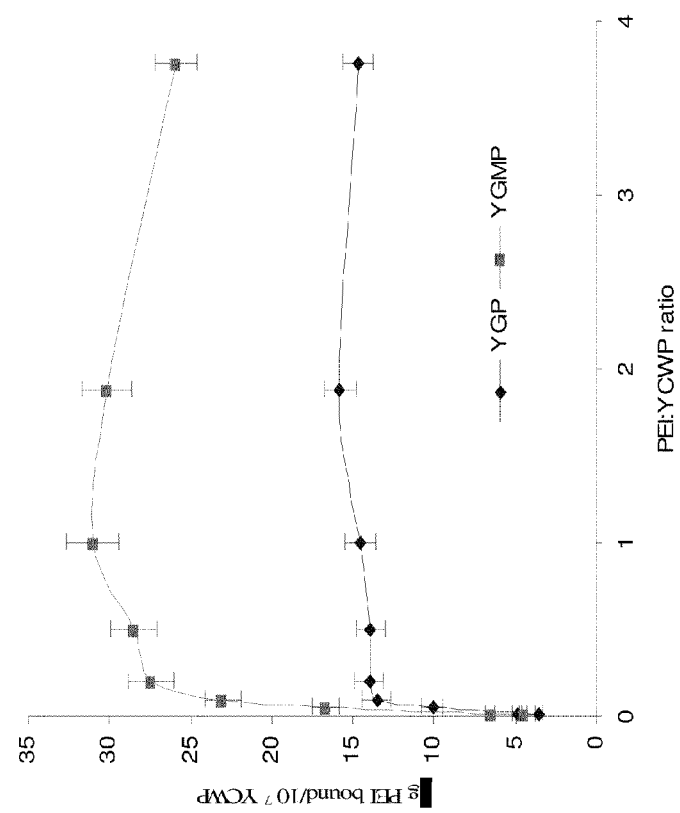
FIG. 3 shows the amount of PEI (μg) bound to tRNA within YCWP to form nanoplex cores as a function of PEI loaded, at a constant tRNA/YCWP ratio of 0.01.

To quantify PEI incorporation within the tRNA:PEI nanocomplexes inside YCWP, a tRNA/YCWP ratio of 0.05 was chosen to prepare cores with different PEI/tRNA ratios. The results in FIG. 3 show that the fluorescence of YCWP nanocomplexed cores with labeled PEI reaches a saturation value at PEI:tRNA ratios as low as 5. Data on binding of tRNA and PEI on a per particle basis, generated by FACS, can be found in Example 4, below.

TABLE 2

Formulations used to evaluate tRNA nanoplex formation inside YCWP

| Sample | Rho-tRNA:YCWP ratio (w/w) | PEI:YCWP ratio (w/w) | PEI:Rho-tRNA ratio (w/w) |
|---|---|---|---|
| 1 | 0.01 | 4 | 400 |
| 2 | 0.025 | 4 | 160 |
| 3 | 0.05 | 1.32 | 26.4 |
| 4 | 0.05 | 4 | 80 |
| 5 | 0.05 | 13.2 | 264 |
| 6 | 0.075 | 4 | 53.3 |
| 7 | 0.1 | 1.32 | 13.2 |

TABLE 2-continued

Formulations used to evaluate tRNA nanoplex formation inside YCWP

| Sample | Rho-tRNA:YCWP ratio (w/w) | PEI:YCWP ratio (w/w) | PEI:Rho-tRNA ratio (w/w) |
|---|---|---|---|
| 8 | 0.1 | 4 | 40 |
| 9 | 0.1 | 13.2 | 132 |
| 10 | 0.25 | 4 | 16 |

The amount of PEI incorporated into the tRNA nanoplex cores inside 107 yCWp was measured at a constant tRNA:YCWP ratio of 0.01 using the formulation ratios shown in Table 2. The results of these studies shown in FIG. 3 indicate that PEI was efficiently incorporated into the tRNA nanoplex cores up to a PEI-tRNA ratio of 10 (w/w). More PEI was bound to YGMP particles at all ratios tested, likely due to cationic PEI binding to negatively charged mannoproteins in the YGMP wall.

TABLE 3

Formulation conditions used to evaluate PEI binding to tRNA nanoplex cores inside YCWP

| Sample | PEI:YCWP ratio (w/w) | PEI:Rho-tRNA ratio (w/w) |
|---|---|---|
| 1 | 0.01 | 1 |
| 2 | 0.02 | 2 |
| 3 | 0.05 | 5 |
| 4 | 0.1 | 10 |
| 5 | 0.2 | 20 |
| 6 | 0.5 | 50 |
| 7 | 1 | 100 |
| 8 | 1.875 | 187.5 |
| 9 | 3.75 | 375 |

The results from these studies allowed for the optimization of tRNA/PEI nanocomplex core formation caged within YCWP to provide sufficient cationic nanoparticle surface area for maximum DNA binding, while leaving enough space within the YCWP for subsequent layers. Optimal conditions for nanoplex core formation required the use of tRNA/YCWP weight ratios between 0.01 to 0.05, and PEI/YCWP weight ratios higher than 0.5.

Example 2

Fluorescence Analysis of the Formation of DNA/PEI Complexes on YCWP-tRNA/PEI Nanocomplex Cores The next step was to optimize DNA binding and PEI coating to form YCWP caged tRNA/PEI/DNA/PEI nanocomplexes. It was observed that DNA must be used within an optimal concentration range to achieve high transfection efficiency, as high DNA levels did not necessarily translate to high transfection levels. It was also important to optimize the PEI formulation step to coat the DNA layer. PEI must completely coat the DNA layer to protect it from degradation before its release inside the cell. However, PEI is toxic and its concentration should be minimized in order to reduce toxicity.

Figure 4:
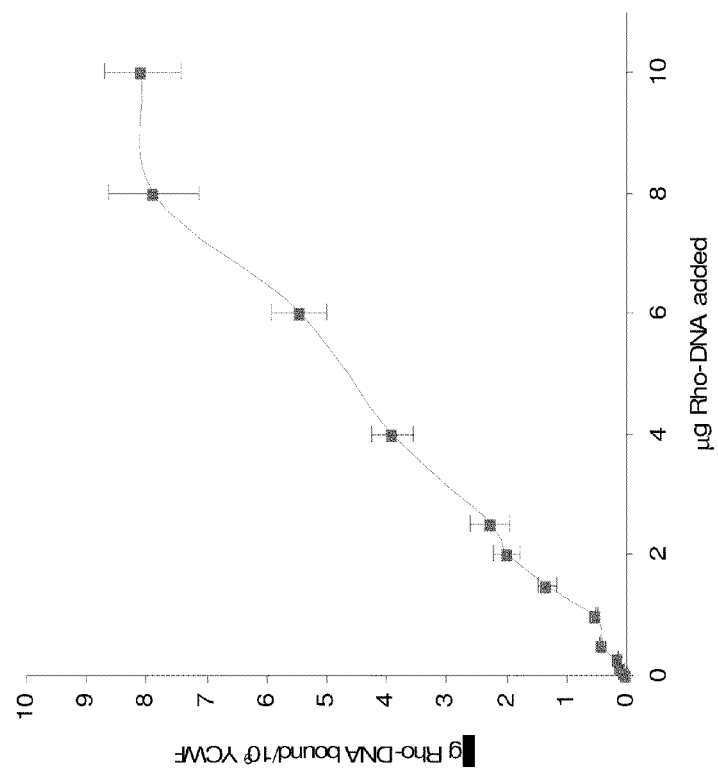
FIG. 4 shows the amount of sonicated rhodamine-labeled salmon sperm DNA bound as a function of DNA concentration (μg of DNA/1×10$^9$ particles).

YCWP formulations of YCWP:tRNA/PEI with a tRNA/YCWP ratio of 0.05 and a PEI/YP ratio of 4 were used as the starting material for the preparation of samples containing fluorescently labeled DNA. Rhodamine labeled DNA was added to this formulation over the range of 0 to 100 μg DNA/1×10$^9$ particles. PEI was then added at a PEI/DNA ratio of 2.5 to coat the DNA layer and prevent the DNA from washing off the tRNA/PEI cationic core surface. FIG. 4 shows the amount of DNA bound for samples that were prepared with sonicated salmon sperm DNA (~5 kDa). DNA was effectively bound (80±10%) over the range of DNA concentrations tested. In comparison, high molecular weight DNA (>40 kDa) was less effectively bound (40±15%) suggesting that the YCWP hydrocolloid matrix partially excludes the penetration of high molecular weight DNA molecules (data not shown). These results show the DNA binding capacity of plasmid sized DNA to be ~8 μg DNA/1×10$^9$ particles (~4 μg DNA/mg particles).

A YCWP/tRNA/PEI particle formulation with a tRNA/YP ratio of 0.05 and a PEI/YP ratio of 4 was used to quantify the amount of Rho-DNA that binds to the encapsulated nanoplex cores. It was found that Rho-DNA loosely binds to the cores as demonstrated by lower particle-associated fluorescence before PEI coating. Once PEI was used to coat the DNA layer, the percentage of DNA associated with the encapsulated cores increased to >80% (FIG. 4).

Example 3

Fluorescence Analysis of Final PEI Layer in the YCWP tRNA-PEI-DNA-PEI Nanocomplex Coating of the DNA layer with a protective trapping polymer layer is important to maximize transfection efficiency. The amount of PEI bound to the DNA layer was measured at different DNA concentrations.

Figure 5:
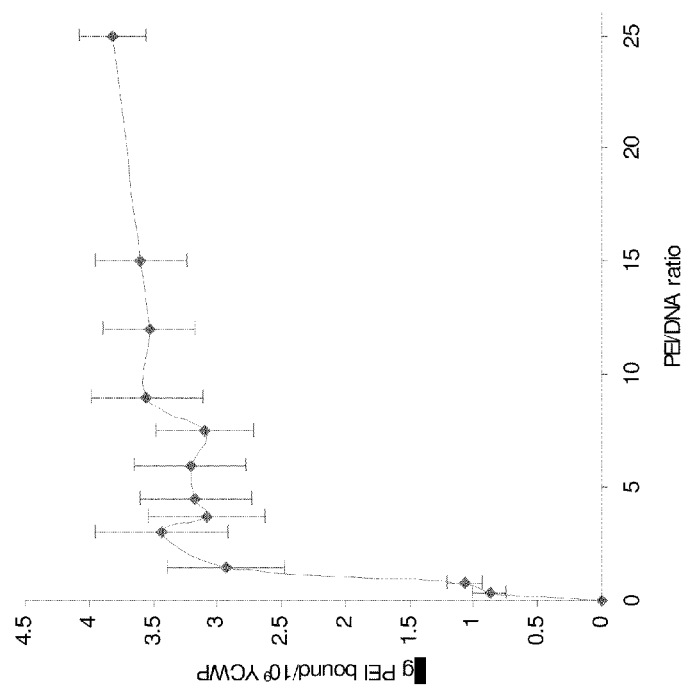
FIG. 5 shows the amount of PEI (μg) bound to YCWP-tRNA-PEI-DNA as a function of PEI loaded at a constant DNA load (10 μg of DNA) with a particle formulation of tRNA:YCWP ratio of 0.05, and PEI:YCWP ratio of 4 w/w.

A YCWP/tRNA/PEI particle formulation with a tRNA/YP ratio of 0.05, a PEI/YP ratio of 4 and a constant load of 10 μg of DNA/1×10$^9$ particles (DNA/YP ratio of 0.005) was used to quantify the amount of Rho-PEI coating of the encapsulated nanoplex cores. The results in FIG. 5 show that PEI can be used at PEI/DNA ratios as low as 3:1 as the fluorescence response for Rhodamine-PEI trapped inside the particles reaches a plateau at this PEI/DNA ratio. This PEI/DNA weight ratio of 3:1 is equivalent to an N/P ratio of ~8. For 25 kDa PEI, a critical N/P ratio of 2.3:1 has been reported for formation of DNA/PEI nanoparticles, while N/P ratios of 6-8 are considered the minimum necessary for efficient DNA condensation and protection during DNA delivery to cells. Therefore, the required N/P ratio for DNA condensation within YCWP is found in the proper range reported by others for DNA/PEI nanoparticle formation.

It was determined that PEI adsorption reaches a maximum value at a PEI:DNA ratio higher than 3:1 (w/w) (FIG. 5).

Example 4

Per-Particle Analysis Via Flow Cytometry (FACS) and Fluorescence Microscopy

Figure 6:
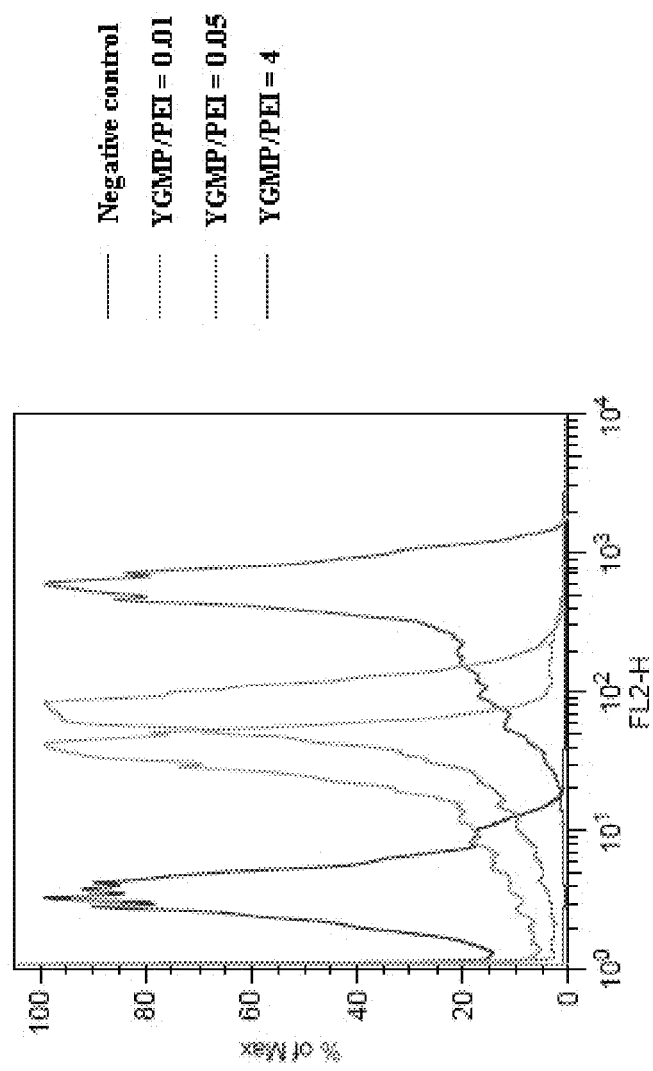
FIG. 6 contains FACS results showing the uniform increase of fluorescence from Rho-PEI bound to YGMP-tRNA cores at different YGMP/PEI ratios.
Figure 7:
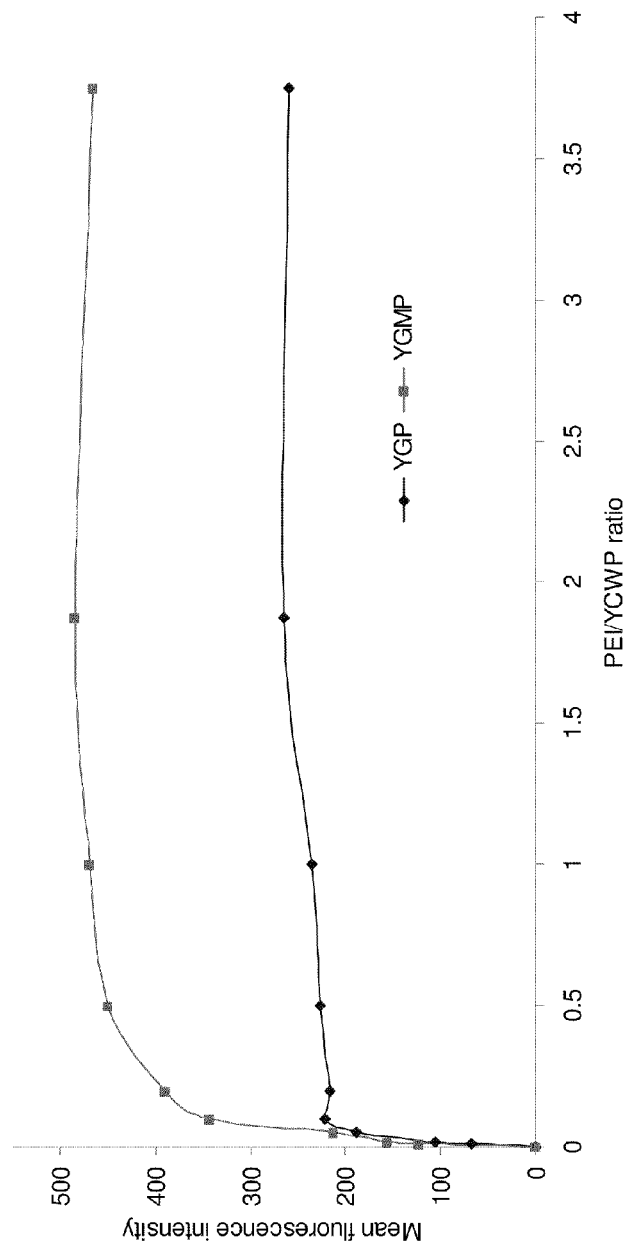
FIG. 7 shows the mean fluorescence intensity for Rho-PEI binding to both YGP and YGMP.
Figure 8:
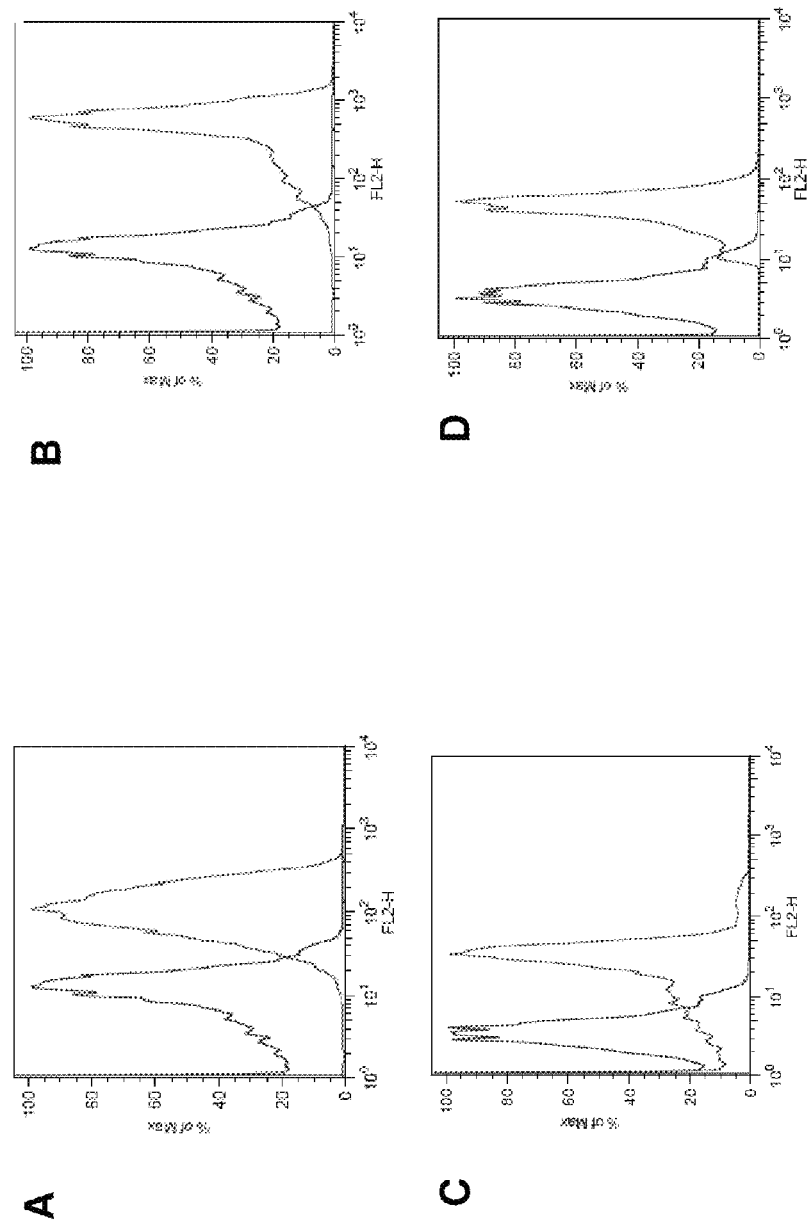
FIG. 8 displays FACS results (blue lines indicate negative controls) showing adsorption of DNA/PEI complexes: (A) Rho-tRNA adsorbed in YGMP at tRNA/YGMP ratio of 0.1; (B) Rho-PEI bound to YGMP-tRNA at a PEI/YGMP ratio of 3.75; (C) Adsorption of 625 ng Rho-DNA to 109 YGMP/tRNA/PEI particles; (D) Adsorption of Rho-PEI to YCWP-tRNA-PEI-DNA (25 μL of 0.01% Rho-PEI added to 500 ng of DNA).

FACS measurements were obtained for different sets of titration experiments in order to quantitate tRNA, PEI or DNA binding on a per particle basis, and to assess the homogeneity of nanocomplex formation within YCWP. An example of this quantification is provided in FIGS. 6 and 7 for nanoparticle core formation. The FACS results show the fluorescence of Rhodamine labeled PEI bound to the YGP-tRNA core uniformly increases as the fluorescent PEI/YGMP-tRNA ratio increases (FIG. 6). In addition, a maximum fluorescence response of the same magnitude is observed for PEI/YCWP ratios greater than 1 (FIG. 7), confirming the bulk fluorescence measurements. Similar results were obtained for analysis of other layers (data not shown). FIG. 8 shows the maximum response for Rho-tRNA at YGMP/tRNA ratio of 0.05 (panel A), and for Rho-PEI at a PEI/YGMP ratio of 4 (panel B). DNA binding to YCWP-tRNA-PEI nanocomplexes was evaluated on a per particle basis following fluorescent DNA binding by FACS. The FACS analysis (FIG. 8, panel D) shows that >95% of the particles bind DNA. The formation of the final PEI layer of the YCWP-tRNA-PEI-DNA-PEI nanocomplexes was evaluated on a per particle basis following fluorescent PEI binding. The FACS analysis (FIG. 7, panel E) shows that >85% of the particles bind PEI to levels detected by FACS analysis.

The use of FACS allowed us to quantify tRNA and PEI binding on a per particle basis. The results for Rho-PEI in FIG. 8 show a uniform increase in fluorescence with increasing Rho-PEI/YCWP-tRNA ratio demonstrating homogeneous nanocomplex formation within YCWP. At a Rho-PEI/YCWP-tRNA ratio of 1 or higher the measured fluorescence reaches a constant value thus indicating the saturation value for PEI. These results support the experimental values for core formation determined from bulk fluorescence measurements Example 5

Transfection Results on Cells In Vitro

The impact of the optimization of the LbL assembly process of encapsulated DNA coated nanoplex cationic cores on transfection efficiency was assessed following the YCWP mediated delivery of the plasmid gWizGFP to cultured cells. Transfection experiments were carried out using NIH3T3-D1 cells. This cell line was derived from NIH3T3 by the integration of the dectin-1 gene to produce cells expressing cell surface dectin-1 allowing for YCWP phagocytosis. Several particle formulations using varied tRNA/YP ratios at a constant PEI/YP ratio of 4 were evaluated. The transfection results for particle formulations with two different tRNA/YP ratios and a constant PEI/YP ratio of 4 are shown in FIG. 9.

Figure 9:
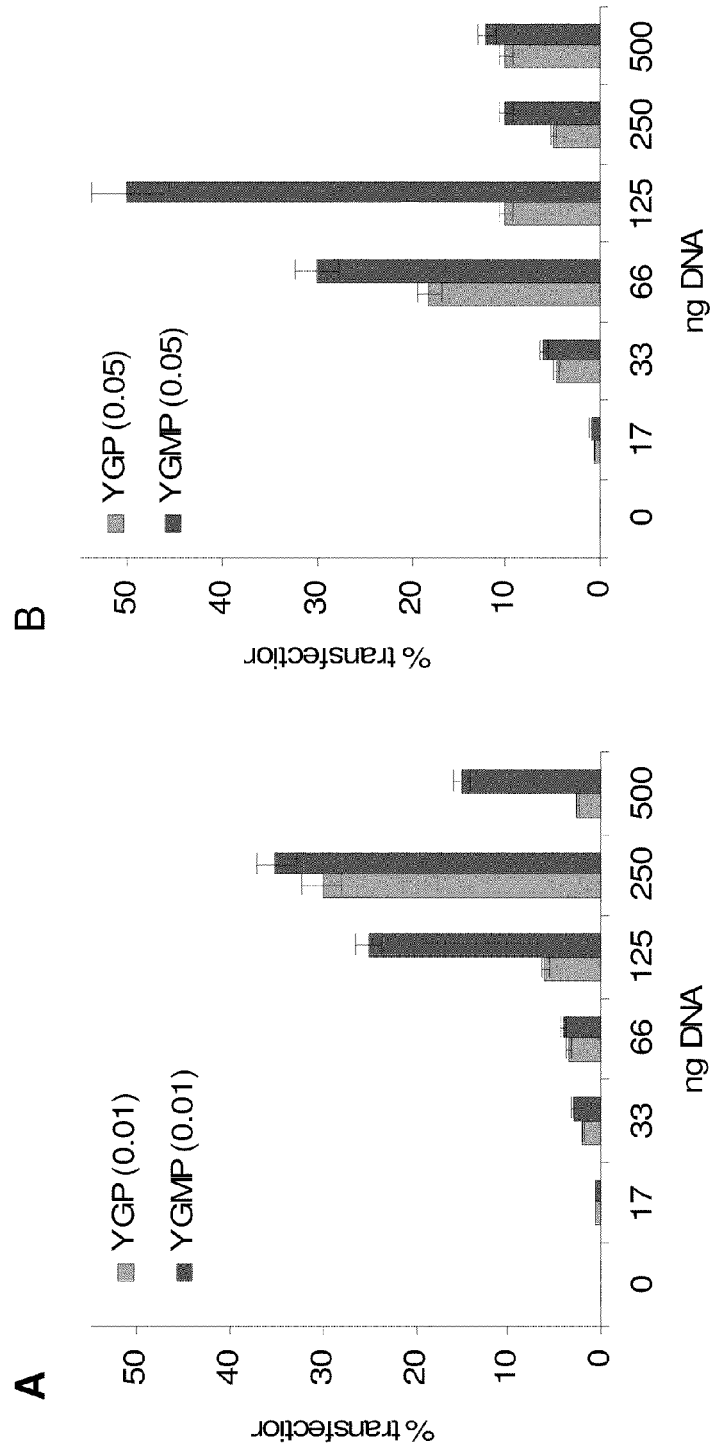
FIG. 9 shows transfection results for YCWP-tRNA-PEI particles with tRNA/YCWP ratios of 0.01 (A) and 0.05 (B), and PEI/YCWP ratio of 4.

FIG. 9 shows the transfection results at different DNA loads for two formulations that consistently provided highest transfection results. DNA delivered in the optimized YCWP delivery system efficiently transfects NIH3T3-D1; greater than 50% of cells are transfected by 125 ng DNA/$1\times10^5$ cells) when using a YGMP formulation with a tRNA/YGMP ratio of 0.05. Transfection efficiency of DNA/PEI nanocomplexes not trapped inside YCWP was negligible at a DNA load of 125 ng/$1\times10^5$ cells. In comparison, other groups have reported efficient transfection with DNA/PEI nanocomplexes, but it requires at least 16-fold the amount of plasmid DNA delivered/cell compared to the amount required with the YCWP delivery system to obtain transfection levels higher than 50%.

The following examples illustrate the effectiveness of YCWP-encapsulated nanoparticle delivery of nucleic acid payload agents to mammals. siRNAs were delivered to mice via injection and oral delivery and were able to knock down expression of target genes in vivo.

In particular, the examples demonstrate the use of encapsulated siRNA nanoparticles that potently silence genes in mouse macrophages in vitro and in vivo. Using this methodology, it is demonstrated that the mitogen activated protein 4 kinase 4 (MAP4K4) is a novel mediator of inflammatory responses. Oral delivery of as little as 10 ug/kg siRNA depleted MAP4K4 in macrophages recovered from peritoneum, spleen, liver and lung in mice. Importantly, silencing MAP4K4 in macrophages protected mice from lipopolysaccharide-induced lethality by inhibiting tumor necrosis factor alpha and interleukin-1 beta production. These results provide a novel strategy for oral delivery of siRNA to attenuate inflammatory responses in human disease. In particular, the strategy provides for the selective, safe delivery of siRNAs to target tissues in vivo.

The discovery that short sequences of double stranded RNA can cause depletion of cognitive RNA transcripts in eukaryotic cells has greatly expanded our understanding of gene regulation (Fire, A. et al. Nature 391, 806-11 (1998)). The specificity and potency of gene silencing by RNA interference (RNAi) is facilitated by cellular machinery that mediates these actions. For therapeutic applications, double stranded short interfering RNA (siRNA) oligonucleotides are relatively nontoxic, readily designed for high specificity, and need not be restricted to genes that encode proteins that bind small molecule drugs (Grimm, D. & Kay, M. A. J Clin Invest 117, 3633-41 (2007); Elbashir, S. M. et al. Nature 411, 494-8 (2001)). Thus RNAi can be targeted to all genes that encode protein sequences. Additionally, siRNAs are designed to minimize the interferon response associated with exposure of cells to long sequences of double stranded RNA (Bridge, A. J. et al., Nat Genet. 34, 263-4 (2003); Xiang, S. et al., Nat Biotechnol 24, 697-702 (2006)). Despite these properties, challenges to in vivo delivery of siRNA remain. These include rapid degradation of siRNA oligonucleotides in extracellular environments, rapid excretion through the kidney, and low permeability through tight junctions and across cell surface membranes (Xie, F. et al. Drug Discov Today 11, 67-73 (2006); Sioud, M. & Sorensen, D. R., Methods Mol Biol 252, 515-22 (2004)). Creative efforts have addressed some of these problems, and a few clinical trials are underway (Akhtar, S. & Benter, I. F., J Clin Invest 117, 3623-32 (2007)). However, a key goal in the field is to develop techniques that orally deliver siRNA-mediated gene silencing to specific target tissues and cell types.

The studies described in Examples 6-15 achieve this goal. The macrophage was identified as a potential target because it controls inflammatory responses associated with such major diseases as rheumatoid arthritis, colitis, and atherosclerosis. As a specialized host defense cell, the macrophage is a validated pharmaceutical target that contributes to pathogenesis through secretion of such inflammatory cytokines as tumor necrosis factor alpha (TNF-α) and interleukin-1 beta (IL-1β) (Duffield, J. S., Clin Sci (Lond) 104, 27-38 (2003); Moghimi, S. et al. Pharmacol Rev 53, 283-318 (2001)). To accomplish oral delivery of siRNA to macrophages in mice, micron-sized particles of β1,3-D-glucan were used which have distinctive characteristics that allow their passage through M cells in Peyer's patches in the intestinal wall to the underlying gut associated lymphatic tissue (GALT) (Beier, R. & Gebert, A., Am J Physiol 275, G130-7 (1998); Hong, F. et al. J Immunol 173, 797-806 (2004), both of which are hereby incorporated by reference in their entirety). Following transcytosis of such β1,3-D-glucan particles into the GALT, they undergo phagocytosis by resident macrophages and dendritic cells via the dectin-1 receptor and perhaps other beta glucan receptor-mediated pathways (Herre, J. et al. Mol Immunol 40, 869-76 (2004); Willment, J. et al. J Biol Chem 276, 43818-23 (2001), both of which are hereby incorporated by reference in their entirety). GALT macrophages traffic away from the gut and infiltrate other reticuloendothelial system tissues, such that over time a significant proportion of total body macrophages contain ingested glucan particles.

Hollow, porous micron-sized shells composed primarily of β1,3-D-glucan were prepared by treating baker's yeast with a series of alkaline, acid and solvent extractions to remove cytoplasmic components, as well as other cell wall polysaccharides (FIG. 1c; Soto, E. & Ostroff, G. R., NSTI Nanotech 2007 Technical Proceedings 2, 378-381 (2007), hereby incorporated by reference in its entirety). Such hollow glucan shells are about 2-4 microns in diameter. Layer by layer nanoparticle synthesis methods were then developed to load them with siRNA, yielding β1,3-D-glucan-encapsulated siRNA Particles (GeRPs), as depicted in FIG. 1c. First, a nanoparticulate core of anionic material (RNA, DNA or other negatively-charged polymer) is synthesized within the glucan shells by electrostatic nanoplex formation with a cationic polymer. The positively-charged nanocores inside the glucan shells electrostatically absorb the anionic siRNA payload (optionally along with Endoporter) to form GeRPs. Next is added a layer of a cationic polymer, such as PEI, chosen for its effective action as a transfection agent and its relative low toxicity in vivo (Boussif, O. et al. Proc Natl Acad Sci USA 92, 7297-301 (1995)). Additional layers of anionic siRNA and cationic PEI can be applied to synthesize multi-layered GeRPs composed of single or multiple siRNAs. The anionic siRNA within GeRPs is bound between cationic polyethylenimine (PEI) layers through electrostatic interactions in a pH-dependant manner. Upon phagocytosis by macrophages, GeRPs traffic to the endosomal compartment, where the acidic pH changes the layers' charge. This promotes siRNA release from the multi-layered nanoparticulate complex through the porous GeRP wall and endosomal membrane into the macrophage cytoplasm.

To test GeRP formulations for siRNA-mediated gene silencing in macrophages, mouse peritoneal exudate cells (PECs) were prepared after intraperitoneal (i.p.) thioglycollate injection, as described in Materials and Methods, above. Preliminary experiments using a variety of siRNAs encapsulated within GeRPs showed extensive phagocytosis of GeRPs by the primary macrophages and significant gene silencing (for example, see TNF-α siRNA, FIG. 10).

Example 6

In Vitro Macrophage Uptake of siRNA-Containing Fluorescent YCWP (FITC-YCWP) and Subsequent Gene Silencing Ten-week old C57BL6/J mice were IP (intra-peritoneally) injected with an inflammatory agent (thioglycollate). Four days after injection, chemo-attracted macrophages were isolated from the peritoneum and plated. Macrophages attached to the plates and erythrocytes were eliminated by washes. $1 \times 10^6$ cells were treated with $1 \times 10^7$ FITC-YCWP particles (YCWP incorporating a green fluorescent dye) containing 0.25 ug or 40 pmoles of siRNA directed against Map4k4, TNF-alpha and RIP140 genes. 48 hours after treatment, confocal analysis were performed using a macrophage specific antibody, F4/80, coupled to an AlexaFluor405 probe (blue) on a portion of the macrophages. Fluorescent microscopy revealed green fluorescence localized within blue-labeled macrophages, indicating that the FITC-YCWP had been taken up and internalized by the macrophages.

Figure 11:
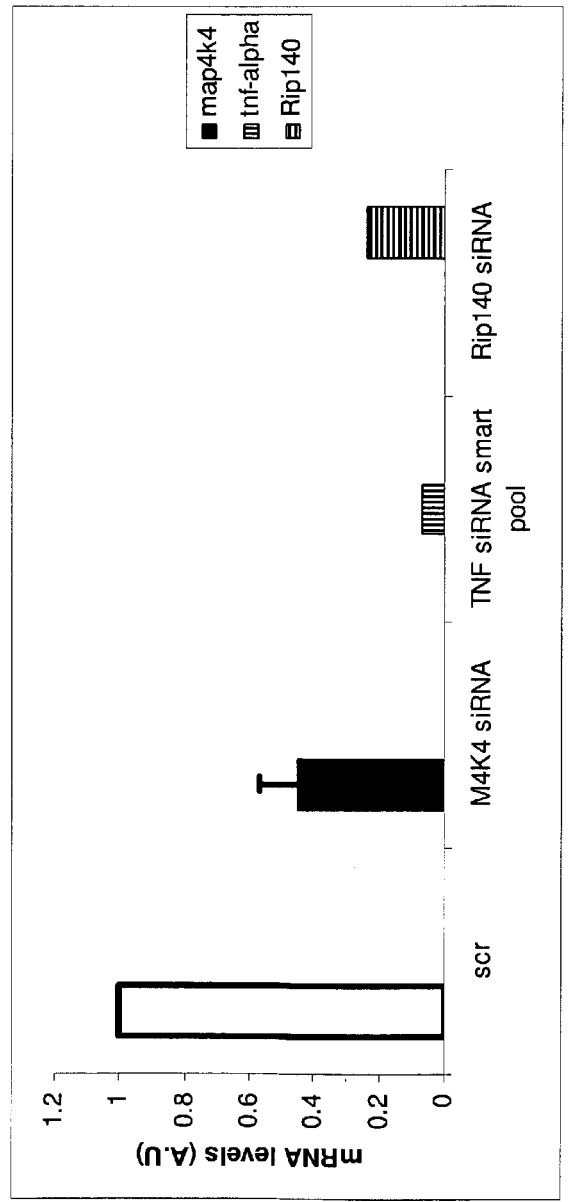
FIG. 11 shows that the expression levels for Map4k4, TNF-alpha and RIP140 in mouse peritoneal macrophages 48 hours after treatment with GeRPs containing siRNA species directed against Map4k4, TNF-alpha and RIP140.

Macrophages were harvested at 48 hours post-treatment with the siRNA-containing FITC-YCWP. Total RNA was isolated to measure gene expression using real-time PCR. FIG. 11 shows that the expression levels for Map4k4, TNF-alpha and RIP140 were all reduced as compared to SCR (y-axis: Absorbance Units). The 36B4 gene as used as an internal control (not shown). 'Scr' is scrambled RNAi, which comprises randomized RNA sequences that do not correspond to any known gene. Thus scr RNA does not knock down any known gene and serves as a negative control.

Figure 10:
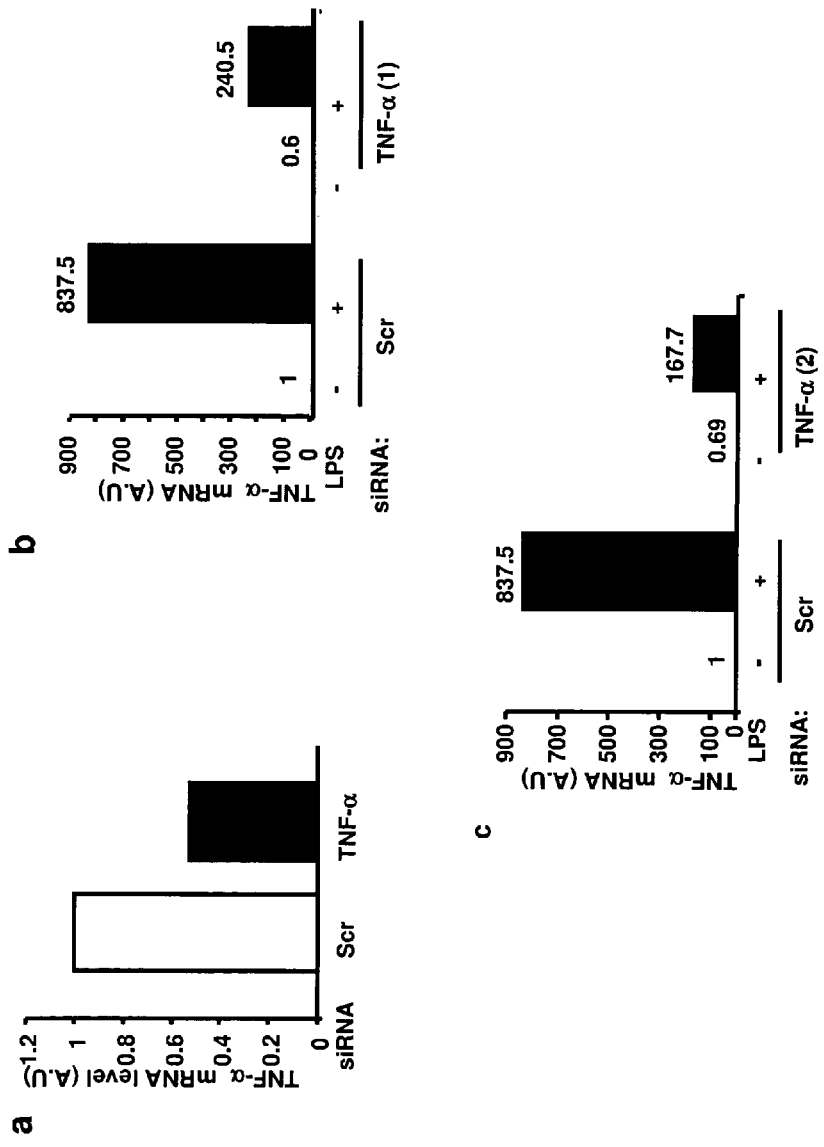
FIG. 10a-c shows that TNF-α siRNA-GeRPs effectively silence basal TNF-α mRNA expression (FIG. 10a, TNF-α mRNA in TNF-α siRNA sample relative to TNF-α mRNA in the Scr siRNA sample.

Similar results were obtained using a specific TNF-alpha siRNA (1), 5'-CUGUUGGUUGAUCACCACG-3' (SEQ ID NO: 2). $1 \times 10^6$ PECs were treated with $1 \times 10^7$ FITC-YCWP/GeRPs containing 40 pmoles of Scr or TNF-α siRNA. Total RNA was harvested 48 hours after treatment and analyzed by RT-PCR for the expression of TNF-α. FIG. 10 shows that TNF-α siRNA-GeRPs effectively silenced basal TNF-α mRNA expression (both for TNF-α siRNA sequence 1 (TNF-α (1)) and TNF-α siRNA sequence 2 (TNF-α (2)).

Figure 12:
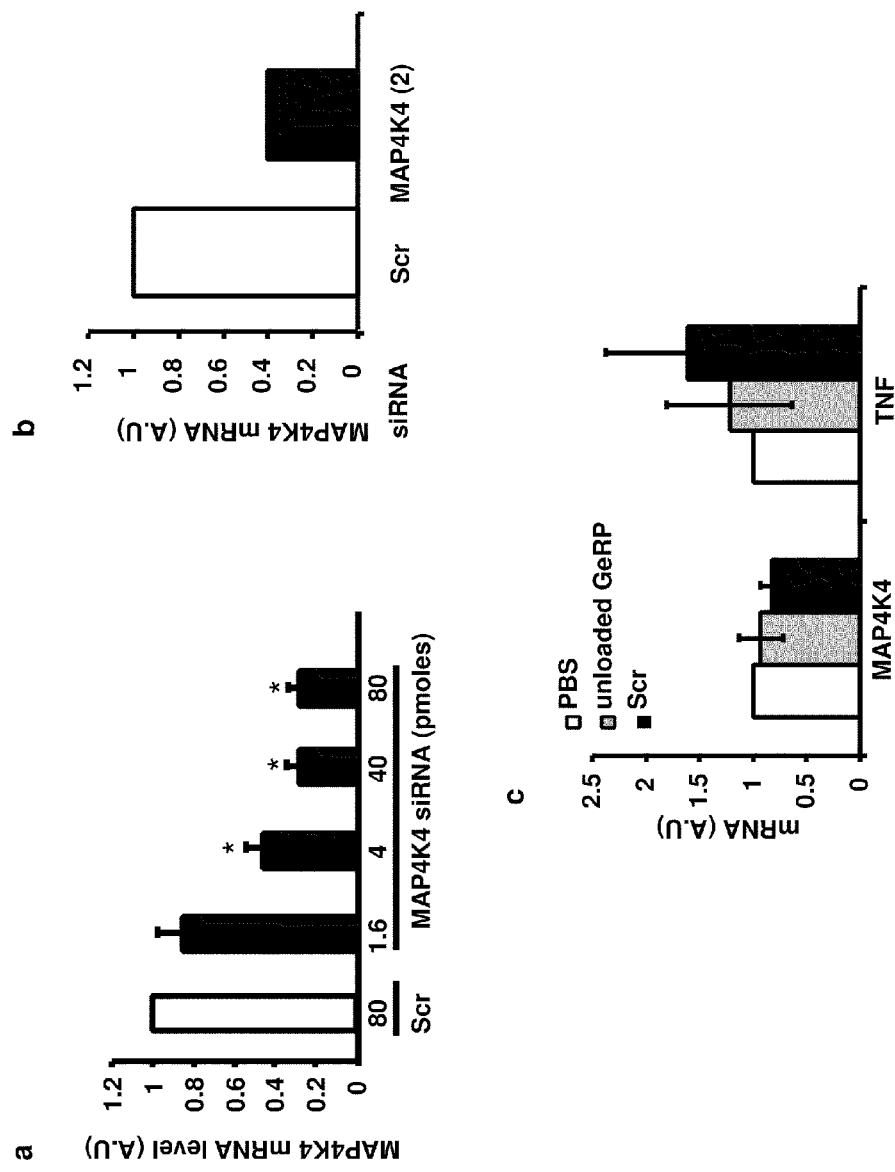
FIGS. 12a and 12b show in vitro MAP4K4 mRNA expression in MAP4K4 siRNA-GeRP treated PECs as assessed by RT-PCR quantification
FIG. 12c shows the effects of treatment with PBS, unloaded GeRPs and GeRPs loaded with scr siRNA on MAP4K4 and TNFα mRNA expression in PECs.

This system of gene silencing was then used in primary macrophages to test whether candidate intracellular signaling proteins might control TNF-α expression. One of these was the Mitogen Activated Protein 4 Kinase 4 (MAP4K4), a germinal center protein kinase that we and others found facilitates TNF-α signaling itself (Bouzakri, K. & Zierath, J. R., J Biol Chem 282, 7783-9 (2007); Tesz, G. J. et al. J Biol Chem 282, 19302-12 (2007); Yao, Z. et al. J Biol Chem 274, 2118-25 (1999); Tang, X. et al. Proc Natl Acad Sci USA 103, 2087-92 (2006), all of which are hereby incorporated by reference in their entirety). In these experiments, glucan shells were first derivatized with a green fluorescein (FL) probe. They were then loaded with Scrambled (Scr) or MAP4K4 siRNA (1)(5'-GACCAACUCUGGCUUGUUA-3' (SEQ ID NO: 1)) coupled to the red fluorescent probe, Dy547, using the layer by layer synthesis methods to prepare GeRPs, as described in Materials and Methods, above. PECs were incubated in vitro with these double labeled Scr siRNA- or MAP4K4 siRNA-containing GeRPs (10:1 particle-to-cell ratio), with unloaded GeRPs or with PBS (control) for 12 hours, and then stained with the macrophage specific F4/80-AlexaFluor405 antibody. About 90% of the macrophages had internalized at least one FL-GeRP, as visualized by fluorescein or Dy547-siRNA fluorescence, while most cells had internalized multiple FL-GeRPs. Using the GeRPs containing MAP4K4 siRNA, a 70-80% knockdown of MAP4K4 mRNA was achieved in $10^6$ PECs with as little as 40 pmoles siRNA (FIG. 12a and b: (1.6, 4, 40 or 80 pmols of MAP4K4 siRNA (1) in panel a; 40 pmols of MAP4K4 siRNA (2) in panel b). No significant differences in expression levels of MAP4K4 mRNA or TNFα mRNA were seen between macrophages treated with Scr siRNA-containing GeRPs, unloaded GeRPs and PBS (control: no GeRPs) (FIG. 12c).

Example 7

Oral and IP Injection Delivery of FITC-YCWP in Mice

Ten-week old C57BL6/J mice were treated with 100 ug ($5 \times 10^7$) by IP injection or 200 ug ($1 \times 10^8$) FITC-YCWP by oral gavage everyday for 3 or 10 days. After 3 or 10 days, blood samples were drawn and spleens were fixed and stained. Spleen tissue sample were stained with F4/80 macrophage-specific antibody coupled to peroxidase and analyzed for fluorescence. Microscopy revealed that the peroxidase signal was co-localized with fluorescence in the spleen tissue sections.

Figure 13:
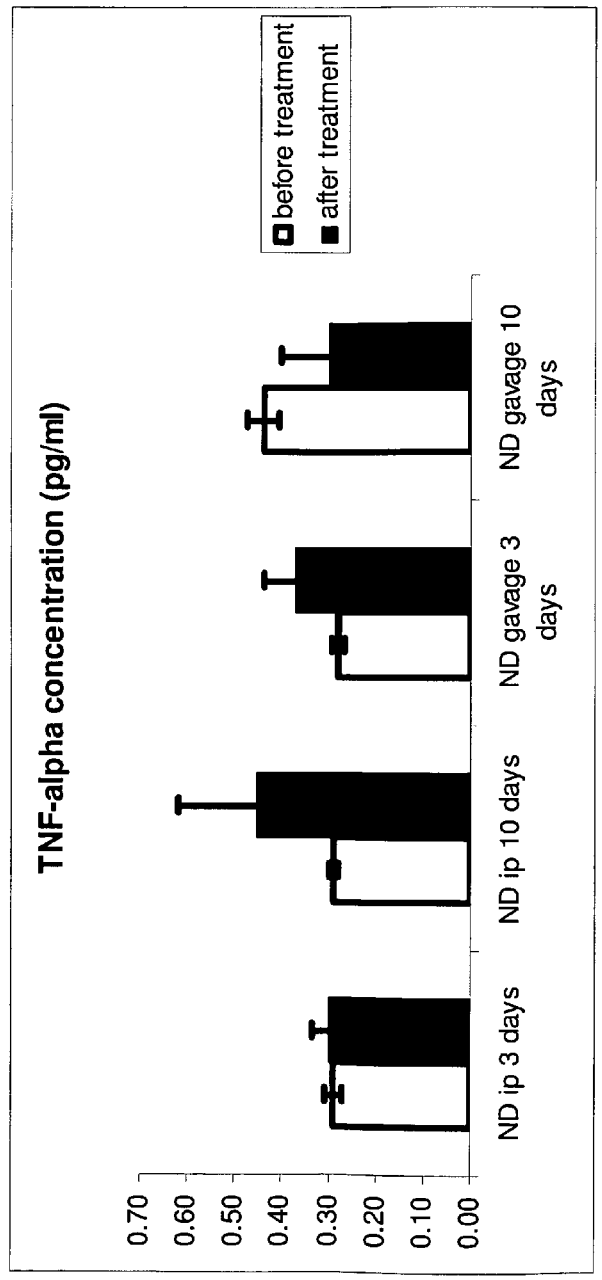
FIG. 13 shows TNF-alpha concentrations in plasma from blood samples taken before and after treatment with control FITC-YCWP containing no siRNA.

TNF-alpha concentrations in plasma from blood samples taken before and after treatment were analyzed. As seen in FIG. 13, no significant effect was observed on serum TNF-alpha levels in response to the administration of the control FITC-YCWP (containing no siRNA).

Example 8

In Vivo Silencing of Map4k Using IP Injected, siRNA-Loaded FITC-YCWP

Figure 14:
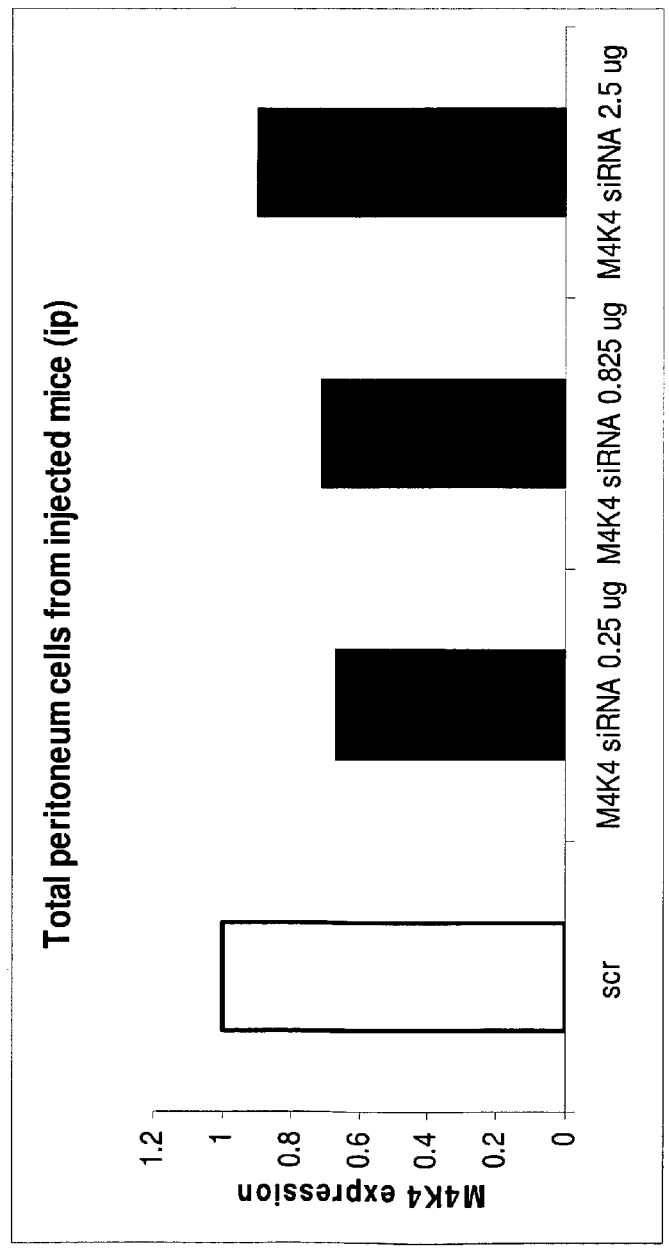
FIG. 14 shows Map4k4 expression from a pool of mouse peritoneal macrophages isolated from mice that had been previously injected with GeRPs containing anti-Map4k4 siRNA.
Figure 15:
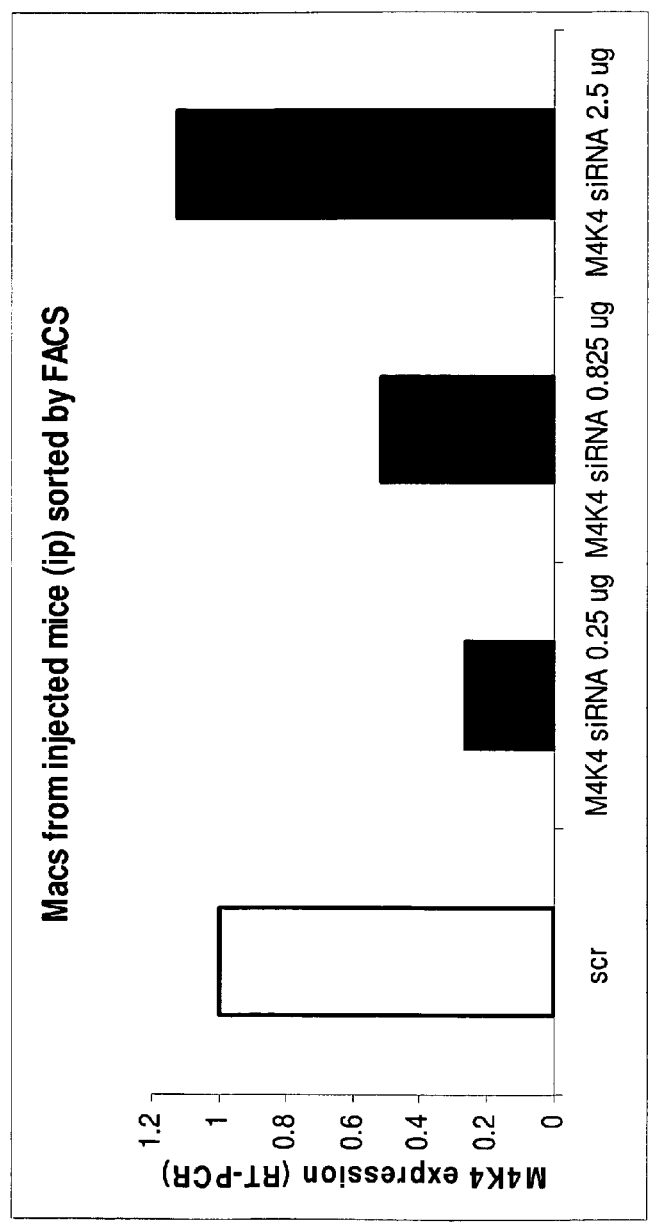
FIG. 15 shows Map4k4 expression from mouse peritoneal macrophages isolated from mice injected with GeRPs containing Map4k4 siRNA that had also been sorted for fluorescence using FACS.

Ten-week old C57BL6/J mice were IP injected daily for 3 days, with 100 ug ($5 \times 10^7$) FITC-YCWP, containing 0.25 ug, 0.825 ug and 2.5 ug of scrambled (control) or Map4k4 siRNA. Twenty-four hours after the last dose, mice were IP injected with thioglycollate. Chemo-attracted macrophages were isolated from the peritoneum 24 hours after the thioglycollate injection. RNA was isolated from total peritoneum cells (macrophages and erythrocytes; data shown in FIG. 14) or FITC-positive cells sorted by FACS (FIG. 15). Map4k4 expression was measured using real time PCR. The 36B4 gene was used as an internal control.

The results show that delivery of 0.25 ug and 0.825 ug of Map4k4 siRNA with YCWP significantly reduced Map4k4 expression in peritoneum cells. The reduced effectiveness of the largest amount of siRNA in reducing gene expression is consistent with data from the siRNA field: delivering a large amount of RNA into a cell (by any means) triggers cellular responses that interfere with silencing mechanisms, likely by activating nucleases that degrade the RNA.

Example 9

Figure 16:
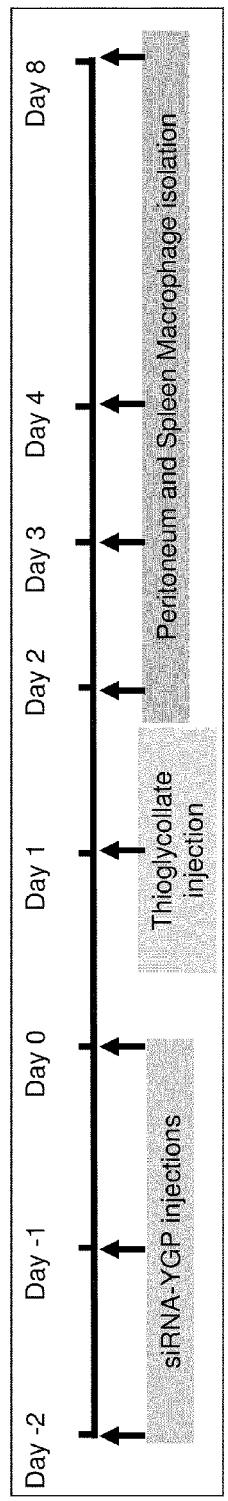
FIG. 16 shows the timeline for the treatments and cell isolations from mice in the experiment detailed in Example 9.
Figure 17:
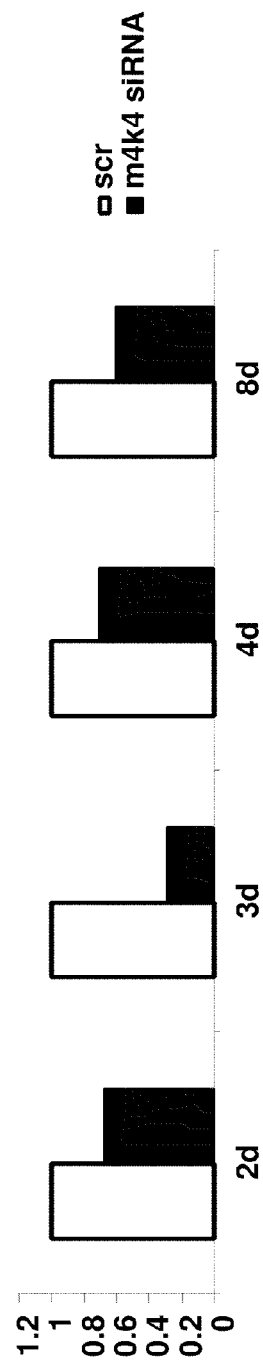
FIG. 17 shows Map4k4 expression in peritoneal macrophages that were isolated from mice injected with GeRPs containing Map4k4 siRNA or control FITC-YCWP at various timepoints after the last injection.
Figure 18:
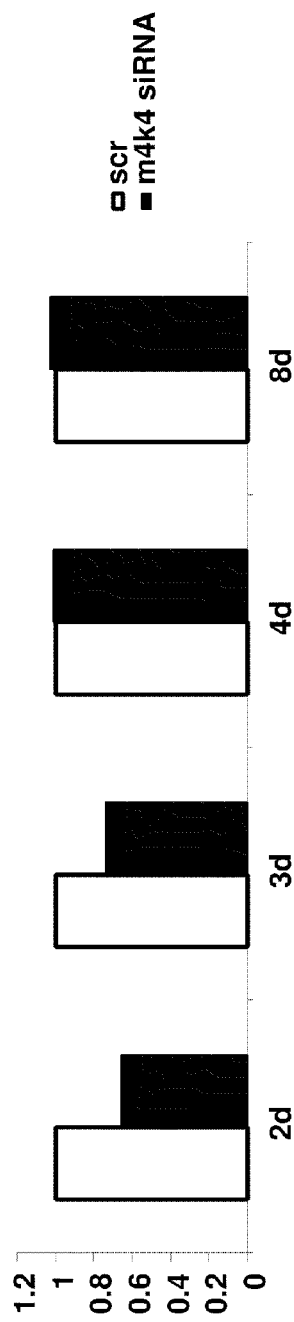
FIG. 18 shows Map4k4 expression in spleen macrophages isolated from mice treated similarly.

Time Course Analysis of In Vivo Silencing of Map4k4 Using IP Injected, siRNA-Loaded FITC-YCWP Ten-week old C57BL6/J mice were IP injected daily for 3 days, with 100 ug ($5 \times 10^7$) FITC-YCWP, containing 0.25 ug, scrambled or Map4k4 siRNA. 1, 2, 3 or 7 days after the last injection, mice were IP injected with thioglycollate. Macrophages were isolated from the peritoneum and the spleen 24 hours after the thioglycollate injection. FIG. 16 shows the timeline for the treatments and cell isolations from the mice in this experiment. Macrophages attached and erythrocytes were eliminated by washes. RNA was isolated from peritoneal (FIG. 17) or spleen macrophages (FIG. 18) to measure Map4k4 expression using real time PCR. The 36B4 gene was used as an internal control (not shown in the figures). Map4k4 expression was reduced in peritoneal macrophages through day 8 and in spleen macrophages up to day 4.

Figure 19:
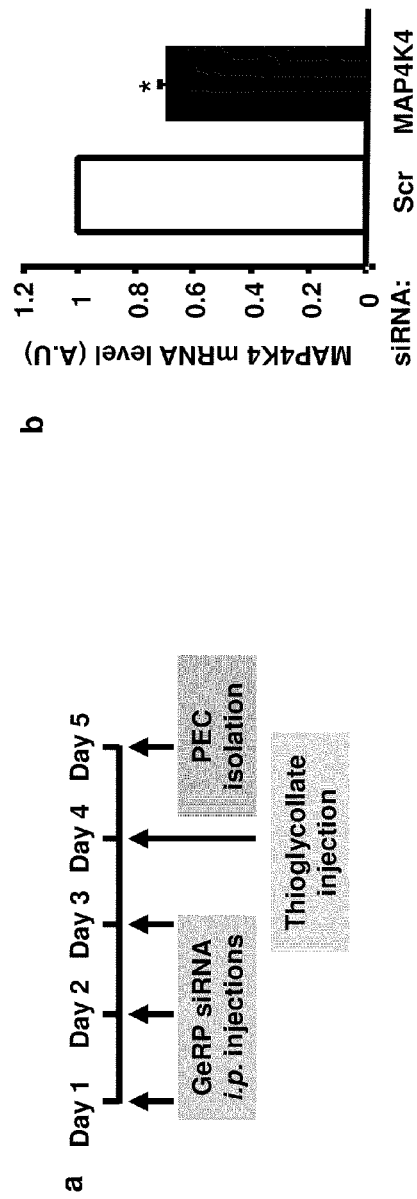
FIG. 19 shows that I.P. administration of GeRPs containing MAP4K4 siRNA reduce MAP4K4 mRNA expression in macrophages in vivo.

The efficacy of MAP4K4 siRNA-GeRPs to silence MAP4K4 expression was also tested in macrophages following delivery by i.p. injection of Dy547-labeled MAP4K4 siRNA or Scr siRNA in FL-GeRPs. Previous studies indicated that 3 daily i.p. injections of $2 \times 10^9$ empty glucan shells/kg achieved their substantial delivery to macrophages in mice (Beier, R. & Gebert, A., Am J Physiol 275, G130-7 (1998); Hong, F. et al. J Immunol 173, 797-806 (2004), both of which are hereby incorporated by reference in their entirety). Mice were treated once daily for 3 days by i.p. injections of 10 μg/kg Dy547-labeled MAP4K4 siRNA or Scr siRNA in $2 \times 10^9$/kg FL-GeRPs, and then treated with thioglycollate on day 4 (FIG. 19a). Fluorescence microscopy revealed Dy547-siRNA containing GeRPs within recovered macrophages in PECs, resulting in a 30% knockdown of MAP4K4 mRNA (FIG. 19b). These results show that similar to oral delivery, i.p. administration of GeRPs causes efficient gene silencing in macrophages in vivo.

Example 10

Orally Administered FITC-GPs are Taken Up by Migratory GALT Macrophases and Migrate into Spleen, Lung and Liver To test glucan shells for oral delivery to macrophages throughout the body, mice were orally gavaged once daily for 8 days with FL-glucan shells and then spleen, liver, lung and skeletal muscle tissues were procured (FIG. 20a). Tissue sections were prepared and analyzed by fluorescence microscopy for the presence of macrophages containing FL-glucan shells. These studies revealed extensive infiltration of spleen, liver and lung with fluorescent cells, which could be seen at higher magnification to harbor FL-glucan shells. These cells were identified as macrophages using F4/80 antibody. In contrast, analysis of skeletal muscle showed little or no evidence of FL-glucan shell-containing cells. These data demonstrate that macrophages in the GALT internalize orally absorbed glucan shells and move out of the gut to infiltrate various tissues throughout the body. Furthermore, a significant proportion of macrophages throughout the body contain labeled glucan shells after oral gavage.

In order to evaluate GeRPs for oral delivery of siRNA-mediated gene silencing in vivo, mice were given Dy547-conjugated Scr or MAP4K4 siRNA (1) (10 ug/kg) contained within FL-GeRPs ($4 \times 10^9$ FL-GeRPs/kg) by oral gavage once daily for 8 consecutive days. The mice were then i.p. injected with thioglycollate on day 9 and PECs were isolated on day 10 (see protocol in FIG. 20b). Staining the PECs recovered from these mice with the macrophage-specific antibody F4/80-AlexaFluor405 followed by fluorescence microscopy revealed that the FL-GeRPs containing Dy547-siRNA were indeed efficiently taken up by macrophages. Co-localization of AlexaFluor405, FL, and Dy547 fluorescent signals in adherent macrophages was readily observed. Strikingly, MAP4K4 mRNA expression as assessed by RT-PCR revealed a 70% knockdown in PECs isolated from mice orally gavaged with MAP4K4 siRNA-GeRPs compared to PECs from control mice treated with Scr siRNA-GeRPs (FIG. 20c).

Example 11

In Vivo Map4k4 Silencing Using siRNA-Loaded FITC-YCWP by Oral Gavage

Figure 21:
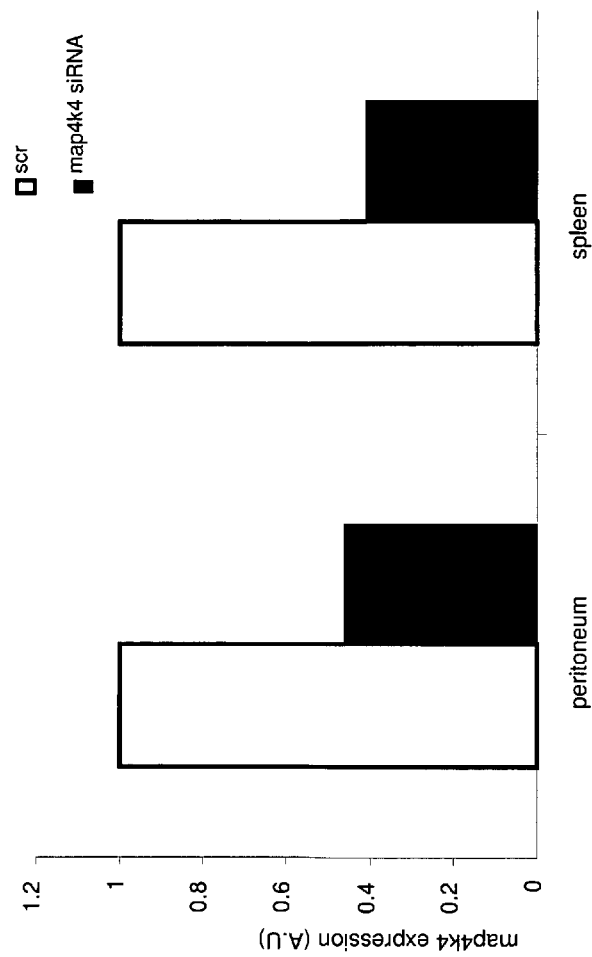
FIG. 21 compares Map4K4 expression in peritoneal vs. spleen macrophages and FIG. 22 compares Map4K4 expression in peritoneal vs. lung macrophages.
Figure 22:
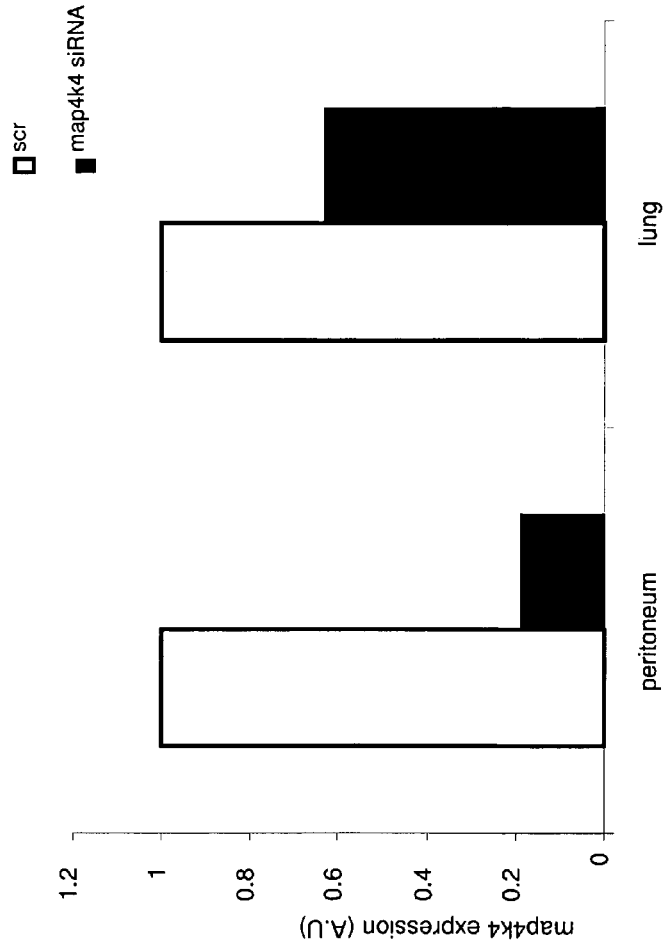
Figure 23:
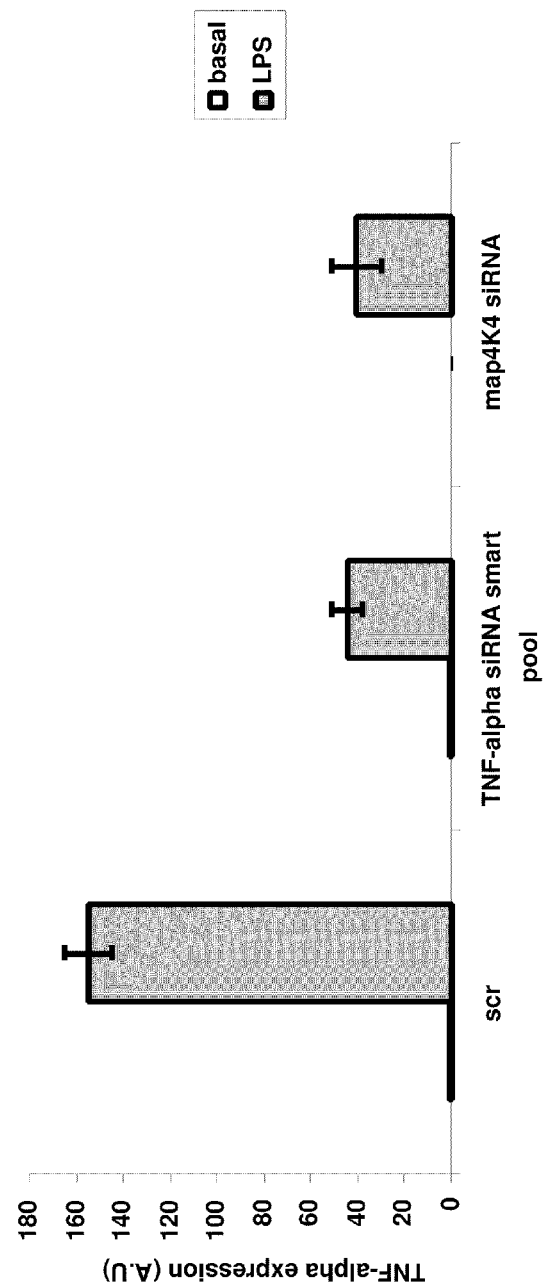
FIG. 23 shows the effects of Map4k4 or TNFalpha siRNA FITC-GeRP injections on lipopolysaccharide-provoked TNF-alpha expression in macrophages.

Ten-week old C57BL6/J mice were treated daily for 8 days with 200 ug ($1 \times 10^8$) FITC-YCWP, containing 0.25 ug, scrambled or anti-map4k4 siRNA, by oral gavage. Twenty-four hours after the last injection, mice were IP injected with thioglycollate. Macrophages were isolated from the peritoneum, the spleen or the lung 24 hours after the thioglycollate injection. FIG. 20b shows the time course of the treatments and isolations. Macrophages attached and erythrocytes were eliminated by washes. RNA was isolated from peritoneal, spleen, or lung macrophages to measure Map4k4 expression using real time PCR. FIG. 21 compares map4K4 expression in peritoneal vs. spleen macrophages and FIG. 22 compares map4K4 expression in peritoneal vs. lung macrophages. The 36B4 gene was used as an internal control (not shown). The figures show that siRNA-loaded YCWP can significantly suppress in vivo macrophage map4K4 expression in mice when delivered orally.

MAP4K4 silencing was also analyzed in macrophages that had migrated to other tissues by dissociating cells from spleen, liver, lung, and skeletal muscle tissues with collagenase on day 10 of the protocol (FIG. 20b), and then isolating an enriched macrophage population (see Methods). Significant depletions of about 50%, 80% and 40% in MAP4K4 mRNA levels were observed in these macrophage-enriched cells isolated from spleen, liver and lung tissues, respectively, in mice treated with MAP4K4 siRNA-GeRPs compared to the control mice treated with Scr siRNA-GeRPs (FIG. 20d). However, no effect on MAP4K4 expression was observed in macrophages derived from skeletal muscle (FIG. 20d), consistent with the lack of FL-glucan particle-containing macrophages found in skeletal muscle. As noted above in Example 10, macrophages isolated from spleen, liver and lung tissues of mice orally gavaged with fluorescently labeled GeRPs were seen to contain GeRPs, whereas GeRP-containing macrophages were not detected in muscle tissue samples from these mice. Taken together, these data indicate that macrophages in the GALT internalize orally absorbed GeRPs, undergo siRNA-mediated gene silencing and move out of the gut to infiltrate tissues throughout the body.

Figure 32:
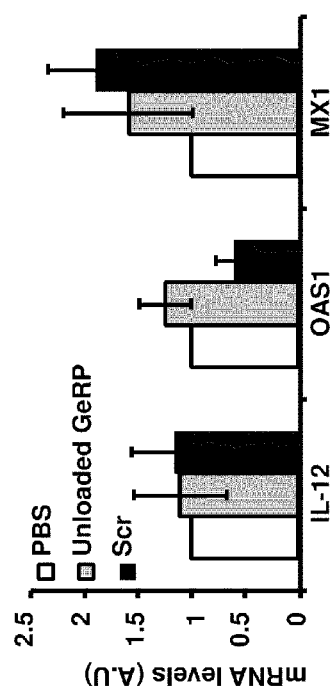
FIG. 32 shows interferon responses by macrophages in vitro after treatment with siRNA-GeRPs. $10^6$ PECs were treated with PBS, $10^7$ unloaded GeRPs (containing tRNA/PEI cores but no siRNA) or GeRPs loaded with 40 pmoles of Scr. Total RNA was harvested 48 hours after treatment and analyzed by real time PCR for the expression of INFβ target genes, OAS1 and MX1 or INFγ target genes, IL-12. Results are the mean±SEM (n=3).
Figure 33:
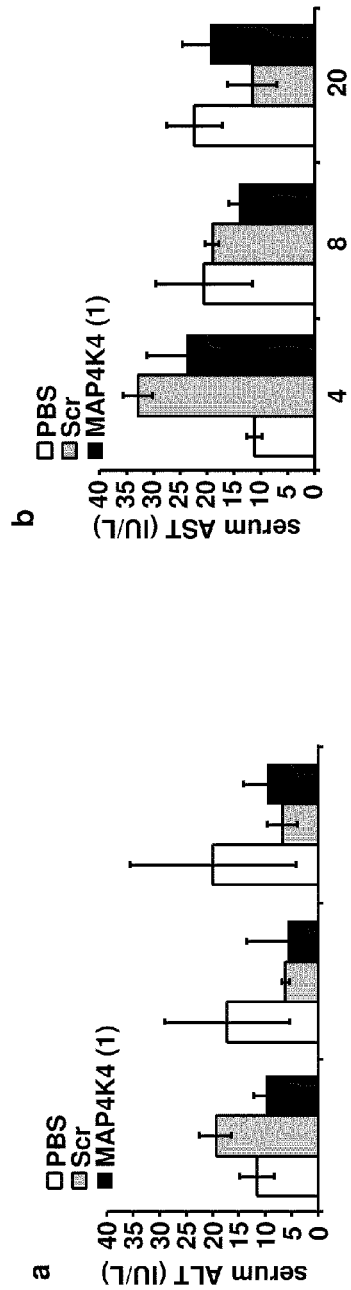
FIG. 33 shows serum liver enzyme levels in vivo after siRNA-GeRP oral treatment. Mice were gavaged with PBS or GeRPs containing 10 ug/kg of Scr or MAP4K4 (1) siRNA. (a) Alanine aminotransferase (ALT) and (b) aspartate aminotransferase (AST) were measured in serum 4, 8 and 20 days after the last gavage (n=3).

In order to confirm that gene silencing by orally delivered GeRPs can be mediated by multiple siRNAs, we also gavaged mice with GeRPs containing another MAP4K4 (MAP4K4 siRNA (2)) and two TNF-α siRNA oligonucleotides found to be effective on macrophages in vitro (see FIG. 10b-c). As shown in FIG. 20f-h, oral gavage of GeRPs containing these three other siRNA oligonucleotides (each tested separately) was highly effective in silencing the cognate genes in PECs as well as macrophage-enriched cells isolated from spleen, liver and lung. Importantly, oral gavage of GeRPs containing either siRNA or no siRNA (unloaded GeRPs) did not change interferon gamma levels in serum (FIG. 20e), consistent with lack of induction of interferon response genes in macrophages treated with GeRPs in vitro (FIG. 32). Serum levels of liver enzymes were also all within normal ranges (AST<255 IU/L; ALT<77 IU/L) (Schnell, M. A. et al. *Hum Gene Ther* 13, 155-61 (2002)) with little effect of any of the treatments (FIG. 33). Other experiments have indicated that the gene silencing with unmodified siRNA lasted about 8 days following the termination of oral administration of GeRPs under the conditions of these experiments (not shown). Thus, we have demonstrated efficient knockdown of two genes with 4 different siRNA sequences using orally delivered GeRPs.

Example 12

Effect of MAP4K4 Silencing on TNF-Alpha Expression by Peritoneal Macrophages In testing the effect of MAP4K4 silencing on the macrophage inflammatory response in vitro, macrophages were stimulated with lipopolysaccharide (LPS), a major structural component of the outer membrane of Gram-negative bacteria. LPS activates monocytes and macrophages to produce cytokines such as TNF-α and IL-1β that act as endogenous inflammatory mediators (Beutler, B, et al. *J Leukoc Biol* 74, 479-85 (2003)).

Figure 25:
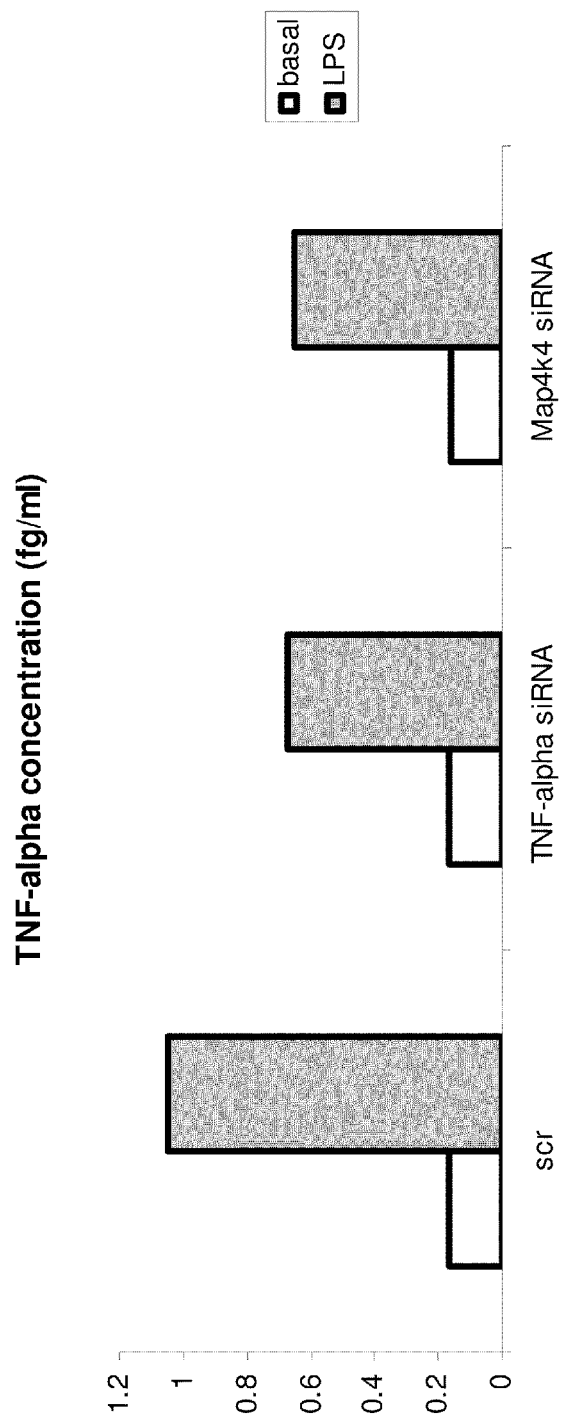
FIG. 25 shows concentrations of TNF-alpha (in fg/mL) secreted into cell culture media by lipopolysaccharide-treated macrophages after treatment with control or siRNA FITC-GeRPs.

Ten-week old C57BL6/J mice were IP injected with thioglycollate. Four days after injection, chemo-attracted macrophages were isolated from the peritoneum and plated. Macrophages attached and erythrocytes were eliminated by washes. $1\times10^6$ cells (PECs) were treated with $1\times10^7$ siRNA-loaded FITC-YCWP particles (GeRPs) containing 0.25 ug, or 40 pmoles, of siRNA (scrambled, anti-TFN-alpha (1) or anti-map4K4) and 1 ug/ml Lipopolysaccharide for 6 hours. Cells were harvested 48 hours later and RNA was isolated to measure TNF-alpha expression using real time PCR. The 36B4 gene was used as an internal control. As seen in FIG. 25, lipopolysaccharide-provoked TNF-alpha production in macrophages that received either anti-TNF-alpha or anti-map4K4 siRNA particles was only ⅓ of the production seen in the cells that received the negative control (scrambled) siRNA particles.

In a second experiment, cells (PECs) were incubated with GeRPs containing 40 pmoles of Scr or MAP4K4 siRNA for 48 h, and then treated with saline or LPS for an additional 6 h before total mRNA was harvested and analyzed by RT-PCR. TNF-α mRNA levels were decreased by 40% in control cells treated with MAP4K4 siRNA-containing GeRPs compared to GeRPs containing Scr siRNA. Importantly, MAP4K4 silencing inhibited the LPS-induced TNF-α expression by nearly 50% (FIG. 24a), while use of a second siRNA sequence against MAP4K4 with the same protocol lead to an even more robust knockdown (FIG. 24b). This level of knockdown is comparable to that achieved using siRNA against TNF-α itself (FIG. 10). MAP4K4 silencing in PECs also resulted in an average 30% decrease of LPS-induced TNF-α protein secretion (see Example 13 below). GeRPs with Scr siRNA, unloaded GeRPs (GeRPs containing tRNA/PEI cores, but not siRNA) or PBS (no GeRPs), however, failed to affect TNF-α expression (see FIG. 12c) or secretion (FIG. 26b), nor did these control experiments have an effect on expression of interferon response genes (FIG. 32).

In additional experiments, PECs were incubated with GeRPs containing 40 pmoles of Scr (1) or MAP4K4 (1) siRNA as well as varying concentrations of LPS (0, 0.05, 0.1, 1 and 10 ug/ml). TNF-α expression was decreased by MAP4K4 expression at LPS concentrations of 0.1 ug/ml and above (FIG. 24c). A decrease in TNF-α secretion was seen, however, at the lowest LPS concentration, 0.05 ug/ml (FIG. 24d). Treatment with Scr (1) or Scr (2) siRNAs had no effects on expression levels of MAP4K4 or TNF-α (FIG. 24e).

Example 13

Effect of MAP4K4 Silencing TNF-Alpha Protein in Serum

Figure 26:
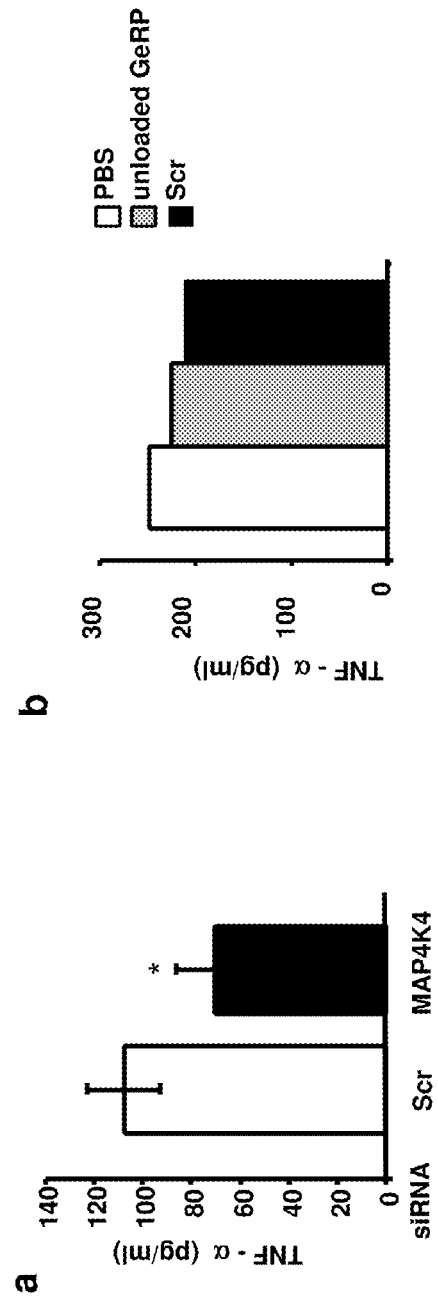
FIG. 26a shows TNF-α secretion by PECs treated with GeRP containing 40 pmoles of Scr or MAP4K4 siRNA.
FIG. 26b shows TNF-α secretion by PECs treated with GeRP containing 40 pmoles of Scr siRNA, unloaded GeRP (no siRNA) or PBS (no GeRP). TNF-α mRNA and protein levels were measured by RT-PCR and ELISA, respectively. Results are expressed in arbitrary units and are the mean±SEM (n=4). Statistical significance was determined by analysis of variance and a two tailed student's T-test. * (<0.01).

Ten-week old C57BL6/J mice were IP injected with thioglycollate. Four days after injection, chemo-attracted macrophages were isolated from the peritoneum and plated. Macrophages attached and erythrocytes were eliminated by washes. $1\times10^6$ cells were treated with $1\times10^7$ siRNA-loaded FITC-YCWP particles containing 0.25 ug or 40 pmoles of siRNA (scrambled, anti-TFN-alpha smart pool or anti-map4K4) and 1 ug/ml Lipopolysaccharide for 6 hours. Media samples were collected 48 hours later to measure TNF-alpha levels using an ELISA TNF-alpha assay. FIG. 26 shows concentrations of TNF-alpha (in fg/mL) secreted into cell culture media by treated macrophages. Treatment with YCWP containing either anti-TNF-alpha or anti-map4K4 siRNAs knocked down TNF-alpha expression by a significant amount, to about 70% of the control measurement.

When cells were treated with GeRPs containing 40 pmoles of Scr or MAP4K4 siRNA for 48 h, and then treated with saline or LPS for an additional 6 h MAP4K4, an average 30% decrease of LPS-induced TNF-α protein secretion was observed (FIG. 26a). Unloaded GeRPs and PBS (FIG. 26b), as well as empty glucan shells (data not shown), failed to elicit an inflammatory response in vitro as measured by TNF-α secretion.

Example 14

MAP4K4 Silencing does not Affect LPS Activation of Map Kinase and NFκB Signaling Pathways cJUN-n terminal kinases 1 and 2 (JNK1/2), extracellular signal-related kinase 1/2 (ERK1/2), p38 MAPK and NFκB pathways regulate TNF-α production in various cell types (Hacker, H. & Karin, M., *Sci STKE* 2006, rel3 (2006); Aouadi, M. et al. *Biochimie* 88, 1091-8 (2006)). Interestingly, it was found that MAP4K4 defines a proinflammatory pathway that activates TNF-α expression independently of the JNK1/2, p38, ERK1/2 and NFκB pathways (FIG. 27 a-g). Silencing MAP4K4 had no effect on the expression or phosphorylation of JNK1/2, p38 and ERK1/2, ATF2, or cJun. Similarly, no effect of MAP4K4 depletion on the degradation of the NFκB pathway regulator, IkBα in response to LPS was observed. Thus, MAP4K4 knockdown in primary macrophages failed to affect LPS-induced phosphorylation of these protein kinases, or LPS-induced degradation of IkBα in spite of its inhibition of TNF-α expression (FIG. 27 *a-g*). These data demonstrate that MAP4K4 is a novel target for suppression of TNF-α expression in LPS-induced macrophage inflammatory responses, in addition to its previously known role in mediating effects of TNF-α.

Example 15

Lipopolysaccharide Challenge of Mice After Oral Delivery of Anti-map4K4 siRNA-Containing YCWP Since MAP4K4 controls TNF-α expression and secretion by macrophages in vitro, a protocol was designed to test whether oral delivery of MAP4K4 siRNA-GeRPs attenuates cytokine production and LPS-induced lethality in mice (FIG. 28*a*). Preliminary experiments revealed there was no effect of 3 or 10 days of treatment with empty glucan shells by either oral gavage or i.p. administration on serum TNF-α levels (FIG. 13). Remarkably, an 80% decrease in TNF-α expression in PECs was observed in mice orally gavaged with GeRPs containing MAP4K4 siRNA versus Scr siRNA (FIG. 28*b*). This was accompanied by an equally dramatic 80% knockdown of the inflammatory cytokine IL-1β, but not IL-10, or the chemokine receptor CCR2, known to be downregulated by LPS (Martinez, F. et al. Front Biosci 13, 453-61 (2008); Zhou, Y. et al. J Leukoc Biol 65, 265-9 (1999)). These results indicate that silencing of MAP4K4 through oral delivery of GeRPs containing MAP4K4 siRNA potently down-regulates expression of the inflammatory cytokines TNF-α and IL-1β in macrophages in vivo. Importantly, unlike MAP4K4 siRNA, TNF-α siRNA does not silence expression of IL-1β in macrophages, showing specificity of this response to MAP4K4 knockdown (FIG. 28*e*: MAP4K4 siRNA knockdown both TNF-α and IL-1β expression; FIGS. 28*f* and 28*g*: TNF-α siRNAs fail to knock down IL-1β expression.)

Circulating TNF-α protein levels were next measured after challenging mice with injections of LPS and D-galactosamine (D-GalN), known to elicit a powerful inflammatory response. Ten-week old C57BL6/J mice were treated daily for 8 days (day 1 to day 8) with 200 ug ($1\times10^8$) FITC-YCWP, containing 0.25 ug anti-map4k4 siRNA, by oral gavage. On day 8 mice were IP injected with a single dose of D-galactosamine (25 mg/mouse) followed by an IP injection of *P. gingivalis* LPS (0.25 ug/mouse). All animals were continuously monitored for LPS-induced D-galactosamine-dependent lethality for 24 h after LPS challenge (n=6 per treatment group). Mortality was assessed every hour or every 2 hours for 24 h. Consistent with previous reports (Endo, Y. et al. Br J Pharmacol 128, 5-12 (1999)), we found that circulating TNF-α levels are strongly elevated 1.5 h after LPS/D-GalN injection and then decrease to basal levels after 4 h. Oral delivery of GeRPs containing MAP4K4 siRNA blocked the elevation in serum TNF-α protein induced by LPS/GalN injection. In these mice a significant decrease of TNF-α levels in peritoneal fluid 1.5 h after D-GalN/LPS injection was also observed (FIG. 28*c*). These data demonstrate a striking down-regulation of the TNF-α response to an inflammatory stimulus by depletion of MAP4K4 mRNA through oral delivery of GeRPs.

Figure 29:
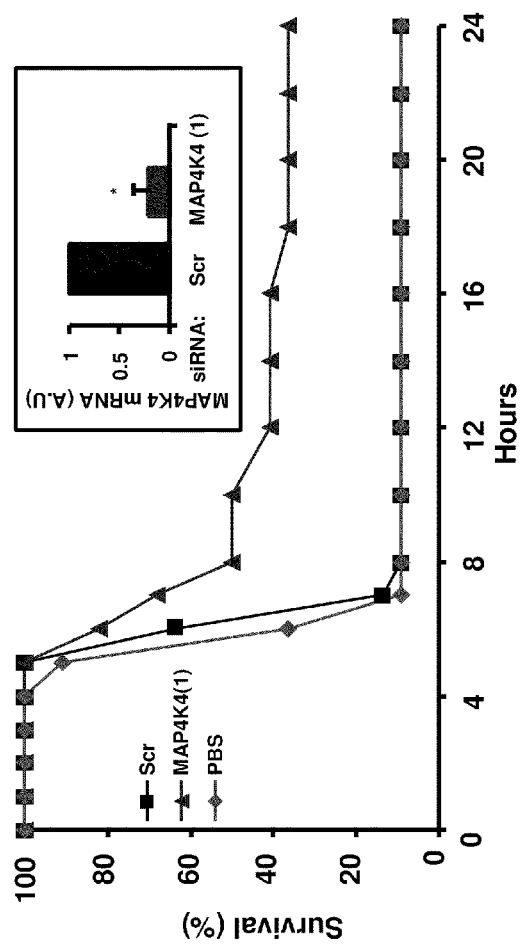
FIG. 29 shows percent survival of mice orally treated with siRNA formulations, then injected with LPS/D-GalN. Survival was assessed every hour for 24 hours. Additional groups of three mice treated orally with siRNA GeRPs but without LPS were used in each experiment to assess the MAP4K4 knockdown in the PECs (inset). Results are the mean of three independent experiments. The survival probabilities for mice treated with PBS (no GeRP), GeRP Scr (n=22) and GeRP MAP4K4 (1) siRNA (n=22) formulations were determined using Kaplan-Meier analysis. Statistical significance was assessed using Log Rank (Mantel-Cox) (p<0.01).

Lethality observed in LPS/D-GalN-challenged animals is attributed to inflammatory cytokine toxicity and can be mimicked by administration of TNF-α and IL-1β, which synergize with each other (Okusawa, S. et al. J Clin Invest 81, 1162-72 (1988)). Furthermore, mice lacking the TNF-α receptor TNFRp55 and mice (C3H/HeJ) deficient in TNF-α and IL-1β release are resistant to LPS-induced lethality (Pfeffer, K. et al. Cell 73, 457-67 (1993); Poltorak, A. et al. Science 282, 2085-8 (1998)). Normal mice can also be protected from lethal endotoxemia by agents that selectively inhibit TNF-α and/or IL-1β action or release (Novogrodsky, A. et al. Science 264, 1319-22 (1994); Maruyama, H. et al. Shock 13, 160-5 (2000), both of which are hereby incorporated by reference). It was therefore tested whether such protection is elicited by oral delivery of MAP4K4 siRNA-GeRPs using the protocol in FIG. 28*a*. After daily oral gavage for 8 days with Scr siRNA or MAP4K4 siRNA GeRPs (10 ug siRNA/kg), mice were injected i.p. with 25 mg of D-GalN followed by 0.25 μg of LPS. As shown in FIG. 29, 90% of the control mice treated with Scr siRNA-containing GeRPs died between 4 and 8 h (i.e., none of the mice given the YCWP with the control scr siRNA survived beyond 7 hours post-LPS challenge). In contrast, 50% of the mice treated with MAP4K4 (1) siRNA containing GeRPs survived for 8 h after LPS/D-GalN injection. One-third (~40%) of the mice given the anti-map4K4 YCWP survived the LPS challenge to 24 hours post-challenge and the time to death for the non-survivors was extended as compared to the control animals (Table 4).

TABLE 4

Survival post LPS-challenge of mice treated with PBS, Scr or MAP4K4 siRNA-GeRPs.

| Hours after LPS/D-Galactosamine Injection Hours after LPS/D-Galactosamine Injection | Number of Mice Surviving at Indicated Time Point PBS | Number of Mice Surviving at Indicated Time Point Scr | Number of Mice Surviving at Indicated Time Point MAP4K4 |
|---|---|---|---|
| 0 | 5 | 22 | 22 |
| 6 | 1 | 14 | 18 |
| 7 | 1 | 3 | 15 |
| 8 | 1 | 2 | 11 |
| 10 | 1 | 2 | 9 |
| 24 | 1 | 2 | 8 |

This difference between administration of Scr versus MAP4K4 siRNA was highly statistically significant using Kaplan-Meier analysis and Mantel-Cox testing (p<0.01) (Table 5).

TABLE 5

Statistical testing of the equality of survival probabilities between Scr and MAP4K4 siRNA-GeRP treatments in the LPS/D-galactosamine challenge.

| | Chi-Square | Df | Sig. |
|---|---|---|---|
| Log Rank | 8.334 | 1 | 0.004 |
| Breslow | 8.799 | 1 | 0.003 |
| Tarone-Ware | 8.99 | 1 | 0.003 |

Figure 30:
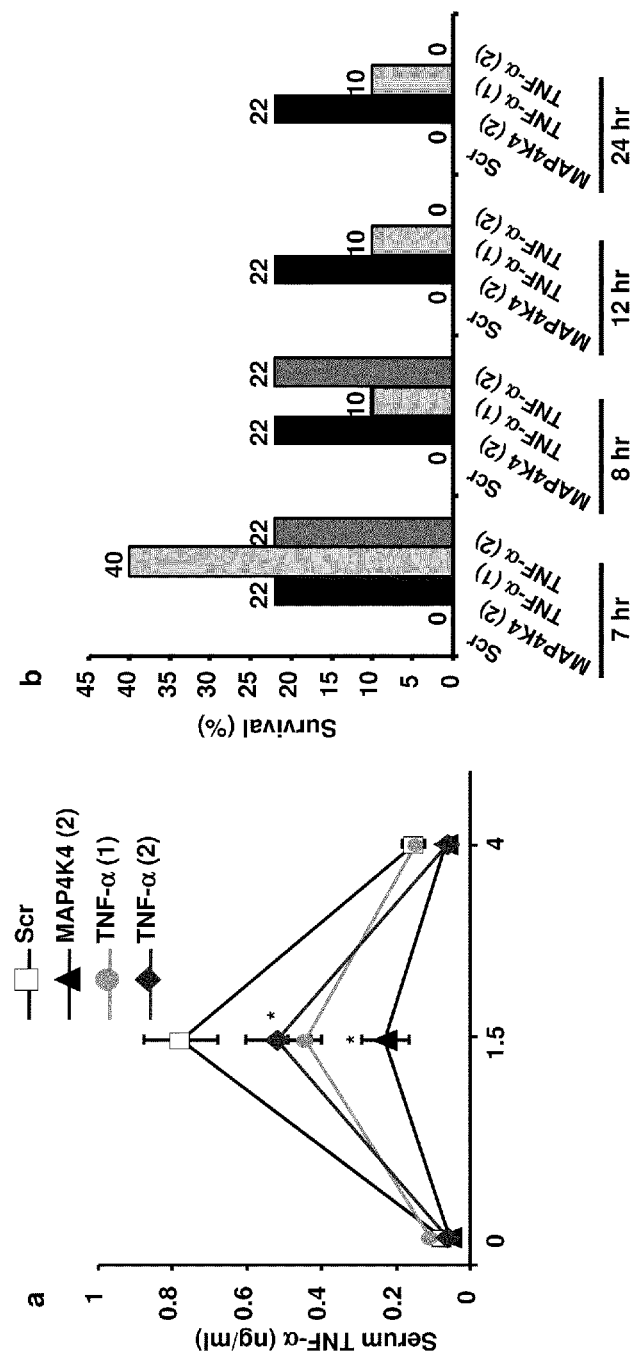
FIG. 30 shows serum TNFα levels in mice orally treated with siRNA-loaded GeRPs (Scr, MAP4K4 (2), TNF-α (1) and TNFα (2)) (FIG. 30a) and percent survival after injection with LPS/D-GalN (FIG. 30b).

Subsequent experiments showed protection from LPS-induced TNF-α production and lethality in vivo by MAP4K4 (2) siRNA and TNFα siRNAs. As above, mice were gavaged with siRNA-GeRPs. Four hours after the final gavage, mice were i.p. injected with D-GalN, followed by an i.p. injection of LPS. FIG. 30*a* shows serum TNF-α levels in siRNA treated mice 1.5 and 4 hours after LPS/D-GalN injection, with MAP4K4 (2) siRNA showing the strongest suppression of TNF-α production. Results are the mean±SEM (n=5). Statistical significance was determined by ANOVA and Tukey post test; *p<0.05. FIG. 30b shows the percent survival of mice orally treated with siRNA-GeRPs followed by LPS/DGalN injections. No mice treated with GeRPs containing Scr siRNA survived, even for 7 hours.

Figure 31:
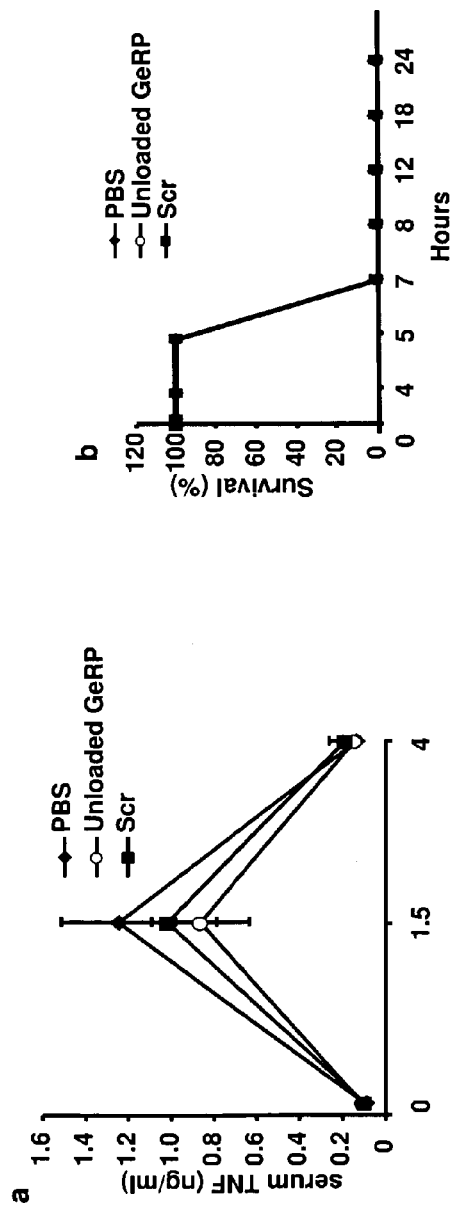
FIG. 31 shows serum TNF-α levels (panel a) and percent survival of mice (panel b) orally treated with control GeRP formulation and PBS (no GeRPs). Survival was assessed every hour for 24 hours.

FIG. 31 shows that unloaded GeRPs (containing tRNA/PEI cores but no siRNA) or GeRPs loaded with scrambled siRNA have no effect on LPS-induced TNF-α production and lethality in vivo. Mice were gavaged with unloaded GeRPs or GeRPs loaded with 10 ug/kg of Scr siRNA. Four hours after the final gavage, mice were i.p. injected with D-GalN, followed by an i.p. injection of LPS. TNF-α levels are shown in FIG. 31a and were measured 1.5 and 4 hours after LPS/D-GalN injection. Results are the mean±SEM (n=5). Statistical significance was determined by ANOVA and Tukey post test. FIG. 31b shows percent survival of mice orally treated with Scr siRNA-loaded GeRPs, unloaded GeRPs and PBS (no GeRPs) and then injected with LPS/D-GalN. Survival was assessed every hour for 24 hours. Treatment with Scr siRNA-loaded GeRPs and unloaded GeRPs had no effect on survival times.

In murine models, it is well accepted that the lethal effects of LPS/D-GalN challenge are due to hepatocyte apoptosis (Silverstein, R. J Endotoxin Res 10, 147-62 (2004)). Thus, we employed TUNEL assays to detect apoptosis in liver of mice treated with Scr or MAP4K4 siRNA-GeRPs, 4 and 28 h post D-GalN/LPS injection. TUNEL assay was performed on liver histological sections from mice 4 and 28 hours after LPS/D-Galn injection. Hepatocyte apoptosis in response to LPS injection was strongly attenuated by MAP4K4 siRNA-GeRPs. Thus, silencing of MAP4K4 expression by oral gavage of MAP4K4 siRNA-GeRPs significantly protects mice from GalN/LPS-induced lethality through inhibition of TNF-α and IL-1β production in macrophages.

Several technical features of the GeRP delivery system described here are notable. Most remarkable, the in vivo potency of 10 ug siRNA/kg in GeRPs to mediate gene silencing is 10 to 500 times greater than previous studies reporting systemic delivery by intravenous injection. For significant effects in vivo, intravenous injection of siRNA formulations require doses ranging from 125 ug/kg to 50 mg/kg in mice (Filleur, S. et al. Cancer Res 63, 3919-22 (2003); McCaffrey, A. P. et al. Nature 418, 38-9 (2002); Peer, D. et al. Proc Natl Acad Sci USA 104, 4095-100 (2007); Song, E. et al. Nat Biotechnol 23, 709-17 (2005); Soutschek, J. et al. Nature 432, 173-8 (2004); Wesche-Soldato, D. E. et al. Blood 106, 2295-301 (2005), all of which are hereby incorporated by reference in their entirety) and 1 mg/kg in nonhuman primates (Zimmermann, T. S. et al. Nature 441, 111-4 (2006), hereby incorporated by reference in its entirety). For attenuation of LPS-induced lethality in mice by i.p. injection, 1.2 mg TNF-α siRNA/kg was required (Sorensen, D. R. et al. J Mol Biol 327, 761-6 (2003), hereby incorporated by reference in its entirety). These studies generally employed chemically modified siRNA to enhance stability. The high potency of orally delivered siRNA within GeRPs (10 ug/kg) is all the more surprising since unmodified siRNA was used in our studies. This high potency is likely due to protection of siRNA against nuclease degradation by PEI within GeRPs, low non-specific binding of the GeRPs enroute to Peyers' patches of the gut, and to the high efficiency of GeRP uptake by phagocytic cells in the GALT. Furthermore, the siRNA loading capacity within the hollow cavity of glucan shells is far greater than we have used here, and has the potential to orally co-deliver combinations of siRNA, DNA, proteins and small molecules. Potentially GeRPs could be modified to facilitate transfer of siRNA from macrophages and dendritic cells to neighboring cells, thus effecting gene silencing in many tissues and cell types.

The present results demonstrating a potent attenuation of the macrophage inflammatory response to LPS following GeRP-mediated delivery of siRNA against TNF-α or MAP4K4 have significant therapeutic implications. Inflammatory cytokines and TNF-α in particular are pathogenic in humans, and injectable anti-TNF-α protein therapeutics are successful commercial products for the treatment of rheumatoid arthritis, ankylosing spondylitis, Crohn's disease, and psoriasis (Shealy, D. J. & Visvanathan, S. Handb Exp Pharmacol, 101-29 (2008)). Macrophage-mediated pathogenesis is also well characterized in mouse models of obesity-associated insulin resistance (Ferrante, A. W., Jr. J Intern Med 262, 408-14 (2007)) and atherosclerosis (Hansson, G. K. & Libby, P. Nat Rev Immunol 6, 508-19 (2006)) while such autoimmune diseases as type 1 diabetes involve the deleterious actions of inflammatory cytokines (Shoda, L. K. et al. Immunity 23, 115-26 (2005); Koulmanda, M. et al. Proc Natl Acad Sci USA 104, 13074-9 (2007)). Modulation of inflammation by GeRP-mediated delivery of siRNA may also benefit these and other human maladies.

Example 16

Use of MAP4K4 and aP2 as Targets for siRNA Therapeutics in Type 2 Diabetes

Macrophage infiltration of adipose tissue has been shown to be a key event in progression of type 2 diabetes in obese humans. The inflammation caused by macrophages contributes to the insulin resistance in adipose tissue and skeletal muscle that drives abnormal glucose tolerance and diabetes. MAP4K4 siRNA loaded into GeRPs effectively lowers both basal and LPS-stimulated TNFα production from macrophages and decreases inflammation. Experiments were performed to evaluate MAP4K4 as a potential therapeutic target for Type 2 Diabetes.

Genetically obese, leptin deficient (ob/ob) mice that exhibit rapid onset of insulin resistance (by 8 weeks of age) were used to test the ability of GeRP-mediated gene knockdown to improve whole body metabolism and insulin sensitivity. A number of different genes and gene products have been implicated in obesity using the ob/ob model system. For example, the development of obesity is associated with increased adipose TNF-α levels and the utilization of neutralizing antibodies against TNF-α improved insulin sensitivity and lowered inflammatory markers in the ob/ob model system. Additional therapeutic targets for increasing insulin sensitivity that have been implicated by this model include the protein aP2. The following experiments were designed to use GeRPs to attenuate aP2 and/or MAP4K4 expression and attenuate insulin resistance.

Results i.p. Injection of GeRPs Targets Visceral Adipose Macrophages: To determine whether i.p. injections of GeRPs were targeting macrophage populations in adipose and other tissues, tissues were isolated from leptin deficient genetically obese (ob/ob) mice after 8 single daily injections of unloaded, fluorescently labeled GeRPs ($1.25 \times 10^9$ GeRPs/kg/day). The tissues were harvested and single cell suspensions were prepared through collagenase digestion and filtration. Single cells were stained for the monocyte/macrophage marker F4/80 using anti F4/80 antibody and analyzed by fluorescence activated cell (FACs) analysis. The majority of GeRPs appeared in macrophages within the stromal vascular fraction of the epididymal fat pad.

GeRPs Containing MAP4K4 and aP2 siRNA Silence Target Gene Expression in Epididymal Adipose Tissue: To evaluate the efficiency of gene silencing, macrophages were isolated from various tissues following i.p. administration of GeRPs.

Figure 34:
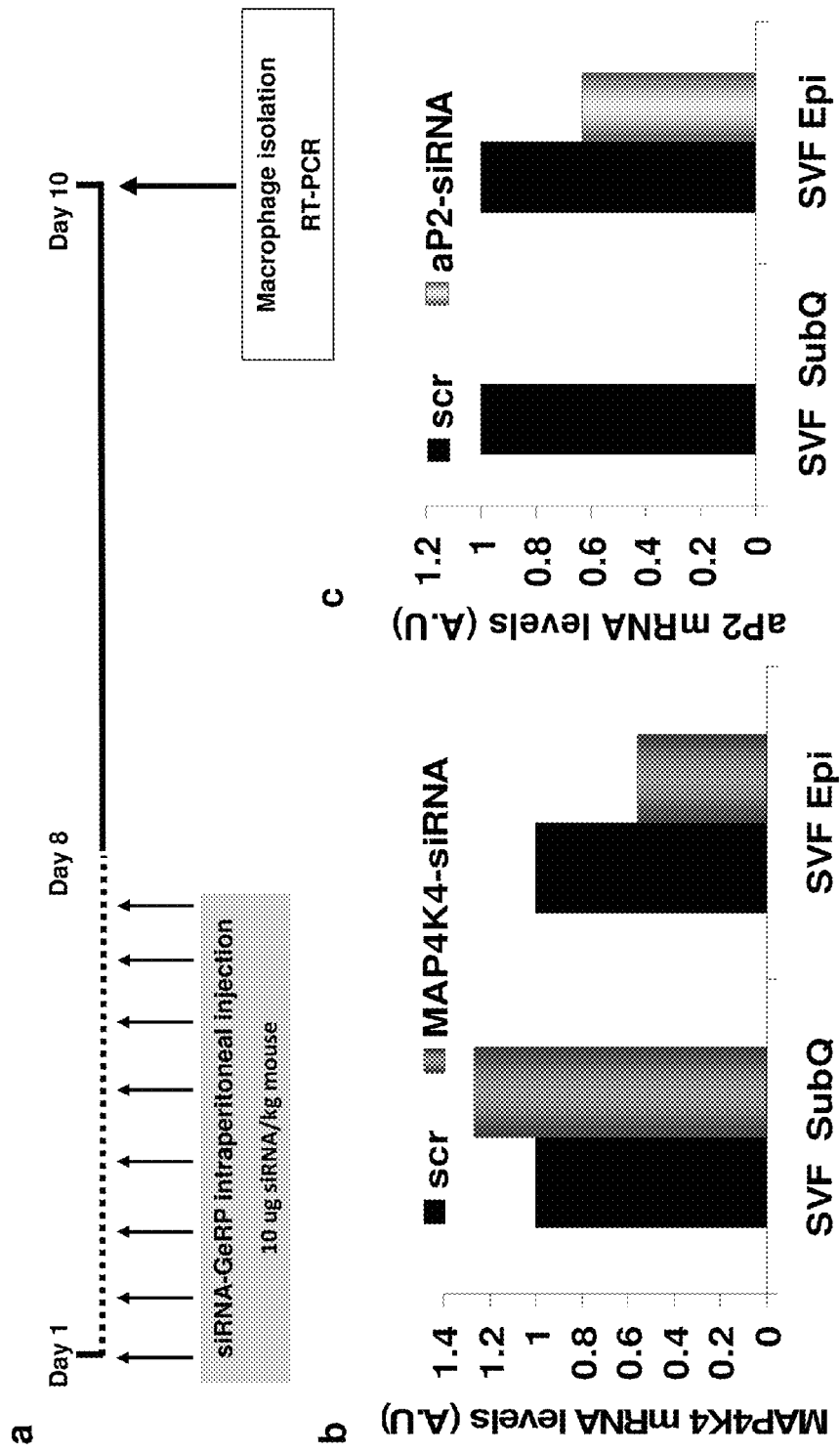
FIG. 34 shows that i.p. injections of GeRPs containing MAP4K4 and aP2 siRNAs (protocol, panel a) reduces gene expression in subcutaneous (panel b) and epididymal fat pad (panel c) macrophages.

Mice were injected for 8 days with unloaded, GeRPs ($1.25 \times 10^9$ GeRPs/kg/day) containing scrambled, MAP4K4 or aP2 siRNA (10 μg/kg). Tissue macrophages were isolated on the $10^{th}$ day by collagenase digestion (5 mg/ml at 37° C. with shaking at 200 RPMs), filtration through 75 micron filter, concentrated by centrifugation and enriched by plating in serum free DMEM for 3 hours (FIG. 34a). Adherent cells were harvested with trizol and (FIG. 34b) MAP4K4 and (FIG. 34c) aP2 expression was measured by real time PCR.

MAP4K4 GeRP administration silenced MAP4K4 expression in epididymal (Epi) adipose tissue macrophages but not macrophages obtained from subcutaneous (SubQ) adipose tissue (FIG. 34b). aP2 siRNA containing GeRP administration silenced aP2 expression in subcutaneous and epididymal macrophages (FIG. 34c).

Figure 35:
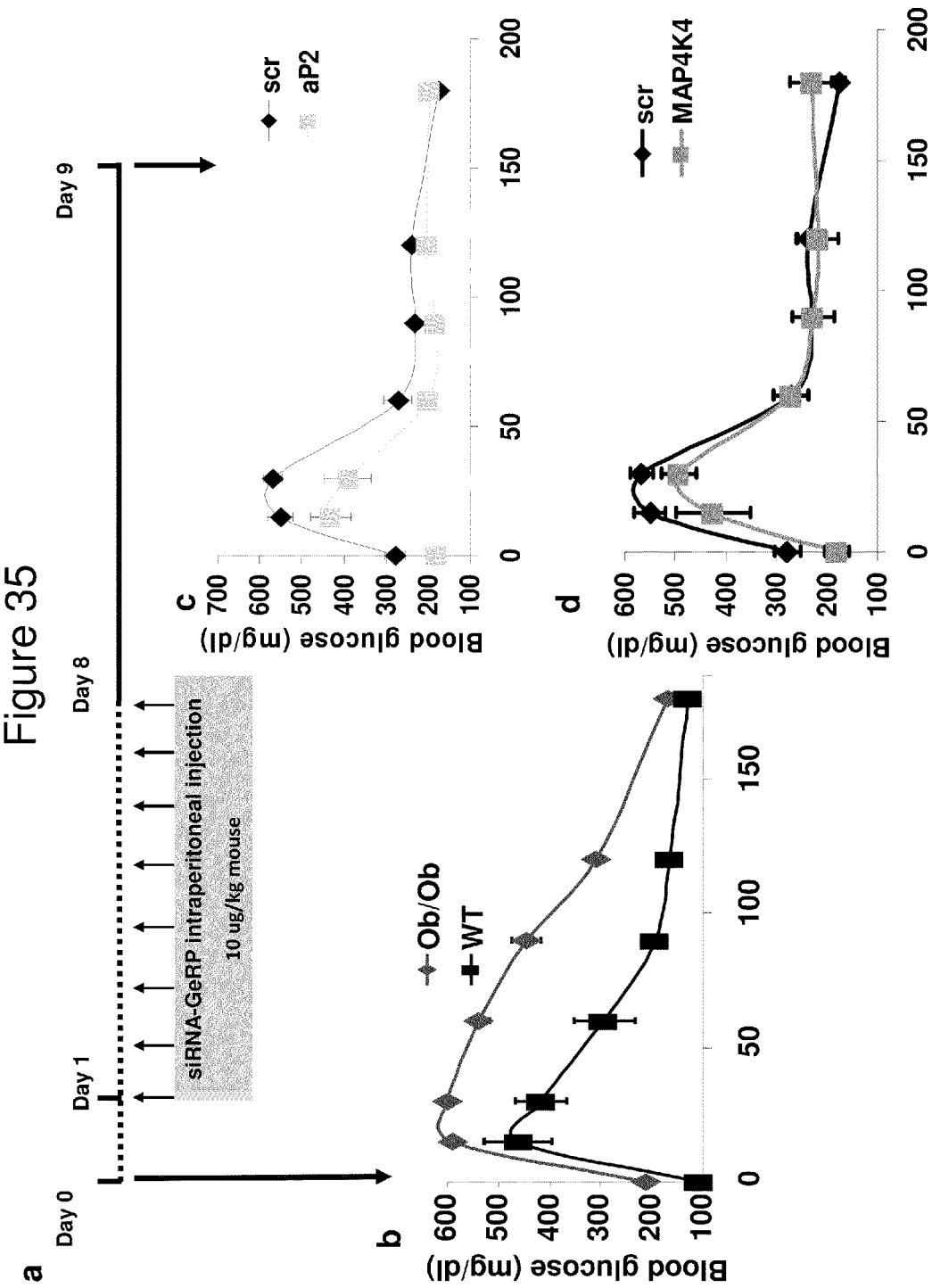
FIG. 35 shows that i.p. injections of GeRPs containing MAP4K4 and aP2 siRNAs (protocol, panel a) in ob/ob mice which exhibit glucose intolerance (control, panel b) can increase glucose tolerance (i.e., reduce peak plasma glucose levels) (panels c and d).

Administration of GeRPs to attenuate insulin resistance in ob/ob mice: The efficacy of GeRP treatment in attenuating insulin resistance was evaluated next. Mice were treated as indicated in FIG. 35a. Briefly, glucose tolerance was assessed in 8 week old mice to evaluate whole body glucose sensitivity. Mice were injected with glucose (1 g/kg) and changes in blood glucose levels were monitored. As expected, ob/ob mice were significantly more glucose intolerant than lean littermates (FIG. 35b). Following the glucose tolerance test, mice were administered GeRPs containing either scrambled siRNA or siRNA targeting MAP4K4 or aP2. Mice were injected daily for 8 days i.p. with $1.25 \times 10^9$ GeRPs/kg containing 10 μg/kg of the appropriate siRNA. Following 8 days of i.p. injections, a second glucose tolerance test was performed on day 9 (FIGS. 35c and 35d).

The increase in glucose sensitivity in response to MAP4K4 siRNA GeRP treatment was significant and the effect of aP2 siRNA-loaded GeRPs was more substantial. These experiments show that GeRP delivery of siRNA to macrophages is a potential mechanism for improving glucose sensitivity.

Conclusion: Delivery of GeRPs loaded with siRNA against aP2 and MAP4K4 was shown to improve insulin sensitivity. The results demonstrate that GeRPs can be utilized to treat metabolic disease and its symptoms (e.g, glucose intolerance) using established targets like aP2, and that MAP4K4 attenuation enhances insulin sensitivity.

Example 17

Effect of aP2 Knockdown on Inflammatory Markers

The effects of aP2 knockdown mediated by GeRP delivery of aP2 siRNA to PECs in vitro and by oral gavage was studied.

GeRPs loaded with aP2 siRNA, Scr siRNA (either (1) or (2)) or MAP4K4 (1) siRNA, or unloaded GeRPs, were incubated with PECs extracted as detailed above. As seen in FIG. 36a, only PECs treated with GeRPs carrying aP2 siRNA showed knock down of aP2 gene expression, not PECs treated with Scr siRNA GeRPs or unloaded GeRPs. In FIG. 36b, the effects on PECs of treatment with GeRPs carrying 40 pmol of aP2 siRNA, Scr siRNA (either (1) or (2)) or MAP4K4 (1) siRNA are shown. MAP4K4 and aP2 siRNAs knocked down their respective genes in PECs in vitro. In FIG. 36c, the effects of siRNA-carrying GeRPs on TNFα production by PECs in vitro is shown, either with or with LPS treatment. Only MAP4K4 siRNA demonstrated the ability to significantly knock down TNFα expression in PECs in vitro, under both conditions. FIG. 36d confirms this finding, showing that only PECs treated with MAP4K4 siRNA-carrying GeRPs show a decrease in TNFα secretion.

Figure 37:
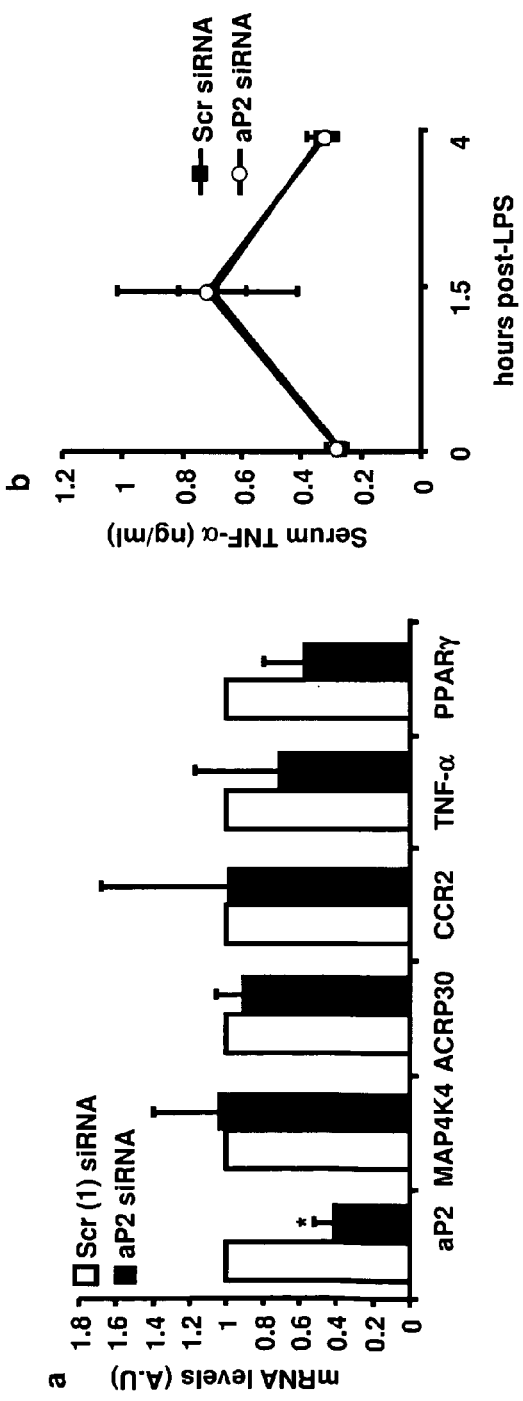
FIG. 37a shows analysis of aP2, MAP4K4, ACRP30, CCR2, TNF-α and PPAR-γ expression in PECs recovered from treated mice. Results are the mean±SEM (n=3).
FIG. 37b shows serum TNF-α levels in siRNA treated mice 1.5 and 4 hours after LPS/D-GalN injection measured by ELISA (n=6).

GeRPs loaded with aP2 siRNA or Scr siRNA were delivered by oral gavage (10 ug/kg Scr or aP2 siRNA daily for 8 days), injected with thioglycollate on day 9 and PECs were then isolated on day 10. FIG. 37a shows analysis of aP2, MAP4K4, ACRP30, CCR2, TNF-α and PPAR-7 expression in PECs recovered from treated mice. Results are the mean±SEM (n=3). Expression of aP2 showed a significant decrease (<0.03).

To examine the effects of GeRPs on TNFα secretion in vivo, mice were gavaged with GeRPs loaded with 10 ug/kg of Scr or aP2 siRNA. Serum TNF-α levels in siRNA treated mice 1.5 and 4 hours after LPS/D-GalN injection measured by ELISA (n=6) and are shown in FIG. 37b. Treatment with GeRPs loaded with aP2 siRNA had no effect on serum TNFα levels.

Statistical significance was determined by two tailed student's T-test for FIG. 37a and by ANOVA and Tukey post test for FIG. 37b.

EQUIVALENTS

The invention has been described herein with reference to certain examples and embodiments only. No effort has been made to exhaustively describe all possible examples and embodiments of the invention. Indeed, those of skill in the art will appreciate that various additions, deletions, modifications and other changes may be made to the above-described examples and embodiments, without departing from the intended spirit and scope of the invention as recited in the following claims. It is intended that all such additions, deletions, modifications and other changes be included within the scope of the following claims.

We claim:

1. A method of reducing or inhibiting inflammation in a subject having an inflammatory disease or disorder comprising, administering to the subject a siRNA-delivery system, comprising yeast cell wall particles (YCWPs), wherein the YCWPs individually comprise a yeast cell wall particle (YCWP) exterior and a multilayered nanoparticle interior, wherein the multilayered nanoparticle interior comprises a cationic nucleic acid core, coated with at least one siRNA layer, wherein the siRNA layer is coated with at least one cationic trapping layer, wherein the multilayered nanoparticle interior is produced by first introducing into the YCWP exterior, components to form the cationic nucleic acid core such that the core forms inside the YCWP exterior, followed by introducing siRNA such that the siRNA layer forms on the surface of the core, followed by introducing a trapping molecule such that the trapping layer forms on the siRNA layer, and wherein the siRNA targets a gene involved in inflammation, wherein the siRNA is present at a ratio of about $0.1 \times 10^{-7}$ to $100 \times 10^{-7}$ pmol siRNA per YCWP, wherein the siRNA-delivery system is administered under conditions facilitating delivery of the siRNA to phagocytic cells of the subject, such that inflammation is reduced or inhibited in the subject having the inflammatory disease or disorder.

2. The method of claim 1, wherein the conditions facilitate phagocytosis of the siRNA delivery system, such that delivery of the siRNA occurs.

3. The method of claim 1, wherein the phagocytic cells are selected from the group consisting of a monocyte, monocytic cells, neutrophil cells, dendritic cells and macrophage cells.

4. The method of claim 1, wherein the phagocytic cells are macrophage cells.

5. The method of claim 1, wherein the inflammatory disease or disorder is a TLR4-mediated disease or disorder, and wherein the siRNA targets a TLR4 signaling component.

6. The method of claim 1, wherein the disease is a metabolic disease or disorder.

7. The method claim 1 or 6, wherein the siRNA delivery system is administered systemically.

8. The method of claim 1, wherein the disease or disorder is selected from the group consisting of an autoimmune disorder, sepsis, an intestinal disorder, an infectious disease, a malignancy, a pulmonary disorder, a cardiac disorder, and a neurological disorder.

9. The method of claim 8, wherein the disease or disorder is selected from the group consisting of Crohn's disease, HIV, arthritis, cardiovascular disease and cancer.

10. The method of claim 1 or 6, wherein the siRNA delivery system is administered orally.

11. The method of claim 6, wherein the disease or disorder is selected from the group consisting of glucose tolerance, insulin sensitivity, diabetes and obesity.

12. The method of claim 6, wherein the siRNA targets aP2.

13. The method of claim 6, wherein the siRNA targets Map4k4, under conditions facilitating delivery of the siRNA to macrophage, wherein silencing of Map4k4 results in enhanced insulin sensitivity in the subject.

14. The method of claim 12 or 13, wherein the siRNA delivery system is administered orally.

15. The method claim 12 or 13, wherein the siRNA delivery system is administered systemically.

16. The method of claim 12 or 13, wherein the subject has Type 2 Diabetes.

17. The method of claim 1 or 6, wherein the YCWPs comprise at least a second siRNA coated with a second trapping layer.

18. The method of claim 1, wherein the core comprises a cationic detergent.

19. The method of claim 1, wherein the core comprises an anionic polymer coated with a cationic polymer, such that the core is cationic on the surface.

20. The method of claim 1, wherein the siRNA is a Map4k4 siRNA.

21. The method of claim 1, wherein the siRNA is an inflammatory cytokine siRNA.

22. The method of claim 1, wherein the siRNA is a TNFα siRNA.

23. The method of claim 1, wherein the siRNA is a RIP140 siRNA.

24. The method of claim 1, wherein the siRNA is a TLR4 siRNA.

25. The method of claim 1, wherein the siRNA is an aP2 siRNA.

26. The method of claim 1, wherein the core further comprises the siRNA.

27. The method of claim 25, wherein the core and siRNA layer comprise the same siRNA.

28. The method of claim 25, wherein the core and siRNA layer comprise distinct siRNAs.

29. The method of claim 1, wherein the siRNA is present at a ratio of about $1 \times 10^{-7}$ to $10 \times 10^{-7}$ pmol siRNA per YCWP.

30. The method of claim 1, wherein the trapping layer comprises a cationic polymer, a cationic detergent or a mixture thereof.

31. The method of claim 1, wherein the core comprises a cationic polymer, a cationic detergent or a mixture thereof.

32. The method of claim 30 or 31, wherein the cationic polymer is selected from the group consisting of chitosan, poly-L-lysine and polyethylenimine (PEI).

33. The method of claim 19, wherein the anionic polymer is an alginate or a xanthan.

34. The method of claim 19, wherein the anionic polymer is a nucleic acid.

35. The method of claim 34, wherein the nucleic acid is transfer RNA (tRNA).

36. The method of claim 1, wherein the YCWP is chemically modified to comprise a cell or tissue specific targeting agent.

37. The method of claim 1, wherein the siRNA delivery system delivers from 0.1 to 100 µg/kg to the subject as a unit dose.

38. The method of claim 1, wherein the siRNA delivery system delivers from 1 to 10 µg/kg to the subject as a unit dose.

* * * * *

SEQUENCE LISTING

<160> NUMBER OF SEQ ID NOS: 36

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 1
gaccaacucu ggcuuguua                                               19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2 cguugguug aucaccacg                                                19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ggaaugagcu cgauuauaa                                               19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gaagaagaga ggcgagaaa                                               19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uuacagaccu ugugaagaa                                               19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ggagagaaca agaagaaaa                                               19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
```
ggccagaggu ugaaaguga                                                19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gagcaauggu gaaacggaa                                                19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ugguggaagu gguuggaaa                                                19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ggugaaacuu guugacuuu                                                19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ggauugagca gcagaaaga                                                19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gaggagaguu gaaagagaa                                                19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
ccaaaugaaa ggcaaguua                                                19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
cagucgcguu ugcgacugg                                               19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cagaagtggc caagggaaa                                               19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcatggatct caaagacaa                                               19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cgaccacaat aaagagaaa                                               19

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaccattagc cttgtgtgta ctgtatg                                      27

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tggatcgatt gtgcttcaag tt                                           22

<210> SEQ ID NO 20

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
catctccagg gaaatcctca gg                                              22

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttctgtagtc gtaagtggcg tctg                                            24

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccctcacact cagatcatct tct                                             23

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gctacgacgt gggctacag                                                  19

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcaactgttc ctgaactcaa ct                                              22

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atcttttggg gtccgtcaac t                                               21

<210> SEQ ID NO 26
<211> LENGTH: 22
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 26
ctggacaaca tactgctaac cg                                              22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gggcatcact tctaccaggt aa                                              22

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
atccacggca tactatcaag atc                                             23

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
caagggtcac catcatggta g                                               21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
attacctcct tcccgacacc                                                 20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caaactccac ctcctgatgc                                                 20

<210> SEQ ID NO 32
<211> LENGTH: 23
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 32
gatccgactt cacttccaga tgg                                           23

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
catctcagtg gtagtcaacc c                                             21

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agacatggag tcataggctc tg                                            22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccattttcct tcttgtggag ca                                            22

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgaccacaat aaagagaaa                                                19
```